United States Patent
Botton et al.

(10) Patent No.: US 8,232,272 B2
(45) Date of Patent: Jul. 31, 2012

(54) BENZIMIDAZOLEDIHYDRO-THIADIAZINONE DERIVATIVES AS FRUCTOSE-1,6-BISPHOSPHATASE INHIBITORS, AND PHARMACEUTICAL COMPOSITIONS COMPRISING SAME

(75) Inventors: Gerard Botton, Buc (FR); Caroline Leriche, Paris (FR); Annick Arbellot de Vacqueur, Fontenay les Briis (FR); Annick Audet, Leudeville (FR); Johannes Gleitz, Darmstadt (DE)

(73) Assignee: Merck Patent Gesellschaft mit beschränkter Haftung, Darmstadt (DE)

( * ) Notice: Subject to any disclaimer, the term of this patent is extended or adjusted under 35 U.S.C. 154(b) by 190 days.

(21) Appl. No.: 12/742,375

(22) PCT Filed: Oct. 13, 2008

(86) PCT No.: PCT/EP2008/008631
§ 371 (c)(1),
(2), (4) Date: May 11, 2010

(87) PCT Pub. No.: WO2009/062576
PCT Pub. Date: May 22, 2009

(65) Prior Publication Data
US 2010/0286129 A1    Nov. 11, 2010

(30) Foreign Application Priority Data
Nov. 12, 2007 (EP) .................................. 07291349

(51) Int. Cl.
*C07D 417/04* (2006.01)
*C07D 417/14* (2006.01)
*A61K 31/54* (2006.01)

(52) U.S. Cl. ........................................ 514/222.5; 544/8
(58) Field of Classification Search .... 544/8; 514/222.5
See application file for complete search history.

(56) References Cited

U.S. PATENT DOCUMENTS
4,916,128 A    4/1990 Jonas et al.
5,401,738 A *  3/1995 Mederski et al. .......... 514/222.5

FOREIGN PATENT DOCUMENTS
EP          0 294 647 A2    12/1988
WO      WO 99/14239 A1     3/1999

OTHER PUBLICATIONS

International Search Report of PCT/EP2008/008631 (Jun. 8, 2009).
T. Ishitani et al., "Effects of Ca2+ Sensitizers on Contraction, [CA2+]i Transient and Myofilament Ca2+ Sensitivity in Diabetic Rat Myocardium: Potential Usefulness as Inotropic Agents", The Journal of Pharmacology and Experimental Therapeutics, vol. 298, No. 2 (2001) pp. 613-622.
H. Soga et al., "Preparation and Formulation of Benzimidazole Derivatives for Treatment of Heart Failure", Database CA [Online] Chemical Abstracts Service, XP002477495 (1995).

* cited by examiner

*Primary Examiner* — Kahsay T Habte
(74) *Attorney, Agent, or Firm* — Millen, White, Zelano & Branigan, P.C.

(57) ABSTRACT

The present invention relates to novel benzimidazole-dihydrothiadiazinone derivatives as fructose-1,6-bisphosphatase inhibitors, to processes for the preparation thereof and to the use thereof in therapy, especially for the treatment of diabetes.

26 Claims, No Drawings

BENZIMIDAZOLEDIHYDRO-THIADIAZINONE DERIVATIVES AS FRUCTOSE-1,6-BISPHOSPHATASE INHIBITORS, AND PHARMACEUTICAL COMPOSITIONS COMPRISING SAME

The present invention relates to dihydrothiadiazinone derivatives that are inhibitors of fructose-1,6-bisphosphatase, to the preparation thereof, and to the therapeutic use thereof in the treatment of pathologies associated with insulin resistance syndrome.

"Diabetes mellitus" (or diabetes) is one of the most prevalent diseases in the to world today. Individuals suffering from diabetes are divided into two classes, namely type I or insulin-dependent diabetes mellitus and type II or non-insulin-dependent diabetes mellitus (NIDDM). NIDDM accounts for approximately 90% of all diabetics, and is estimated to affect 12 to 14 million adults in the United States alone (6.6% of the population).

NIDDM is characterised both by fasting hyperglycaemia and exaggerated postprandial increases in plasmatic glucose levels. NIDDM is associated with a variety of long-term complications, including microvascular diseases, such as retinopathy, nephropathy and neuropathy, and macrovascular diseases, such as coronary heart disease.

Numerous studies in animal models show a causal relationship between long-term complications and hyperglycaemia. Recent results obtained by the Diabetes Control and Complications Trial (DCCT) and the Stockholm Prospective Study have for the first time demonstrated this relationship in man by showing that insulin-dependent diabetics have a substantially lower risk of development and progression of these complications if they are subjected to tighter glycaemic control. Tighter control is also expected to benefit NIDDM patients.

Current therapies used for the treatment of NIDDM patients involve both controlling lifestyle risk factors and pharmaceutical intervention. First-line therapy for NIDDM patients is usually a strictly controlled regimen of diet and exercise, since an overwhelming number of NIDDM patients are overweight or obese ($\approx$67%) and since loss of weight can improve insulin secretion and insulin sensitivity, and lead to normoglycaemia.

Normalisation of blood glucose takes place in fewer than 30% of these patients due to poor compliance and poor response. Patients suffering from hyperglycaemia not controlled by diet alone are subsequently treated with insulin or oral hypoglycaemiants. At the present time, insulin secretors (sulfonylureas and glinides), biguanides (metformin) and insulin sensitisers (glitazone) are the only classes of oral hypoglycaemiants available for NIDDM. Treatment with sulfonylureas leads to an effective reduction in blood glucose in only 70% of patients and only 40% after 10 years of therapy. Patients for whom diet and sulfonylureas have no effect are then treated with daily insulin injections in order to establish adequate glycaemic control.

Although sulfonylureas represent a major therapy for NIDDM patients, four factors limit their overall success. Firstly, as indicated above, a large proportion of the NIDDM population does not respond adequately to sulfonylurea therapy (i.e. primary failures) or becomes resistant (i.e. secondary failures). This is particularly true in the case of NIDDM patients with advanced NIDDM, due to the fact that these patients suffer from severely impaired insulin secretion. Secondly, sulfonylurea therapy is associated with an increased risk of severe hypoglycaemic episodes. Thirdly, chronic hyperinsulinaemia is associated with an increase in cardiovascular diseases, although this relationship is considered controversial and unproven. Finally, sulfonylureas are associated with weight gain, which leads to worsening of peripheral insulin sensitivity and may consequently accelerate the progression of the disease.

Recent results from the UK Diabetes Prospective Study also show that patients subjected to maximal therapy of a sulfonylurea, metformin, or a combination of the two, were unable to maintain normal fasting glycaemia over the six-year period of the UK Prospective Diabetes Study, 16. *Diabetes,* 44, 1249-158 (1995). These results also illustrate the great need for alternative therapies. Three therapeutic strategies that could provide additional benefits as regards the health of NIDDM patients beyond the currently available therapies include medicaments that would: (i) prevent the onset of NIDDM; (ii) prevent diabetic complications by blocking harmful events precipitated by chronic hyperglycaemia; or (iii) normalise glucose levels or at least reduce glucose levels below the threshold reported for microvascular and macrovascular diseases.

Hyperglycaemia in the case of NIDDM sufferers is associated with two biochemical abnormalities, namely insulin resistance and impaired insulin secretion. The relative roles of these metabolic abnormalities in the pathogenesis of NIDDMs have been the subject of numerous studies over the last several decades. Studies performed on the offspring and siblings of NIDDM patients, on monozygotic and dizygotic twins, and on ethnic populations with a high incidence of NIDDM (for example Pima Indians), strongly support the hereditary nature of the disease.

Despite the presence of insulin resistance and impaired insulin secretion, fasted blood glucose (FBG) levels remain normal in the case of prediabetic patients on account of a state of compensatory hyperinsulinaemia. Eventually, however, the insulin secretion is inadequate and leads to fasting hyperglycaemia. Over time, the insulin levels decrease. Progression of the disease is characterised by increasing FBG levels and decreasing insulin levels.

Numerous clinical studies have attempted to define the primary defect involved during the progressive increase in FBG levels. The results of these studies show that excessive hepatic glucose output (HGO) is the first reason for the increase in the FBG levels, with a significant correlation found for HGO and FBG once the FBG levels exceed 140 mg/dL. Kolterman et al., *J. Clin. Invest.,* 68, 957, (1981); DeFronzo, *Diabetes,* 37, 667, (1988).

HGO comprises glucose derived from the breakdown of hepatic glycogen (glycogenolysis) and glucose synthesised from 3-carbon precursors (gluconeogenesis). A large number of radioisotopic studies, and also several studies using $^{13}$C-NMR spectroscopy, show that gluconeogenesis accounts for 50% to 100% of the glucose produced by the liver in the post-absorptive state and that the glucoeogenesis flux is excessive (2- to 3-fold) in the case of NIDDM patients. Magnusson et al., *J. Clin. Invest.,* 90, 1323-1327, (1992); Rothmann et al., *Science,* 254, 573-76, (1991); Consoli et al., *Diabetes,* 38, 550-557, (1989).

Gluconeogenesis from pyruvate is a highly regulated biosynthetic pathway that requires eleven enzymes. Seven enzymes catalyse reversible reactions and are common to both gluconeogenesis and glycolysis. Four enzymes catalyse reactions specific to gluconeogenesis, namely pyruvate carboxylase, phosphoenolpyruvate carboxykinase, fructose-1,6-bisphosphatase and glucose-6-phosphatase. Overall flux is controlled throughout the biosynthetic pathway by the specific activities of these enzymes, the enzymes that catalyse the corresponding steps in the glycolytic direction, and by substrate availability. Dietary factors (glucose, fat) and hormones (insulin, glucagon, glucocorticoids, epinephrine) coordinatively regulate the enzymatic activities in the gluconeogenesis and glycolysis processes by means of gene expression and post-translational mechanisms.

Among the four enzymes specific to gluconeogenesis, fructose-1,6-bisphosphatase (referred to hereinbelow as "FBPase") is a very suitable target for a gluconeogenesis inhibitor based on efficacy and safety considerations. Studies show that nature uses the FBPase/PFK cycle as a main control point (metabolic switch) for determining whether the metabolic flux is proceeding in the direction of glycolysis or gluconeogenesis. Claus et al., *Mechanisms of Insulin Action*, Belfrage, P. Editor, pp. 305-321, Elsevier Science, (1992); Regen et al., *J. Theor. Bio.*, 635-658, (1984); Pilkis et al., *Ann. Rev. Biochem.*, 57, 755-783, (1988). FBPase is inhibited by fructose-2,6-bisphosphate in the cell. Fructose-2,6-bisphosphate binds to the substrate site of the enzyme. AMP binds to an allosteric site on the enzyme.

Synthetic FBPase inhibitors have also been reported. Maryanoff has reported that fructose-2,6-bisphosphate analogues inhibit FBPase by binding to the substrate site. (*J. Med. Chem.*, 106, 7851, (1984); U.S. Pat. No. 4,968,790). However, these compounds show relatively low activity and do not inhibit glucose production in hepatocytes, undoubtedly on account of poor cell penetration.

Numerous fructose-1,6-bisphosphatase inhibitors that are useful in the treatment of diabetes have been reported:

Gruber has reported that some nucleosides can lower blood glucose in the whole animal by inhibition of FBPase (EP 0 427 799 B1). These compounds exert their activity by first performing a phosphorylation to the corresponding monophosphate;

Gruber et al. (U.S. Pat. No. 5,658,889) have described the use of inhibitors of the AMP site of FBPase for the treatment of diabetes;

Dan et al. (WO 98/39344, WO 00/014095) have described novel purines and heteroaromatic compounds as FBPase inhibitors;

Kasibhatla et al. (WO 98/39343) have described novel benzimidazolyl-phosphonates as FBPase inhibitors;

Reddy et al. (WO 98/39342) have described novel indoles and azaindoles as FBPase inhibitors;

Jaing et al. (WO 01/047935) have described bisamidate-phosphonates as specific FBPase inhibitors for the treatment of diabetes;

Bookser et al. (WO 01/066553) have described heterocycle phosphates as specific FBPase inhibitors for the treatment of diabetes;

Bauer et al. (US2003/0144308) have described quinazoline compounds as FBPase inhibitors for the treatment of diabetes and complications thereof;

Tsukuda et al. (WO2006104030) have described compounds containing a thiazole group as FBPase inhibitors for the treatment of diabetes, obesity, hyperlipidaemia, hypertension and arteriosclerosis;

Dang et al. (WO2006023515) have described thiazole derivatives as FBPase inhibitors for the treatment of diabetes and obesity.

The present invention relates to novel benzimidazoledihydrothiadiazinone derivatives as fructose-1,6-bisphosphatase inhibitors that can be used in the treatment of diabetes and related pathologies.

More particularly, the invention relates to benzimidazoledihydrothiadiazinone derivatives that are useful in the treatment of pathologies related to insulin resistance syndrome.

The compounds of the invention are of the general formula (I) below:

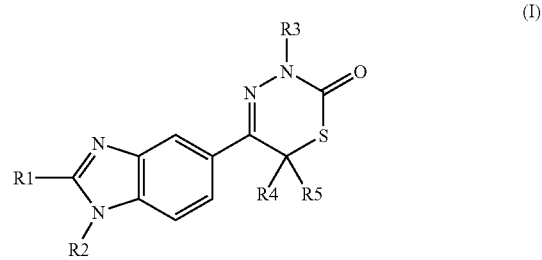

R1 represents a group chosen, without preference, from:
alkyl-, alkoxyalkyl-, alkenyl-, alkynyl-, each of these groups possibly being optionally substituted by one or more groups chosen from Y,
aryl-, arylalkyl-, aryloxyalkyl-, arylalkyloxyalkyl-, arylthioalkyl-, arylalkylthio-alkyl-,
heteroaryl-, heteroarylalkyl-, heteroaryloxyalkyl-, heteroarylalkyloxyalkyl-, heteroarylthioalkyl-, heteroarylalkylthioalkyl-,
cycloalkyl-, cycloalkylalkyl-, cycloalkyloxyalkyl-, cycloalkylalkyloxyalkyl-, cycloalkylthioalkyl-, cycloalkylalkylthioalkyl-,
heterocycloalkyl-, heterocycloalkylalkyl-, heterocycloalkyloxyalkyl-, hetero-cycloalkylalkyloxyalkyl-, heterocycloalkylthioalkyl-, heterocycloalkylalkyl-thioalkyl-, each of the groups aryl-, heteroaryl-, cycloalkyl-, heterocycloalkyl- possibly being optionally substituted by one or more groups chosen, without preference, from Y.

R1 may also represent a group A-B- consisting of two rings A and B linked via a bond and in which A and B independently represent a group chosen, without preference, from:
aryl-, heteroaryl-, cycloalkyl-, heterocycloalkyl-,
each of the groups aryl-, heteroaryl-, cycloalkyl-, heterocycloalkyl- possibly being is optionally substituted by one or more groups chosen, without preference, from Y.

R2 represents a group chosen, without preference, from:
H,
alkyl-, alkoxyalkyl-, alkenyl-, alkynyl-, each of these groups possibly being substituted by one or more groups chosen from Y,
aryl-, arylalkyl-, aryloxyalkyl-, arylalkyloxyalkyl-, arylthioalkyl-, arylalkylthio-alkyl-,
heteroaryl-, heteroarylalkyl-, heteroaryloxyalkyl-, heteroarylalkyloxyalkyl-, heteroarylthioalkyl-, heteroarylalkylthioalkyl-,
cycloalkyl-, cycloalkylalkyl-, cycloalkyloxyalkyl-, cycloalkylalkyloxyalkyl-, cycloalkylthioalkyl-, cycloalkylalkylthioalkyl-,
heterocycloalkyl-, heterocycloalkylalkyl-, heterocycloalkyloxyalkyl-, hetero-cycloalkylalkyloxyalkyl-, heterocycloalkylthioalkyl-, heterocycloalkylalkyl-thioalkyl-, each of the groups aryl-, heteroaryl-, cycloalkyl-, heterocycloalkyl- possibly being optionally substituted by one or more groups chosen, without preference, from Y.

R3 represents a group chosen, without preference, from:
H,
alkyl-, alkoxyalkyl-, hydroxyalkyl-, alkenyl-, alkynyl-, each of these groups possibly being optionally substituted by one or more groups chosen from Y,
  aryl-, arylalkyl-, aryloxyalkyl-, arylalkyloxyalkyl-, arylthioalkyl-, arylalkylthio-alkyl-,
  heteroaryl-, heteroarylalkyl-, heteroaryloxyalkyl-, heteroarylalkyloxyalkyl-, heteroarylthioalkyl-, heteroarylalkylthioalkyl-,
  cycloalkyl-, cycloalkylalkyl-, cycloalkyloxyalkyl-, cycloalkylalkyloxyalkyl-, cycloalkylthioalkyl-, cycloalkylalkylthioalkyl-,
  heterocycloalkyl-, heterocycloalkylalkyl-, heterocycloalkyloxyalkyl-, hetero-cycloalkylalkyloxyalkyl-, heterocycloalkylthioalkyl-, heterocycloalkylalkyl-thioalkyl-,
each of the groups aryl-, heteroaryl-, cycloalkyl- and heterocycloalkyl- possibly being optionally substituted by one or more groups chosen, without preference, from Y.

R4 and R5 independently represent a group chosen, without preference, from:
  H,
  W;
Y represents a group chosen, without preference, from:
  hydroxy-; thio-; halo-; trifluoromethoxy-; trifluoromethyl-; alkyloxy-; carboxyl-; alkoxycarbonyl-; carbamoyl-; sulfamoyl-; nitro-; guanidino-; amidino-; aryl-; heteroaryl-; amino-;

in which R8 represents a group chosen, without preference, from W;

in which R9 represents a group chosen, without preference, from W and p is chosen from 0, 1 and 2;

—(CH$_2$)$n$—O—R10 in which R10 represents a group chosen, without preference, from
  H,
  W,
and n is an integer between 0 and 8;

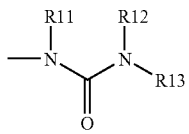

in which R11, R12 and R13 independently represent a group chosen, without preference, from:
  H,
  W,
it being understood that R12 and R13 may form a saturated or unsaturated mono- or bicyclic system of 3 to 10 atoms comprising from 1 to 3 heteroatoms, for example, and in a non-exhaustive manner, a piperidine, a morpholine, a substituted or unsubstituted piperazine, or a pyrrolidine;

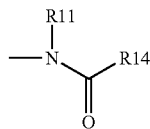

in which R11 represents a group chosen, without preference, from:
  H,
  W,
and in which R14 represents a group chosen, without preference, from W;

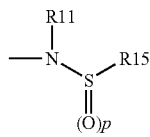

in which R11 represents a group chosen, without preference, from:
  H,
  W,
and in which R15 represents a group chosen, without preference, from W and p is chosen from 0, 1 and 2;
in which:
  Amino denotes a group

in which Ra and Rb are chosen, without preference, from
  H,
  W,
it being understood that Ra and Rb may form a saturated or unsaturated mono- or bicyclic system of 3 to 10 atoms comprising from 1 to 3 heteroatoms, for example, and in a non-exhaustive manner, a piperidine, a morpholine, a substituted or unsubstituted piperazine, or a pyrrolidine.

W represents a group chosen, without preference, from:
  alkyl-, alkenyl-, alkynyl-, aryl-, arylalkyl-, aryloxyalkyl-, arylalkyloxyalkyl-, arylthioalkyl-, arylalkylthioalkyl-, heteroaryl-, heteroarylalkyl-, heteroaryloxy-alkyl-, heteroarylalkyloxyalkyl-, heteroarylthioalkyl-, heteroarylalkylthioalkyl-, cycloalkyl-, cycloalkylalkyl-, cycloalkyloxyalkyl-, cycloalkylalkyloxyalkyl-, cycloalkylthioalkyl-, cycloalkylalkylthioalkyl-, heterocycloalkyl-, hetero-cycloalkylalkyl-, heterocycloalkyloxyalkyl-, heterocycloalkylalkyloxyalkyl-, heterocycloalkylthioalkyl-, heterocycloalkylalkylthioalkyl-,
each of these groups possibly being optionally substituted by one or more groups chosen, without preference, from
  hydroxyl-, thio-, halo-, trifluoromethoxy-, trifluoromethyl-, alkyloxy-, carboxyl-, alkoxycarbonyl-, carbamoyl-, sulfamoyl-, nitro-, guanidino-, amidino-, aryl-, heteroaryl-, amino- which has the same meaning as above, acetyl-;
in the form of tautomers, enantiomers, diastereoisomers or epimers, and also the pharmaceutically acceptable salts, and the crystalline forms, or mixtures thereof.

The present invention also relates to the particular methods for the preparation of the general formula (I) below taken in isolation, and also each of the combinations thereof.

In the general formula (I) presented above:
R1 represents an aryl group optionally substituted by one to four identical or different groups independently chosen from halogen, —OR, perhaloalkyl-, —S(O)$_p$—R, —NRR', —S—CH$_2$—CN or heteroaryl; or a -heteroaryl group, optionally substituted by one or more -alkyl groups; and/or R4 and R5, which may be identical or different, are independently chosen from a hydrogen atom and an -alkyl group.

Preferably, the present invention relates to the compounds of the general formula (I) represented above, in which:

R1 represents an aryl group optionally substituted by one to four identical or different groups independently chosen from halogen, —OR, perhaloalkyl-, —S(O)$_p$—R, —NRR', —S—CH$_2$—CN or heteroaryl; or a -heteroaryl group, optionally substituted by one or more -alkyl groups;

R2 represents a hydrogen atom; a -cycloalkyl group; an -alkyl group optionally substituted by a -cycloalkyl or -aryl group;

R4 and R5, which may be identical or different, are independently chosen from a hydrogen atom and an -alkyl group;

R3 represents:
a hydrogen atom;
an -alkyl group, optionally substituted by one or more groups chosen from:
OR, —O-heterocycloalkyl,
cycloalkyl,
heterocycloalkyl,
COOR,
CONRR',
NRR',
NRCO-alkyl, —NRCO-alkyl-aryl, —NRCO-cycloalkyl, —NRCO-aryl, —NRCO-heteroaryl, the aryl group being optionally substituted by a halogen atom or an alkyl group,
NRCOO-alkyl,
NRCO—NR-alkyl, —NRCO—NR-aryl or —NRCO—NR-alkyl-aryl, in which the aryl group is optionally substituted by a halogen atom or a group —COR;
NRCO—NR-cycloalkyl,
NRS(O)$_p$-aryl, —NRS(O)$_p$-alkyl,
aryl or —O-aryl, each aryl group being optionally substituted by one or more substituents chosen from halogen atoms and the groups -alkyl, —OR, perhaloalkyl-, perhaloalkyloxy- or —S(O)$_p$—R;
p=0, 1 or 2;

R, R', which may be identical or different, are independently chosen from H, -alkyl, -aryl, -heteroaryl, -cycloalkyl and -heterocycloalkyl, it being understood that R and R' may together form a saturated or unsaturated mono- or bicyclic system of 3 to 10 atoms comprising from 1 to 3 heteroatoms, for example, and in a non-exhaustive manner, a piperidine, a morpholine, a substituted or unsubstituted piperazine, or a pyrrolidine;

in the form of tautomers, enantiomers, diastereoisomers or epimers, and also the pharmaceutically acceptable salts, and the crystalline forms, or mixtures thereof.

Most preferentially, the present invention relates to the compounds of the general formula (I) represented above, in which:

R1 represents an aryl group optionally substituted by one to four identical or different groups independently chosen from halogen, —O-alkyl and —S(O)-alkyl;

R2 represents a hydrogen atom; a -cycloalkyl group; an -alkyl group;

R4 and R5, which may be identical or different, are independently chosen from a hydrogen atom and an -alkyl group;

R3 represents:
a hydrogen atom;
an -alkyl group, in the form of tautomers, enantiomers, diastereoisomers or epimers, and also the pharmaceutically acceptable salts, and the crystalline forms, or mixtures thereof.

The invention also relates to the tautomeric forms, the enantiomers, diastereoisomers and epimers, and the organic or mineral salts of the compounds of the general formula (I), and also the crystal forms including polymorphs, thereof and of the compounds of the formula (I).

The invention also covers the isomers and/or diastereoisomers, in pure form or as a mixture in any proportion of two or more thereof, including racemic mixtures.

The compounds of the formula (I) as defined above containing a sufficiently acidic function or a sufficiently basic function or both, may include the corresponding pharmaceutically acceptable salts of organic or mineral acids and/or of organic or mineral bases.

The acid salts are, for example, the hydrochlorides, hydrobromides, sulfates, hydrogen sulfates, dihydrogen phosphates, citrates, maleates, fumarates, trifluoroacetates, 2-naphthalenesulfonates and para-toluenesulfonates.

The bases that can be used for the formation of salts of compounds of the formula (I) are organic or mineral bases. The resulting salts are, for example, the salts formed with metals and especially with alkali metals, alkaline-earth metals and transition metals (such as sodium, potassium, calcium, magnesium or aluminium) or with bases, for instance ammonia or secondary or tertiary amines (such as diethylamine, triethylamine, piperidine, piperazine or morpholine) or with basic amino acids, or with osamines (such as meglumine) or with amino alcohols (such as 3-aminobutanol and 2-aminoethanol).

The invention also relates to the chiral salts used for the separation of racemates.

By way for example, the following chiral acids are used: (+)-D-di-O-benzoyl-tartaric acid, (−)-L-di-O-benzoyltartaric acid, (−)-L-di-O,O'-p-toluyl-L-tartaric acid, (+)-D-di-O,O'-p-toluyl-L-tartaric acid, (R)-(+)-malic acid, (S)-(−)-malic acid, (+)-camphanic acid, (−)-camphanic acid, R-(−)-1,1'-binaphthalene-2,2'-diyl-hydrogeno-phosphonic acid, (+)-camphoric acid, (−)-camphoric acid, (S)-(+)-2-phenylpropionic acid, (R)-(+)-2-phenylpropionic acid, D-(−)-mandelic acid, L-(+)-mandelic acid, D-tartaric acid, L-tartaric acid, or a mixture of two or more thereof.

Chiral amines may also optionally be used, for example quinine, brucine, (S)-1-(benzyloxymethyl)propylamine (III), (−)-ephedrine, (4S,5R)-(+)-1,2,2,3,4-tetra-methyl-5-phenyl-1,3-oxazolidine, (R)-1-phenyl-2-p-tolylethylamine, (S)-phenylglycinol, (−)-N-methylephedrine, (+)-(2S,3R)-4-dimethylamino-3-methyl-1,2-diphenyl-2-butanol, (S)-phenylglycinol or (S)-α-methylbenzylamine, or a mixture of two or more thereof.

The compounds of the formula (I) above also comprise the prodrugs of these compounds.

The term "prodrugs" means compounds which, when administered to the patient, are chemically and/or biologically converted in the live body into compounds of the formula (I).

Compounds according to the invention that may especially be mentioned include:
5-[2-(4-methoxyphenyl)-1H-benzimidazol-5-yl]-3,6-dihydro-2H-1,3,4-thiadiazin-2-one, 6-methyl-5-[2-(1H-pyrazol-3-yl)-1H-benzimidazol-5-yl]-3,6-dihydro-2H-1,3,4-thiadiazin-2-one,
6-methyl-5-[2-(2-thienyl)-1H-benzimidazol-5-yl]-3,6-dihydro-2H-1,3,4-thiadiazin-2-one,
5-[2-(3-methoxyphenyl)-1H-benzimidazol-5-yl]-6-methyl-3,6-dihydro-2H-1,3,4-thiadiazin-2-one,
6-methyl-5-(2-pyrid-4-yl-1H-benzimidazol-5-yl)-3,6-dihydro-2H-1,3,4-thiadiazin-2-one,
5-{2-[3-methoxy-4-(methylthio)phenyl]-1H-benzimidazol-5-yl}-6-methyl-3,6-dihydro-2H-1,3,4-thiadiazin-2-one,
5-{2-[2-methoxy-4-(methylthio)phenyl]-1H-benzimidazol-5-yl}-6-methyl-3,6-dihydro-2H-1,3,4-thiadiazin-2-one,
6-methyl-5-[2-(1,3-thiazol-4-yl)-1H-benzimidazol-5-yl]-3,6-dihydro-2H-1,3,4-thiadiazin-2-one,
5-{2-[3-methoxy-4-(methylsulfinyl)phenyl]-1H-benzimidazol-5-yl}-6-methyl-3,6-dihydro-2H-1,3,4-thiadiazin-2-one,
5-[2-(1H-imidazol-1-yl)-1H-benzimidazol-5-yl]-6-methyl-3,6-dihydro-2H-1,3,4-thiadiazin-2-one,
5-{2-[4-(dimethylamino)phenyl]-1H-benzimidazol-5-yl}-6-methyl-3,6-dihydro-2H-1,3,4-thiadiazin-2-one,
6-methyl-5-{2-[4-(methylthio)phenyl]-1H-benzimidazol-5-yl}-3,6-dihydro-2H-1,3,4-thiadiazin-2-one,
6-methyl-5-{2-[4-(methylsulfinyl)phenyl]-1H-benzimidazol-5-yl}-3,6-dihydro-2H-1,3,4-thiadiazin-2-one,
5-[2-(2-methoxyphenyl)-1H-benzimidazol-5-yl]-6-methyl-3,6-dihydro-2H-1,3,4-thiadiazin-2-one,
5-[2-(3-methoxyphenyl)-1H-benzimidazol-5-yl]-6-methyl-3,6-dihydro-2H-1,3,4-thiadiazin-2-one,
3-methoxy-4-[5-(6-methyl-2-oxo-3,6-dihydro-2H-1,3,4-thiadiazin-5-yl)-1H-benzimidazol-2-yl]phenyl thiocyanate,
5-{2-[2-chloro-4-(methylthio)phenyl]-1H-benzimidazol-5-yl}-6-methyl-3,6-dihydro-2H-1,3,4-thiadiazin-2-one,
6-methyl-5-{2-[4-(pyrid-4-ylamino)phenyl]-1H-benzimidazol-5-yl}-3,6-dihydro-2H-1,3,4-thiadiazin-2-one,
5-[2-(4-methoxyphenyl)-1H-benzimidazol-5-yl]-3,6-dimethyl-3,6-dihydro-2H-1,3,4-thiadiazin-2-one,
3,6-dimethyl-5-[2-(1H-pyrazol-3-yl)-1H-benzimidazol-5-yl]-3,6-dihydro-2H-1,3,4-thiadiazin-2-one,
3,6-dimethyl-5-[2-(1,3-thiazol-4-yl)-1H-benzimidazol-5-yl]-3,6-dihydro-2H-1,3,4-thiadiazin-2-one,
3,6-dimethyl-5-(2-pyrid-4-yl-1H-benzimidazol-5-yl)-3,6-dihydro-2H-1,3,4-thiadiazin-2-one,
3-ethyl-6-methyl-5-[2-(1H-pyrazol-3-yl)-1H-benzimidazol-5-yl]-3,6-dihydro-2H-1,3,4-thiadiazin-2-one,
3-ethyl-6-methyl-5-[2-(1,3-thiazol-4-yl)-1H-benzimidazol-5-yl]-3,6-dihydro-2H-1,3,4-thiadiazin-2-one,
3-ethyl-5-[2-(4-methoxyphenyl)-1H-benzimidazol-5-yl]-6-methyl-3,6-dihydro-2H-1,3,4-thiadiazin-2-one,
5-[1-cycloheptyl-2-(3-methoxyphenyl)-1H-benzimidazol-5-yl]-3,6-dihydro-2H-1,3,4-thiadiazin-2-one,
5-[1-isobutyl-2-(3-methoxyphenyl)-1H-benzimidazol-5-yl]-3,6-dihydro-2H-1,3,4-thiadiazin-2-one,
5-[1-isobutyl-2-(3-methoxyphenyl)-1H-benzimidazol-5-yl]-3-(4-methylbenzyl)]-3,6-dihydro-2H-1,3,4-thiadiazin-2-one,
3-(4-tert-butylbenzyl)-5-[1-isobutyl-2-(3-methoxyphenyl)-1H-benzimidazol-5-yl]-3,6-dihydro-2H-1,3,4-thiadiazin-2-one,
3-(2-fluorobenzyl)-5-[1-isobutyl-2-(3-methoxyphenyl)-1H-benzimidazol-5-yl]-3,6-dihydro-2H-1,3,4-thiadiazin-2-one,
5-[1-cycloheptyl-2-(3-methoxyphenyl)-1H-benzimidazol-5-yl]-3-methyl]-3,6-dihydro-2H-1,3,4-thiadiazin-2-one,
5-[1-cycloheptyl-2-(3-methoxyphenyl)-1H-benzimidazol-5-yl]-3-propyl]-3,6-dihydro-2H-1,3,4-thiadiazin-2-one,
5-[1-cycloheptyl-2-(3-methoxyphenyl)-1H-benzimidazol-5-yl]-3-isobutyl]-3,6-dihydro-2H-1,3,4-thiadiazin-2-one,
5-[1-cycloheptyl-2-(3-methoxyphenyl)-1H-benzimidazol-5-yl]-3-(2-methoxy-ethyl)]-3,6-dihydro-2H-1,3,4-thiadiazin-2-one,
5-[1-isobutyl-2-(3-methoxyphenyl)-1H-benzimidazol-5-yl]-3-(3-methylbenzyl)]-3,6-dihydro-2H-1,3,4-thiadiazin-2-one,
3-(3-fluorobenzyl)-5-[1-isobutyl-2-(3-methoxyphenyl)-1H-benzimidazol-5-yl]-3,6-dihydro-2H-1,3,4-thiadiazin-2-one,
3-benzyl-5-[1-isobutyl-2-(3-mothoxyphenyl)-1H-benzimidazol-5-yl]-3,6-dihydro-2H-1,3,4-thiadiazin-2-one,
3-(4-fluorobenzyl)-5-[1-isobutyl-2-(3-methoxyphenyl)-1H-benzimidazol-5-yl]-3,6-dihydro-2H-1,3,4-thiadiazin-2-one,
3-(3-chlorobenzyl)-5-[1-isobutyl-2-(3-methoxyphenyl)-1H-benzimidazol-5-yl]-3,6-dihydro-2H-1,3,4-thiadiazin-2-one,
5-[1-isobutyl-2-(3-methoxyphenyl)-1H-benzimidazol-5-yl]-3-(3-methoxy-benzyl)]-3,6-dihydro-2H-1,3,4-thiadiazin-2-one,
5-[1-isobutyl-2-(3-methoxyphenyl)-1H-benzimidazol-5-yl]-3-(4-trifluoromethoxy-benzyl)]-3,6-dihydro-2H-1,3,4-thiadiazin-2-one,
5-[1-isobutyl-2-(3-methoxyphenyl)-1H-benzimidazol-5-yl]-3-(3-trifluoromethyl-benzyl)]-3,6-dihydro-2H-1,3,4-thiadiazin-2-one,
5-[1-isobutyl-2-(3-methoxyphenyl)-1H-benzimidazol-5-yl]-3-(4-trifluoromethyl-benzyl)]-3,6-dihydro-2H-1,3,4-thiadiazin-2-one,
3-(2,3-difluorobenzyl)-5-[1-isobutyl-2-(3-methoxyphenyl)-1H-benzimidazol-5-yl]-3,6-dihydro-2H-1,3,4-thiadiazin-2-one,
3-(2,4-difluorobenzyl)-5-[1-isobutyl-2-(3-methoxyphenyl)-1H-benzimidazol-5-yl]-3,6-dihydro-2H-1,3,4-thiadiazin-2-one,
3-(2,5-difluorobenzyl)-5-[1-isobutyl-2-(3-methoxyphenyl)-1H-benzimidazol-5-yl]-3,6-dihydro-2H-1,3,4-thiadiazin-2-one,
3-(2,6-difluorobenzyl)-5-[1-isobutyl-2-(3-methoxyphenyl)-1H-benzimidazol-5-yl]-3,6-dihydro-2H-1,3,4-thiadiazin-2-one,
3-(3,4-difluorobenzyl)-5-[1-isobutyl-2-(3-methoxyphenyl)-1H-benzimidazol-5-yl]-3,6-dihydro-2H-1,3,4-thiadiazin-2-one,
3-(3,5-dimethoxybenzyl)-5-[1-isobutyl-2-(3-methoxyphenyl)-1H-benzimidazol-5-yl]-3,6-dihydro-2H-1,3,4-thiadiazin-2-one,
3-cyclopropylmethyl-5-[1-isobutyl-2-(3-methoxyphenyl)-1H-benzimidazol-5-yl]-3,6-dihydro-2H-1,3,4-thiadiazin-2-one,
3-(2-hydroxyethyl)-5-[1-isobutyl-2-(3-methoxyphenyl)-1H-benzimidazol-5-yl]-3,6-dihydro-2H-1,3,4-thiadiazin-2-one,
3-ethyl-5-[1-isobutyl-2-(3-methoxyphenyl)-1H-benzimidazol-5-yl]-3,6-dihydro-2H-1,3,4-thiadiazin-2-one,
5-[1-Isobutyl-2-(3-methoxyphenyl)-1H-benzimidazol-5-yl]-3-propyl]-3,6-dihydro-2H-1,3,4-thiadiazin-2-one,
5-[1-isobutyl-2-(3-methoxyphenyl)-1H-benzimidazol-5-yl]-3-isopropyl]-3,6-dihydro-2H-1,3,4-thiadiazin-2-one,
2-{5-[1-isobutyl-2-(3-methoxyphenyl)-1H-benzimidazol-5-yl]-2-oxo-6H-1,3,4-thiadiazin-3-yl}acetamide,
5-[1-isobutyl-2-(3-methoxyphenyl)-1H-benzimidazol-5-yl]-3-(2-methoxyethyl)]-3,6-dihydro-2H-1,3,4-thiadiazin-2-one, {5-[1-isobutyl-2-(3-methoxyphenyl)-1H-benzimidazol-5-yl]-2-oxo-6H-1,3,4-diazin-3-yl}acetic acid,
5-[1-isobutyl-2-(3-methoxyphenyl)-1H-benzimidazol-5-yl]-6-methyl]-3,6-dihydro-2H-1,3,4-thiadiazin-2-one,
3-(2-hydroxyethyl)-5-[1-isobutyl-2-(3-methoxyphenyl)-1H-benzimidazol-5-yl]-6-methyl]-3,6-dihydro-2H-1,3,4-thiadiazin-2-one,
5-[1-isobutyl-2-(3-methoxyphenyl)-1H-benzimidazol-5-yl]-3-propyl]-3,6-dihydro-2H-1,3,4-thiadiazin-2-one,
5-[1-isobutyl-2-(3-methoxyphenyl)-1H-benzimidazol-5-yl]-3,6-dimethyl]-3,6-dihydro-2H-1,3,4-thiadiazin-2-one,
3-ethyl-5-[1-isobutyl-2-(3-methoxyphenyl)-1H-benzimidazol-5-yl]-6-methyl]-3,6-dihydro-2H-1,3,4-thiadiazin-2-one,
5-[1-isobutyl-2-(3-methoxyphenyl)-1H-benzimidazol-5-yl]-3-isopropyl-6-methyl]-3,6-dihydro-2H-1,3,4-thiadiazin-2-one,
3-cyclopropylmethyl-5-[1-isobutyl-2-(3-methoxyphenyl)-1H-benzimidazol-5-yl]-6-methyl]-3,6-dihydro-2H-1,3,4-thiadiazin-2-one,
3-ethyl-5-[2-(3-methoxyphenyl)-1-methyl-1H-benzimidazol-5-yl]-3,6-dihydro-2H-1,3,4-thiadiazin-2-one,
5-[2-(3-methoxyphenyl)-1-methyl-1H-benzimidazol-5-yl]-3-propyl]-3,6-dihydro-2H-1,3,4-thiadiazin-2-one hydrochloride,
3-cyclohexylmethyl-5-[2-(3-methoxyphenyl)-1-methyl-1H-benzimidazol-5-yl]-3,6-dihydro-2H-1,3,4-thiadiazin-2-one,
3-[2-(4-fluorophenoxy)ethyl]-5-[2-(3-methoxyphenyl)-1-methyl-1H-benzimidazol-5-yl]-3,6-dihydro-2H-1,3,4-thiadiazin-2-one,
5-[2-(3-methoxyphenyl)-1-methyl-1H-benzimidazol-5-yl]-3-methyl]-3,6-dihydro-2H-1,3,4-thiadiazin-2-one,
3-isopropyl-5-[2-(3-methoxyphenyl)-1-methyl-1H-benzimidazol-5-yl]-3,6-dihydro-2H-1,3,4-thiadiazin-2-one,
3-isobutyl-5-[2-(3-methoxyphenyl)-1-methyl-1H-benzimidazol-5-yl]-3,6-dihydro-2H-1,3,4-thiadiazin-2-one,
3-cyclopropylmethyl-5-[2-(3-methoxyphenyl)-1-methyl-1H-benzimidazol-5-yl]-3,6-dihydro-2H-1,3,4-thiadiazin-2-one,
5-[2-(3-methoxyphenyl)-1-methyl-1H-benzimidazol-5-yl]-6-methyl]-3,6-dihydro-2H-1,3,4-thiadiazin-2-one,
3-ethyl-5-[2-(3-methoxyphenyl)-1-methyl-1H-benzimidazol-5-yl]-6-methyl]-3,6-dihydro-2H-1,3,4-thiadiazin-2-one,
5-[2-(3-methoxyphenyl)-1-methyl-1H-benzimidazol-5-yl]-6-methyl-3-propyl]-3,6-dihydro-2H-1,3,4-thiadiazin-2-one,
5-[2-(3-methoxyphenyl)-1-methyl-1H-benzimidazol-5-yl]-6-methyl-3-(2-piperidin-1-ylethyl)]-3,6-dihydro-2H-1,3,4-thiadiazin-2-one,
3-isobutyl-5-[2-(3-methoxyphenyl)-1-methyl-1H-benzimidazol-5-yl]-6-methyl]-3,6-dihydro-2H-1,3,4-thiadiazin-2-one,
5-[2-(3-methoxyphenyl)-1-methyl-1H-benzimidazol-5-yl]-3,6-dimethyl]-3,6-dihydro-2H-1,3,4-thiadiazin-2-one,
6-methyl-5-[1-methyl-2-(3-trifluoromethylphenyl)-1H-benzimidazol-5-yl]-3,6-dihydro-2H-1,3,4-thiadiazin-2-one,
3-benzyl-6-methyl-5-[1-methyl-2-(3-trifluoromethylphenyl)-1H-benzimidazol-5-yl]-3,6-dihydro-2H-1,3,4-thiadiazin-2-one,
3-cyclopropylmethyl-6-methyl-5-[1-methyl-2-(3-trifluoromethylphenyl)-1H-benzimidazol-5-yl]-3,6-dihydro-2H-1,3,4-thiadiazin-2-one,
3-isopropyl-6-methyl-5-[1-methyl-2-(3-trifluoromethylphenyl)-1H-benzimidazol-5-yl]-3,6-dihydro-2H-1,3,4-thiadiazin-2-one,
3,6-dimethyl-5-[1-methyl-2-(3-trifluoromethylphenyl)-1H-benzimidazol-5-yl]-3,6-dihydro-2H-1,3,4-thiadiazin-2-one,
3-ethyl-6-methyl-5-[1-methyl-2-(3-trifluoromethylphenyl)-1H-benzimidazol-5-yl]-1,3,4-thiadiazin-2-one,
5-[1-benzyl-2-(1-methyl-1H-pyrrol-2-yl)-1H-benzimidazol-5-yl]-6-methyl]-3,6-dihydro-2H-1,3,4-thiadiazin-2-one,
5-[1-benzyl-2-(1-methyl-1H-imidazol-2-yl)-1H-benzimidazol-5-yl]-6-methyl]-3,6-dihydro-2H-1,3,4-thiadiazin-2-one,
5-(1-benzyl-2-thiophen-2-yl-1H-benzimidazol-5-yl)-6-methyl]-3,6-dihydro-2H-1,3,4-thiadiazin-2-one,
5-[1-benzyl-2-(3-methoxyphenyl)-1H-benzimidazol-5-yl]-6-methyl]-3,6-dihydro-2H-1,3,4-thiadiazin-2-one,
5-[1-benzyl-2-(4-methoxyphenyl)-1H-benzimidazol-5-yl]-6-methyl]-3,6-dihydro-2H-1,3,4-thiadiazin-2-one,
5-[1-benzyl-2-(3-hydroxy-4-methoxyphenyl)-1H-benzimidazol-5-yl]-6-methyl]-3,6-dihydro-2H-1,3,4-thiadiazin-2-one,
5-[1-benzyl-2-(2,4-dihydroxyphenyl)-1H-benzimidazol-5-yl]-6-methyl]-3,6-dihydro-2H-1,3,4-thiadiazin-2-one,
5-[1-benzyl-2-(3,4-dihydroxyphenyl)-1H-benzimidazol-5-yl]-6-methyl]-3,6-dihydro-2H-1,3,4-thiadiazin-2-one,
5-[1-benzyl-2-(3,4,5-trihydroxyphenyl)-1H-benzimidazol-5-yl)-6-methyl)-3,6-dihydro-2H-1,3,4-thiadiazin-2-one,
6-methyl-5-[1-methyl-2-(1-methyl-1H-pyrrol-2-yl)-1H-benzimidazol-5-yl]-3,6-dihydro-2H-1,3,4-thiadiazin-2-one,
5-[2-(1H-imidazol-4-yl)-1-methyl-1H-benzimidazol-5-yl]-6-methyl]-3,6-dihydro-2H-1,3,4-thiadiazin-2-one,
5-[2-(1H-imidazol-2-yl)-1-methyl-1H-benzimidazol-5-yl]-6-methyl]-3,6-dihydro-2H-1,3,4-thiadiazin-2-one,
6-methyl-5-[1-methyl-2-(5-methyl-3H-imidazol-4-yl)-1H-benzimidazol-5-yl]-3,6-dihydro-2H-1,3,4-thiadiazin-2-one,
6-methyl-5-[1-methyl-2-(1-methyl-1H-imidazol-2-yl)-1H-benzimidazol-5-yl]-3,6-dihydro-2H-1,3,4-thiadiazin-2-one,
6-methyl-5-(1-methyl-2-thiophen-2-yl-1H-benzimidazol-5-yl)]-3,6-dihydro-2H-1,3,4-thiadiazin-2-one,
6-methyl-5-(1-methyl-2-thiophen-3-yl-1H-benzimidazol-5-yl)]-3,6-dihydro-2H-1,3,4-thiadiazin-2-one,
5-[2-(2-methoxyphenyl)-1-methyl-1H-benzimidazol-5-yl]-6-methyl]-3,6-dihydro-2H-1,3,4-thiadiazin-2-one,
5-[2-(4-methoxyphenyl)-1-methyl-1H-benzimidazol-5-yl]-6-methyl]-3,6-dihydro-2H-1,3,4-thiadiazin-2-one,
5-[2-(3-hydroxy-4-methoxyphenyl)-1-methyl-1H-benzimidazol-5-yl]-6-methyl]-3,6-dihydro-2H-1,3,4-thiadiazin-2-one,
5-[2-(3,4-dihydroxyphenyl)-1-methyl-1H-benzimidazol-5-yl]-6-methyl]-3,6-dihydro-2H-1,3,4-thiadiazin-2-one,
6-methyl-5-[1-methyl-2-(3,4,5-trihydroxyphenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-(3-methylbenzyl)-3,6-dihydro-2H-1,3,4-thiadiazin-2-one,
5-[1-ethyl-2-(3-fluorophenyl)-1H-benzimidazol-5-yl]-3-(4-methylbenzyl)]-3,6-dihydro-2H-1,3,4-thiadiazin-2-one,
3-(4-tert-butylbenzyl)-5-[1-ethyl-2-(3-fluorophenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-(2-fluorobenzyl)-3,6-dihydro-2H-1,3,4-thiadiazin-2-one,
5-[1-ethyl-2-(3-fluorophenyl)-1H-benzimidazol-5-yl]-3-(3-fluorobenzyl)-3,6-dihydro-2H-1,3,4-thiadiazin-2-one,
3-benzyl-5-[1-ethyl-2-(3-fluorophenyl)-1H-benzimidazol-5-yl]-3,6-dihydro-2H-1,3,4-thiadiazin-2-one, 3-(3-chlorobenzyl)-5-[1-ethyl-2-(3-fluorophenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-methyl]-3,6-dihydro-2H-1,3,4-thiadiazin-2-one,
3-cyclohexylmethyl-5-[1-ethyl-2-(3-fluorophenyl)-1H-benzimidazol-5-yl]-3,6-dihydro-2H-1,3,4-thiadiazin-2-one,
3-(2-dimethylaminoethyl)-5-[1-ethyl-2-(3-fluorophenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-(2-pyrrolidin-1-ylethyl)]-3,6-dihydro-2H-1,3,4-thiadiazin-2-one,
5-[1-isobutyl-2-(3-methoxyphenyl)-1H-benzimidazol-5-yl]-3-(3-methylbenzyl)]-3,6-dihydro-2H-1,3,4-thiadiazin-2-one,
5-[2-(4-methoxyphenyl)-1H-benzimidazol-5-yl]-6-methyl]-3,6-dihydro-2H-1,3,4-thiadiazin-2-one,
3-(2-dimethylaminoethyl)-6-methyl-5-[1-methyl-2-(3-trifluoromethylphenyl)-1H-benzimidazol-5-yl]-3,6-dihydro-2H-1,3,4-thiadiazin-2-one
6-methyl-5-[1-methyl-2-(3-trifluoromethylphenyl)-1H-benzimidazol-5-yl]-3-(2-piperidin-1-ylethyl)]-3,6-dihydro-2H1,3,4-thiadiazin-2-one,
3-cyclohexylmethyl-6-methyl-5-[1-methyl-2-(3-trifluoromethylphenyl)-1H-benzimidazol-5-yl]-3,6-dihydro-2H-1,3,4-thiadiazin-2-one,
6-methyl-5-[1-methyl-2-(3-trifluoromethylphenyl)-1H-benzimidazol-5-yl]-3-(2-morpholin-4-ylethyl)]-3,6-dihydro-2H-1,3,4-thiadiazin-2-one,
6-methyl-5-[1-methyl-2-(3-trifluoromethylphenyl)-1H-benzimidazol-5-yl]-3-(2-pyrrolidin-1-ylethyl)]-3,6-dihydro-2H-1,3,4-thiadiazin-2-one,
2-{6-methyl-5-[1-methyl-2-(3-trifluoromethylphenyl)-1H-benzimidazol-5-yl]-2-oxo-6H-1,3,4-thiadiazin-3-yl}acetamide,
3-(2-methoxyethyl)-6-methyl-5-[1-methyl-2-(3-trifluoromethylphenyl)-1H-benzimidazol-5-yl]-3,6-dihydro-2H-1,3,4-thiadiazin-2-one,
5-[2-(3-fluorophenyl)-1-methyl-1H-benzimidazol-5-yl]-3-(2-hydroxyethyl)-6-methyl]-3,6-dihydro-2H-1,3,4-thiadiazin-2-one,
3-cyclohexylmethyl-5-[2-(3-fluorophenyl)-1-methyl-1H-benzimidazol-5-yl]-6-methyl]-3,6-dihydro-2H-1,3,4-thiadiazin-2-one,
2-{5-[2-(3-fluorophenyl)-1-methyl-1H-benzimidazol-5-yl]-6-methyl-2-oxo-6H-1,3,4-thiadiazin-3-yl}acetamide,
3-[2-(4-fluorophenoxy)ethyl]-5-[2-(3-fluorophenyl)-1-methyl-1H-benzimidazol-5-yl]-6-methyl]-3,6-dihydro-2H-1,3,4-thiadiazin-2-one,
5-[2-(3-fluorophenyl)-1-methyl-1H-benzimidazol-5-yl]-3-isopropyl-6-methyl-3,6-dihydro-2H-1,3,4-thiadiazin-2-one,
5-[2-(3-fluorophenyl)-1-methyl-1H-benzimidazol-5-yl]-3-isobutyl-6-methyl]-3,6-dihydro-2H-1,3,4-thiadiazin-2-one,
ethyl 4-{5-[2-(3-fluorophenyl)-1-methyl-1H-benzimidazol-5-yl]-6-methyl-2-oxo-6H-1,3,4-thiadiazin-3-yl}butyrate,
ethyl 3-{5-[2-(3-fluorophenyl)-1-methyl-1H-benzimidazol-5-yl]-6-methyl-2-oxo-6H-1,3,4-thiadiazin-3-yl}propionate,
3-cyclopropylmethyl-5-[2-(3-fluorophenyl)-1-methyl-1H-benzimidazol-5-yl]-6-methyl]-3,6-dihydro-2H-1,3,4-thiadiazin-2-one,
5-[2-(3-fluorophenyl)-1-methyl-1H-benzimidazol-5-yl]-3-(2-methoxyethyl)-6-methyl]-3,6-dihydro-2H-1,3,4-thiadiazin-2-one,
3-benzyl-5-[2-(3-fluorophenyl)-1-methyl-1H-benzimidazol-5-yl]-6-methyl]-3,6-dihydro-2H-1,3,4-thiadiazin-2-one,
ethyl {5-[2-(3-fluorophenyl)-1-methyl-1H-benzimidazol-5-yl]-6-methyl-2-oxo-6H-1,3,4-thiadiazin-3-yl}acetate,
5-[2-(3-fluorophenyl)-1-methyl-1H-benzimidazol-5-yl]-6-methyl-3-propyl]-3,6-dihydro-2H-1,3,4-thiadiazin-2-one,
5-[2-(3-fluorophenyl)-1-methyl-1H-benzimidazol-5-yl]-6-methyl-3-(2-morpholin-4-ylethyl)]-3,6-dihydro-2H-1,3,4-thiadiazin-2-one
5-[2-(3-fluorophenyl)-1-methyl-1H-benzimidazol-5-yl]-6-methyl-3-(2-piperidin-1-ylethyl)]-3,6-dihydro-2H-1,3,4-thiadiazin-2-one,
5-[2-(3-fluorophenyl)-1-methyl-1H-benzimidazol-5-yl]-6-methyl]-3,6-dihydro-2H-1,3,4-thiadiazin-2-one,
3-cyclohexylmethyl-5-[2-(3-fluorophenyl)-1-methyl-1H-benzimidazol-5-yl]-3,6-dihydro-2H-1,3,4-thiadiazin-2-one,
2-{5-[2-(3-fluorophenyl)-1-methyl-1H-benzimidazol-5]-yl]-2-oxo-6H-1,3,4-thiadiazin-3-yl}acetamide,
3-[2-(4-fluorophenoxy)ethyl]-5-[2-(3-fluorophenyl)-1-methyl-1H-benzimidazol-5-yl]-3,6-dihydro-2H-1,3,4-thiadiazin-2-one,
5-[2-(3-fluorophenyl)-1-methyl-1H-benzimidazol-5-yl]-3-isopropyl-3,6-dihydro-2H-1,3,4-thiadiazin-2-one,
5-[2-(3-fluorophenyl)-1-methyl-1H-benzimidazol-5-yl]-3-isobutyl-3,6-dihydro-2H-1,3,4-thiadiazin-2-one,
3-cyclopropylmethyl-5-[2-(3-fluorophenyl)-1-methyl-1H-benzimidazol-5-yl]-3,6-dihydro-2H-1,3,4-thiadiazin-2-one
5-[2-(3-fluorophenyl)-1-methyl-1H-benzimidazol-5-yl]-3-(2-methoxyethyl)]-3,6-dihydro-2H-1,3,4-thiadiazin-2-one,
3-benzyl-5-[2-(3-fluorophenyl)-1-methyl-1H-benzimidazol-5-yl]-3,6-dihydro-2H-1,3,4-thiadiazin-2-one,
ethyl {5-[2-(3-fluorophenyl)-1-methyl-1H-benzimidazol-5-yl]-2-oxo-6H-1,3,4-thiadiazin-3-yl}acetate,
5-[2-(3-fluorophenyl)-1-methyl-1H-benzimidazol-5-yl]-3-(2-piperidin-1-ylethyl)]-3,6-dihydro-2H-1,3,4-thiadiazin-2-one,
5-[2-(3-fluorophenyl)-1-methyl-1H-benzimidazol-5-yl]-3,6-dihydro-2H-1,3,4-thiadiazin-2-one,
5-[2-(3-fluorophenyl)-1-methyl-1H-benzimidazol-5-yl]-3-propyl]-3,6-dihydro-2H-1,3,4-thiadiazin-2-one,
5-(1-benzyl-2-thiophen-3-yl-1H-benzimidazol-5-yl)-6-methyl]-3,6-dihydro-2H-1,3,4-thiadiazin-2-one,
5-[1-benzyl-2-(2-methoxyphenyl)-1H-benzimidazol-5-yl]-6-methyl]-3,6-dihydro-2H-1,3,4-thiadiazin-2-one,
5-[1-cyclopropylmethyl-2-(3-methoxyphenyl)-1H-benzimidazol-5-yl]-6-methyl]-3,6-dihydro-2H-1,3,4-thiadiazin-2-one,
3-cyclohexylmethyl-5-(2-furan-2-yl-1-methyl-1H-benzimidazol-5-yl)]-3,6-dihydro-2H-1,3,4-thiadiazin-2-one,
3-benzyl-5-(2-furan-2-yl-1-methyl-1H-benzimidazol-5-yl)]-3,6-dihydro-2H-1,3,4-thiadiazin-2-one,
3-cyclopropylmethyl-5-(2-furan-2-yl-1-methyl-1H-benzimidazol-5-yl)]-3,6-dihydro-2H-1,3,4-thiadiazin-2-one,
5-(2-furan-2-yl-1-methyl-1H-benzimidazol-5-yl)-3-methyl]-3,6-dihydro-2H-1,3,4-thiadiazin-2-one,
3-ethyl-5-(2-furan-2-yl-1-methyl-1H-benzimidazol-5-yl)]-3,6-dihydro-2H-1,3,4-thiadiazin-2-one,
5-(2-furan-2-yl-1-methyl-1H-benzimidazol-5-yl)-3-(2-piperidin-1-ylethyl)]-3,6-dihydro-2H-1,3,4-thiadiazin-2-one,
5-(2-furan-2-yl-1-methyl-1H-benzimidazol-5-yl)-3-(2-pyrrolidin-1-ylethyl)]-3,6-dihydro-2H-1,3,4-thiadiazin-2-one, 5-(2-furan-2-yl-1-methyl-1H-benzimidazol-5-yl)-3-isobutyl]-3,6-dihydro-2H-1,3,4-thiadiazin-2-one,
5-(2-furan-2-yl-1-methyl-1H-benzimidazol-5-yl)]-3,6-dihydro-2H-1,3,4-thiadiazin-2-one,
2-{5-[2-(3-methoxyphenyl)-1-methyl-1H-benzimidazol-5-yl]-6-methyl-2-oxo-6H-1,3,4-thiadiazin-3-yl}acetamide,
3-isopropyl-5-[2-(3-methoxyphenyl)-1-methyl-1H-benzimidazol-5-yl]-6-methyl]-3,6-dihydro-2H-1,3,4-thiadiazin-2-one,
3-(4-tert-butylbenzyl)-5-[1-methyl-2-(3-trifluoromethylphenyl)-1H-benzimidazol-5-yl]-3,6-dihydro-2H-1,3,4-thiadiazin-2-one,
3-(4-fluorobenzyl)-5-[1-methyl-2-(3-trifluoromethylphenyl)-1H-benzimidazol-5-yl]-3,6-dihydro-2H-1,3,4-thiadiazin-2-one,
5-[1-methyl-2-(3-trifluoromethylphenyl)-1H-benzimidazol-5-yl]-3-(4-trifluoro-methoxybenzyl)]-3,6-dihydro-2H-1,3,4-thiadiazin-2-one,
5-[1-methyl-2-(3-trifluoromethylphenyl)-1H-benzimidazol-5-yl]-3-(4-trifluoro-methylbenzyl)]-3,6-dihydro-2H-1,3,4-thiadiazin-2-one,
3-{5-[1-methyl-2-(3-trifluoromethylphenyl)-1H-benzimidazol-5-yl]-2-oxo-6H-1,3,4-thiadiazin-3-ylmethyl}benzonitrile,
3-(4-methanesulfonylbenzyl)-5-[1-methyl-2-(3-trifluoromethylphenyl)-1H-benzimidazol-5-yl]-3,6-dihydro-2H-1,3,4-thiadiazin-2-one,
3-(3,5-dimethoxybenzyl)-5-[1-methyl-2-(3-trifluoromethylphenyl)-1H-benzimidazol-5-yl]-3,6-dihydro-2H-1,3,4-thiadiazin-2-one,
5-[1-methyl-2-(3-trifluoromethylphenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-(4-fluorobenzyl)]-3,6-dihydro-2H-1,3,4-thiadiazin-2-one,
5-[1-ethyl-2-(3-fluorophenyl)-1H-benzimidazol-5-yl]-3-(3-methoxybenzyl)]-3,6-dihydro-2H-1,3,4-thiadiazin-2-one,
5-[1-ethyl-2-(3-fluorophenyl)-1H-benzimidazol-5-yl]-3-(4-trifluoromethoxy-benzyl)]-3,6-dihydro-2H-1,3,4-thiadiazin-2-one,
2-{5-[1-ethyl-2-(3-fluorophenyl)-1H-benzimidazol-5-yl]-2-oxo-6H-1,3,4-thiadiazin-3-yl}acetamide,
3-cyclopropylmethyl-5-[1-ethyl-2-(3-fluorophenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-isopropyl]-3,6-dihydro-2H-1,3,4-thiadiazin-2-one
3-ethyl-5-[1-ethyl-2-(3-fluorophenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-propyl]-3,6-dihydro-2H-1,3,4-thiadiazin-2-one,
5-[1-ethyl-2-(3-fluorophenyl)-1H-benzimidazol-5-yl]-3-(2-methoxyethyl)]-3,6-dihydro-2H-1,3,4-thiadiazin-2-one,
{5-[1-ethyl-2-(3-fluorophenyl)-1H-benzimidazol-5-yl]-2-oxo-6H-1-1,3,4-thiadiazin-3-yl}acetic acid,
5-[1-ethyl-2-(3-fluorophenyl)-1H-benzimidazol-5-yl]-3-(2-hydroxyethyl))-3,6-dihydro-2H-1,3,4-thiadiazin-2-one,
5-[1-ethyl-2-(3-fluorophenyl)-1H-benzimidazol-5-yl]-3-(3-hydroxypropyl)]-3,6-dihydro-2H-1,3,4-thiadiazin-2-one,
3-(2-aminoethyl)-5-[1-ethyl-2-(3-fluorophenyl)-1H-benzimidazol-5-yl]-3,6-dihydro-2H-1,3,4-thiadiazin-2-one,
3-(3-aminopropyl)-5-[1-ethyl-2-(3-fluorophenyl)-1H-benzimidazol-5-yl]-3,6-dihydro-2H-1,3,4-thiadiazin-2-one,
3-benzyl-5-[1-ethyl-2-(3-methoxyphenyl)-1H-benzimidazol-5-yl]-3,6-dihydro-2H-1,3,4-thiadiazin-2-one,
5-[1-ethyl-2-(3-methoxyphenyl)-1H-benzimidazol-5-yl]-3-(4-methylbenzyl))-3,6-dihydro-2H-1,3,4-thiadiazin-2-one,
5-[1-ethyl-2-(3-methoxyphenyl)-1H-benzimidazol-5-yl]-3-(2-fluorobenzyl)]-3,6-dihydro-2H-1,3,4-thiadiazin-2-one,
3-benzyl-5-[1-methyl-2-(3-trifluoromethylphenyl)-1H-benzimidazol-5-yl]-3,6-dihydro-2H-1,3,4-thiadiazin-2-one,
3-methyl-5-[1-methyl-2-(3-trifluoromethylphenyl)-1H-benzimidazol-5-yl]-3,6-dihydro-2H-1,3,4-thiadiazin-2-one,
3-cyclohexylmethyl-5-[1-methyl-2-(3-trifluoromethylphenyl)-1H-benzimidazol-5-yl]-3,6-dihydro-2H-1,3,4-thiadiazin-2-one,
3-(3-aminopropyl)-5-[1-methyl-2-(3-trifluoromethylphenyl)-1H-benzimidazol-5-yl]-3,6-dihydro-2H-1,3,4-thiadiazin-2-one,
3-(2-aminoethyl)-5-[1-methyl-2-(3-trifluoromethylphenyl)-1H-benzimidazol-5-yl]-3,6-dihydro-2H-1,3,4-thiadiazin-2-one,
3-(2-aminoethyl)-5-[1-ethyl-2-(3-methoxyphenyl)-1H-benzimidazol-5-yl]-3,6-dihydro-2H-1,3,4-thiadiazin-2-one,
3-(3-aminopropyl)-5-[1-ethyl-2-(3-methoxyphenyl)-1H-benzimidazol-5-yl]-3,6-dihydro-2H-1,3,4-thiadiazin-2-one,
5-[1-ethyl-2-(3-methoxyphenyl)-1H-benzimidazol-5-yl]-3-(2-hydroxyethyl))-3,6-dihydro-2H-1,3,4-thiadiazin-2-one
5-[1-ethyl-2-(3-methoxyphenyl)-1H-benzimidazol-5-yl]-3-(3-hydroxypropyl)]-3,6-dihydro-2H-1,3,4-thiadiazin-2-one,
N-(2-{5-[1-methyl-2-(3-trifluoromethylphenyl)-1H-benzimidazol-5-yl]-2-oxo-6H-1,3,4-thiadiazin-3-yl}ethyl)acetamide,
furan-2-carboxylic acid (2-{5-[1-methyl-2-(3-trifluoromethylphenyl)-1H-benzimidazol-5-yl]-2-oxo-6H-1,3,4-thiadiazin-3-yl}ethyl)amide,
N-(2-{5-[1-methyl-2-(3-trifluoromethylphenyl)-1H-benzimidazol-5-yl]-2-oxo-6H-1,3,4-thiadiazin-3-yl}ethyl) isobutyramide,
cyclopentanecarboxylic acid (2-{5-[1-methyl-2-(3-trifluoromethylphenyl)-1H-benzimidazol-5-yl]-2-oxo-6H-1,3,4-thiadiazin-3-yl}ethyl)amide,
N-(2-{5-[1-methyl-2-(3-trifluoromethylphenyl)-1H-benzimidazol-5-yl]-2-oxo-6H-1,3,4-thiadiazin-3-yl}ethyl) benzamide,
N-(2-{5-[1-methyl-2-(3-trifluoromethylphenyl)-1H-benzimidazol-5-yl]-2-oxo-6H-1,3,4-thiadiazin-3-yl}ethyl) methanesulfonamide,
N-(2-{5-[1-methyl-2-(3-trifluoromethylphenyl)-1H-benzimidazol-5-yl]-2-oxo-6H-1,3,4-thiadiazin-3-yl}ethyl) benzenesulfonamide,
5-[1-methyl-2-(3-trifluoromethylphenyl)-1H-benzimidazol-5-yl]-6-propyl]-3,6-dihydro-2H-1,3,4-thiadiazin-2-one,
3-ethyl-5-[1-methyl-2-(3-trifluoromethylphenyl)-1H-benzimidazol-5-yl]-6-propyl]-3,6-dihydro-2H-1,3,4-thiadiazin-2-one,
5-[1-methyl-2-(3-trifluoromethylphenyl)-1H-benzimidazol-5-yl]-3,6-dipropyl]-3,6-dihydro-2H-1,3,4-thiadiazin-2-one,
3-benzyl-5-[1-methyl-2-(3-trifluoromethylphenyl)-1H-benzimidazol-5-yl]-6-propyl]-3,6-dihydro-2H-1,3,4-thiadiazin-2-one,
3-cyclopropylmethyl-5-[1-methyl-2-(3-trifluoromethylphenyl)-1H-benzimidazol-5-yl]-6-propyl]-3,6-dihydro-2H-1,3,4-thiadiazin-2-one,
3-isopropyl-5-[1-methyl-2-(3-trifluoromethylphenyl)-1H-benzimidazol-5-yl]-6-propyl]-3,6-dihydro-2H-1,3,4-thiadiazin-2-one, 3-isobutyl-5-[1-methyl-2-(3-trifluoromethylphenyl)-1H-benzimidazol-5-yl]-6-propyl]-3,6-dihydro-2H-1,3,4-thiadiazin-2-one,
5-[1-methyl-2-(3-trifluoromethylphenyl)-1H-benzimidazol-5-yl]-3-(2-piperidin-1-ylethyl)-6-propyl]-3,6-dihydro-2H-1,3,4-thiadiazin-2-one,
5-[1-methyl-2-(3-trifluoromethylphenyl)-1H-benzimidazol-5-yl]-6-propyl-3-(2-pyrrolidin-1-ylethyl)]-3,6-dihydro-2H-1,3,4-thiadiazin-2-one,
1-(2-{5-[1-methyl-2-(3-trifluoromethylphenyl)-1H-benzimidazol-5-yl]-2-oxo-6H-1,3,4-thiadiazin-3-yl}ethyl)-3-phenylurea,
1-ethyl-3-(2-{5-[1-methyl-2-(3-trifluoromethylphenyl)-1H-benzimidazol-5-yl]-2-oxo-6H-1,3,4-thiadiazin-3-yl}ethyl)urea,
5-[1-ethyl-2-(3-methoxyphenyl)-1H-benzimidazol-5-yl]-3,6-dihydro-2H-1,3,4-thiadiazin-2-one,
3-cyclopropylmethyl-5-[1-methyl-2-(3-trifluoromethylphenyl)-1H-benzimidazol-5-yl]-3,6-dihydro-2H-1,3,4-thiadiazin-2-one,
butane-1-sulfonic acid (2-{5-[1-methyl-2-(3-trifluoromethylphenyl)-1H-benzimidazol-5-yl]-2-oxo-6H-1,3,4-thiadiazin-3-yl}ethyl)amide,
N-{2-[5-(2-furan-2-yl-1-methyl-1H-benzimidazol-5-yl)-2-oxo-6H-1,3,4-thiadiazin-3-yl]ethyl}acetamide,
N-{2-[5-(2-furan-2-yl-1-methyl-1H-benzimidazol-5-yl)-2-oxo-6H-1,3,4-thiadiazin-3-yl]ethyl}isobutyramide,
cyclopentanecarboxylic acid {2-[5-(2-furan-2-yl-1-methyl-1H-benzimidazol-5-yl)-2-oxo-6H-1,3,4-thiadiazin-3-yl]ethyl}amide,
N-{2-[5-(2-furan-2-yl-1-methyl-1H-benzimidazol-5-yl)-2-oxo-6H-1,3,4-thiadiazin-3-yl]ethyl}benzamide,
N-{2-[5-(2-furan-2-yl-1-methyl-1H-benzimidazol-5-yl)-2-oxo-6H-1,3,4-thiadiazin-3-yl]ethyl}nicotinamide,
cyclopropanecarboxylic acid {2-[5-(2-furan-2-yl-1-methyl-1H-1-benzimidazol-5-yl)-2-oxo-6H-1,3,4-thiadiazin-3-yl]ethyl}amide,
3-fluoro-N-{2-[5-(2-furan-2-yl-1-methyl-1H-benzimidazol-5-yl)-2-oxo-6H-1,3,4-thiadiazin-3-yl]ethyl}benzamide,
N-{2-[5-(2-furan-2-yl-1-methyl-1H-benzimidazol-5-yl)-2-oxo-6H-1,3,4-thiadiazin-3-yl]ethyl}-4-methylbenzamide,
3-(2-aminoethyl)-5-(2-furan-2-yl-1-methyl-1H-benzimidazol-5-yl)]-3,6-dihydro-2H-1,3,4-thiadiazin-2-one,
N-{2-[5-(2-furan-2-yl-1-methyl-1H-benzimidazol-5-yl)-2-oxo-6H-1,3,4-thiadiazin-3-yl]ethyl}benzenesulfonamide,
butane-1-sulfonic acid {2-[5-(2-furan-2-yl-1-methyl-1H-benzimidazol-5-yl)-2-oxo-6H-1,3,4-thiadiazin-3-yl]ethyl}amide,
1-{2-[5-(2-furan-2-yl-1-methyl-1H-benzimidazol-5-yl)-2-oxo-6H-1,3,4-thiadiazin-3-yl]ethyl}-3-isopropylurea,
1-{2-[5-(2-furan-2-yl-1-methyl-1H-benzimidazol-5-yl)-2-oxo-6H-1,3,4-thiadiazin-3-yl]ethyl}-3-phenylurea,
1-cyclopentyl-3-{2-[5-(2-furan-2-yl-1-methyl-1H-benzimidazol-5-yl)-2-oxo-6H-1,3,4-thiadiazin-3-yl]ethyl}urea,
1-ethyl-3-{2-[5-(2-furan-2-yl-1-methyl-1H-benzimidazol-5-yl)-2-oxo-6H-1,3,4-thiadiazin-3-yl]ethyl}urea,
1-benzyl-3-{2-[5-(2-furan-2-yl-1-methyl-1H-benzimidazol-5-yl)-2-oxo-6H-1,3,4-thiadiazin-3-yl]ethyl}urea,
1-(4-fluorobenzyl)-3-{2-[5-(2-furan-2-yl-1-methyl-1H-benzimidazol-5-yl)-2-oxo-6H-1,3,4-thiadiazin-3-yl]ethyl}urea,
1-(4-acetylphenyl)-3-{2-[5-(2-furan-2-yl-1-methyl-1H-benzimidazol-5-yl)-2-oxo-6H-1,3,4-thiadiazin-3-yl]ethyl}urea,
1-{2-[5-(2-furan-2-yl-1-methyl-1H-benzimidazol-5-yl)-2-oxo-6H-1,3,4-thiadiazin-3-yl]ethyl}-3-p-tolylurea,
1-butyl-3-{2-[5-(2-furan-2-yl-1-methyl-1H-benzimidazol-5-yl)-2-oxo-6H-1,3,4-thiadiazin-3-yl]ethyl}urea,
N-{3-[5-(2-furan-2-yl-1-methyl-1H-benzimidazol-5-yl)-2-oxo-6H-1,3,4-thiadiazin-3-yl]propyl}benzamide,
cyclopropanecarboxylic acid {3-[5-(2-furan-2-yl-1-methyl-1H-benzimidazol-5-yl)-2-oxo-6H-1,3,4-thiadiazin-3yl]propyl}amide,
1-(4-chlorophenyl)-3-{2-[5-(2-furan-2-yl-1-methyl-1H-benzimidazol-5-yl)-2-oxo-6H-1,3,4-thiadiazin-3-yl]ethyl}urea,
1-(4-chlorophenyl)-3-{3-[5-(2-furan-2-yl-1-methyl-1H-benzimidazol-5-yl)-2-oxo-6H-1,3,4-thiadiazin-3-yl]propyl}urea,
1-butyl-3-{3-[5-(2-furan-2-yl-1-methyl-1H-benzimidazol-5-yl)-2-oxo-6H-1,3,4-thiadiazin-3-yl]propyl}urea,
1-benzyl-3-{3-[5-(2-furan-2-yl-1-methyl-1H-benzimidazol-5-yl)-2-oxo-6H-1,3,4-thiadiazin-3-yl]propyl}urea,
1-(3-fluorophenyl)-3-{3-[5-(2-furan-2-yl-1-methyl-1H-benzimidazol-5-yl)-2-oxo-6H-1,3,4-thiadiazin-3-yl]propyl}urea
N-{2-[5-(2-furan-2-yl-1-methyl-1H-benzimidazol-5-yl)-2-oxo-6H-1,3,4-thiadiazin-3-yl]ethyl}methanesulfonamide,
5-(2-furan-2-yl-1-methyl-1H-benzimidazol-5-yl)-3-(2-methoxyethyl)]-3,6-dihydro-2H-1,3,4-thiadiazin-2-one,
5-(2-furan-2-yl-1-methyl-1H-benzimidazol-5-yl)-3-(3-hydroxypropyl)]-3,6-dihydro-2H-1,3,4-thiadiazin-2-one,
5-(2-furan-2-yl-1-methyl-1H-benzimidazol-5-yl)-3-(2-hydroxyethyl)]-3,6-dihydro-2H-1,3,4-thiadiazin-2-one,
3-(3-aminopropyl)-5-(2-furan-2-yl-1-methyl-1H-benzimidazol-5-yl)]-3,6-dihydro-2H-1,3,4-thiadiazin-2-one,
3-(2-aminoethyl)-5-[2-(3-fluorophenyl)-1-methyl-1H-benzimidazol-5-yl]-6-methyl]-3,6-dihydro-2H-1,3,4-thiadiazin-2-one,
N-(2-{5-[2-(3-fluorophenyl)-1-methyl-1H-benzimidazol-5-yl]-6-methyl-2-oxo-6H-1,3,4-thiadiazin-3-yl}ethyl)-2-phenylacetamide,
N-(2-{5-[2-(3-fluorophenyl)-1-methyl-1H-benzimidazol-5-yl]-6-methyl-2-oxo-6H-1,3,4-thiadiazin-3-yl}ethyl)-4-methylbenzamide,
cyclopropanecarboxylic acid (2-{5-[2-(3-fluorophenyl)-1-methyl-1H-benzimidazol-5-yl]-6-methyl-2-oxo-6H-1,3,4-thiadiazin-3-yl}ethyl)amide,
cyclopentanecarboxylic acid (2-{5-[2-(3-fluorophenyl)-1-methyl-1H-benzimidazol-5-yl]-6-methyl-2-oxo-6H-1,3,4-thiadiazin-3-yl}ethyl)amide,
N-(2-{5-[2-(3-fluorophenyl)-1-methyl-1H-benzimidazol-5-yl]-6-methyl-2-oxo-6H-1,3,4-thiadiazin-3-yl}ethyl)-2-methoxyacetamide,
N-(2-{5-[2-(3-fluorophenyl)-1-methyl-1H-benzimidazol-5-yl]-6-methyl-2-oxo-6H-1,3,4-thiadiazin-3-yl}ethyl)nicotinamide,
N-(2-{5-[2-(3-fluorophenyl)-1-methyl-1H-benzimidazol-5-yl]-6-methyl-2-oxo-6H-1,3,4-thiadiazin-3-yl}ethyl)benzamide,
N-(2-{5-[2-(3-fluorophenyl)-1-methyl-1H-benzimidazol-5-yl]-6-methyl-2-oxo-6H-1,3,4-thiadiazin-3-yl}ethyl)acetamide,
N-(2-{5-[2-(3-fluorophenyl)-1-methyl-1H-benzimidazol-5-yl]-6-methyl-2-oxo-6H-1,3,4-thiadiazin-3-yl}ethyl)isobutyramide,
(S)-5-{2-[4-((S)-methanesulfinyl)-3-methoxyphenyl]-1H-benzimidazol-5-yl}-6-methyl]-3,6-dihydro-2H-1,3,4-thiadiazin-2-one,
(R)-5-{2-[4-((S)-methanesulfinyl)-3-methoxyphenyl]-1H-benzimidazol-5-yl}-6-methyl]-3,6-dihydro-2H-1,3,4-thiadiazin-2-one, (S)-5-{2-[4-((R)-methanesulfinyl)-3-methoxyphenyl]-1H-benzimidazol-5-yl}-6-methyl]-3,6-dihydro-2H-1,3,4-thiadiazin-2-one,
(R)-5-{2-[4-((R)-methanesulfinyl)-3-methoxyphenyl]-1H-benzimidazol-5-yl}-6-methyl]-3,6-dihydro-2H-1,3,4-thiadiazin-2-one,
1-(4-acetylphenyl)-3-(2-{5-[2-(3-fluorophenyl)-1-methyl-1H-benzimidazol-5-yl]-6-methyl-2-oxo-6H-1,3,4-thiadiazin-3-yl}ethyl)urea,
1-(3-fluorophenyl)-3-(2-{5-[2-(3-fluorophenyl)-1-methyl-1H-benzimidazol-5-yl]-6-methyl-2-oxo-6H-1,3,4-thiadiazin-3-yl}ethyl)urea,
5-[1-cyclopropylmethyl-2-(1-methyl-1H-pyrrol-2-yl)-1H-benzimidazol-5-yl]-6-methyl]-3,6-dihydro-2H-1,3,4-thiadiazin-2-one,
5-[1-cyclopropylmethyl-2-(1-methyl-1H-imidazol-2-yl)-1H-benzimidazol-5-yl]-6-methyl]-3,6-dihydro-2H-1,3,4-thiadiazin-2-one,
5-(1-cyclopropylmethyl-2-thiophen-3-yl-1H-benzimidazol-5-yl)-6-methyl]-3,6-dihydro-2H-1,3,4-thiadiazin-2-one,
5-[1-cyclopropylmethyl-2-(2-methoxyphenyl)-1H-benzimidazol-5-yl]-6-methyl]-3,6-dihydro-2H-1,3,4-thiadiazin-2-one,
5-[1-cyclopropylmethyl-2-(4-methoxyphenyl)-1H-benzimidazol-5-yl]-6-methyl]-3,6-dihydro-2H-1,3,4-thiadiazin-2-one,
5-[1-cyclopropylmethyl-2-(3-hydroxy-4-methoxyphenyl)-1H-benzimidazol-5-yl]-6-methyl]-3,6-dihydro-2H-1,3,4-thiadiazin-2-one, in the form of tautomers, enantiomers, diastereoisomers and epimers, and also the pharmaceutically acceptable salts, and the crystalline forms, or mixtures thereof.

The compounds that are more particularly preferred are those chosen from:
5-[2-(3-fluorophenyl)-1-methyl-1H-benzimidazol-5-yl]-3-isopropyl-6-methyl]-3,6-dihydro-2H-1,3,4-thiadiazin-2-one,
5-[2-(3-fluorophenyl)-1-methyl-1H-benzimidazol-5-yl]-6-methyl-3-propyl]-3,6-dihydro-2H-1,3,4-thiadiazin-2-one,
5-{2-[4-(1H-imidazol-1-yl)phenyl]-1H-benzimidazol-5-yl}-6-methyl-3,6-dihydro-2H-1,3,4-thiadiazin-2-one dihydrochloride,
5-[1-cycloheptyl-2-(3-methoxyphenyl)-1H-benzimidazol-5-yl]-3-methyl]-3,6-dihydro-2H-1,3,4-thiadiazin-2-one,
6-methyl-5-{2-[3-(methoxy)phenyl]-1H-benzimidazol-5-yl}-3,6-dihydro-2H-1,3,4-thiadiazin-2-one,
5-{2-[3-methoxy-4-(methylsulfinyl)phenyl]-1H-benzimidazol-5-yl}-6-methyl-3,6-dihydro-2H-1,3,4-thiadiazin-2-one hydrochloride, in the form of tautomers, enantiomers, diastereoisomers or epimers, and also the free forms or the pharmaceutically acceptable salts, and the crystalline forms, or mixtures thereof.

In the present description, the terms used have the following meanings, unless otherwise indicated:

the term "alkyl" denotes a linear or branched alkyl radical. Among the $(C_1-C_{20})$alkyl radicals that may especially be mentioned, in a non-limiting manner, are methyl, ethyl, propyl, isopropyl, butyl, sec-butyl, tert-butyl, pentyl, hexyl, octyl, decyl, dodecyl, hexadecyl and octadecyl radicals;

the term "alkenyl" denotes a linear or branched hydrocarbon-based radical containing one or more unsaturations in the form of a double bond. $(C_2-C_{20})$-Alkenyl radicals that may be mentioned, in a non-limiting manner, include ethenyl, is prop-2-enyl, but-2-enyl, but-3-enyl, pent-2-enyl, pent-3-enyl and pent-4-enyl radicals;

the term "alkynyl" denotes a linear or branched hydrocarbon-based radical containing one or more unsaturations in the form of a triple bond, which may optionally also comprise one or more unsaturations in the form of a double bond. $(C_2-C_{20})$Alkynyl radicals that may be mentioned, in a non-limiting manner, include ethynyl, prop-2-ynyl, but-2-ynyl, but-3-ynyl, pent-2-ynyl, pent-3-ynyl and pent-4-ynyl radicals;

the term "alkoxy" refers to the term "alkyl-oxy";

among the "halogens", mention may be made especially of fluorine, chlorine and bromine;

the term "cycloalkyl" denotes an optionally substituted saturated cyclic hydrocarbon-based radical, and comprises mono-, bi- and tricyclic compounds, containing from 3 to 10 carbon atoms. Among the "cycloalkyls" that may especially be mentioned are cyclopropyl, cyclobutyl, cyclopentyl, cyclohexyl, cycloheptyl, cyclooctyl, cyclodecyl and adamantyl radicals, and others, all being optionally substituted;

the term "cycloalkenyl" denotes an optionally substituted mono-, bi- or tri-cyclic hydrocarbon-based radical comprising at least one unsaturation in the form of a double bond, containing from 3 to 10 carbon atoms. Among the "cyclo-alkenyls" that may especially be mentioned are cyclopentenyl, cyclopentadienyl, cyclohexenyl, camphenyl and norbornenyl radicals;

in the present invention, the term "heterocycloalkyl" denotes both hetero-cycloalkyls and heterocycloalkenyls. These radicals are optionally substituted and may be mono-, bi- or tricyclic and comprise one or more heteroatoms preferably chosen from O, S and N, optionally in oxidised form (in the case of S and N), and also optionally one or two double bonds. Preferably, at least one of the rings comprises from 1 to 4 and more preferentially from 1 to 3 endocyclic heteroatoms.

Advantageously, a heterocycloalkyl radical comprises one or more rings, each of which is 5- to 8-membered. Examples of heterocycloalkyl radicals are: morpholinyl, piperidyl, piperazinyl, thiazolidinyl, oxazolidinyl, tetrahydrothienyl, dihydrofuryl, tetrahydrofuryl, pyrazolidinyl, 1,3-dioxolanyl, pyrrolidinyl, pyranyl, dihydropyranyl, isoxazolidinyl, imidazolinyl, imidazolidinyl and pyrazolidinyl;

the term "aryl" denotes monocyclic or polycyclic aromatic radicals containing from 5 to 14 ring atoms, and at least one ring contains a system of conjugated pi ($\pi$) electrons, including biaryl groups, each of which is possibly substituted. Among the "aryls" that may especially be mentioned are phenyl, naphthyl, biphenyl, anthryl, phenanthryl and indenyl radicals;

the term "heteroaryl" denotes an aromatic heterocyclic radical containing from 5 to 14 endocyclic atoms, among which 1 to 4 atoms are heteroatoms, preferably chosen from oxygen, sulfur and nitrogen. Among the "heteroaryls" that may especially be mentioned are furyl, benzofuryl, thienyl, pyridyl, pyridyl-N-oxide, pyrimidinyl, pyrazinyl, oxazolyl, thiazolyl, isoxazolyl, quinolyl, triazolyl, pyridazinyl, pyrrolyl, imidazolyl, indazolyl, isothiazolyl, indolyl and oxadiazolyl.

The present invention also relates to the process for the preparation of the compounds of the general formula (I).

According to a first embodiment, the process for the preparation of the compounds of the formula (I) in which R3 is other than a hydrogen atom includes the step that consists in substituting the corresponding compound of the formula (I) in which R3 is equal to H, i.e. the compound of the formula (F) below:

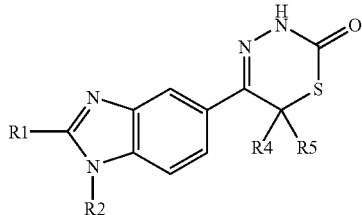

(F)

in which R1, R2, R4 and R5 are as defined in formula (I), using a suitable reagent, depending on the value of the desired group R3. This reaction, within the capability of a person skilled in the art, may be performed by application or adaptation of any method known in the prior art, for instance as described by Jerry March, Advanced Organic Chemistry, 3$^{rd}$ Ed., Wiley Interscience, pp. 310-316.

This reaction can be performed according to one or other of the following embodiments:

According to a first embodiment, the dihydrothiadiazinone can be prepared by the following reaction:

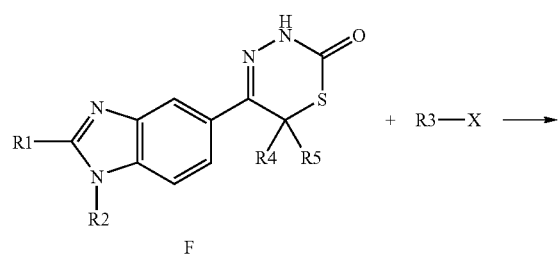

F

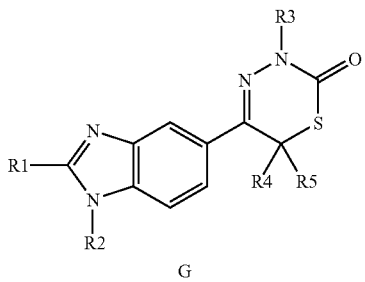

G in which R1, R2, R4 and R5 are as described above and R3 is other than a is hydrogen atom. Compound G can be obtained by reacting compound F with, for example, a branched or unbranched alkyl halide. The reaction can be performed in the presence of an organic base, such as, in a non-limiting manner, triethylamine, pyridine or diisopropylethylamine, or alternatively in the presence of a mineral base, such as sodium hydrogen carbonate or caesium carbonate, in a solvent, such as dimethylformamide or acetonitrile, or alternatively in a solvent of ether type, such as THF or dioxane, at a temperature ranging from 0° C. to the boiling point of the solvent used, the reaction time possibly being between 10 minutes and 48 hours and preferably 1 hour to 24 hours.

According to a second embodiment, if R3 represents an alkyl group substituted by an amino group, the substitution of the dihydrothiadiazinone can be performed by the following reactions:

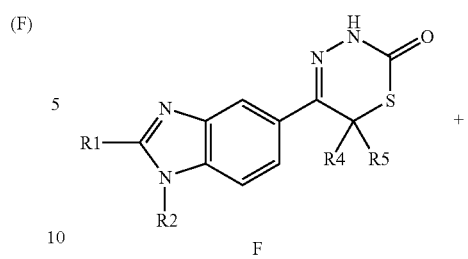

F

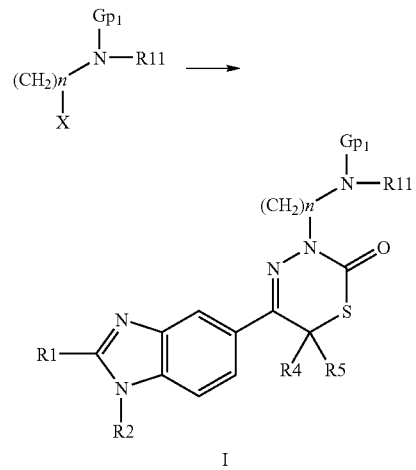

I in which R1, R2, R4, R5, R11 and n are as described above, and in which the protecting group Gp1 may be chosen from those commonly used in the practice of organic synthesis for the protection of amines and n is an integer between 1 and 10, and then

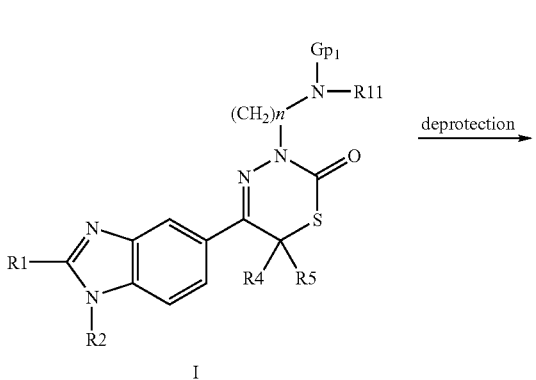

I

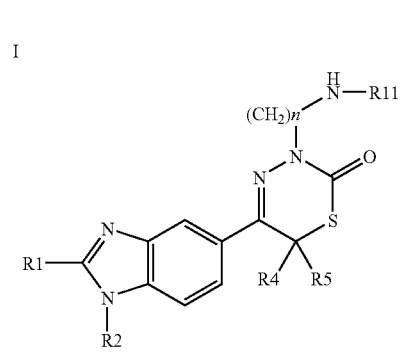

J in which Gp1, R1, R2, R4, R5, R11 and n are as described above.

Under similar or slightly modified reaction conditions, just as for compound G, compound I can be obtained by reacting compound F with, for example, a branched or unbranched alkyl halide, bearing in this case a substituted or unsubstituted amine function and protected with a protecting group, such as, in a non-limiting manner, a tert-butoxycarbonyl group or a benzyloxycarbonyl group.

Compound J is obtained from compound I using the known deprotection methods; mention may be made especially of the use of trifluoroacetic acid. It is also advantageously possible to use a solution of hydrochloric acid in a solvent, such as dioxane at a temperature of between 0° C. and the boiling point of the solvent used.

According to a third embodiment, if R3 represents a group $(CH_2)_n$—NR11-COR14, as defined in the general formula (I), the process according to the invention includes the following step:

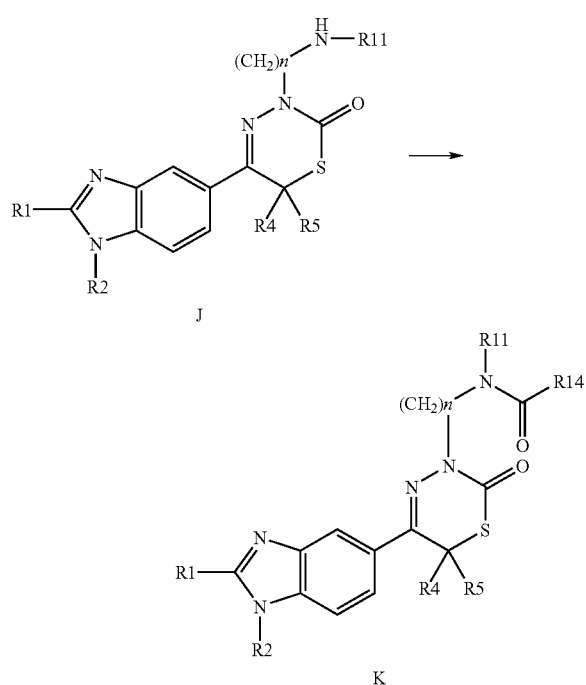

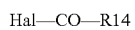

in which R1, R2, R4, R5, R11, R14 and n are as described above.

Compound K can be obtained via the action of a suitably selected acid halide of the formula Hal—CO—R14 in which Hal represents a halogen atom, for example an acid chloride, such as, for example, phenacyl chloride, on compound J in the presence of an organic base, such as, in a non-limiting manner, triethylamine, pyridine or diisopropylethylamine, in a solvent, such as acetonitrile, toluene, dichloromethane or tetrahydrofuran.

It is also possible to use a mineral base, such as, in a non-limiting manner, sodium hydrogen carbonate or caesium carbonate. These derivatives of amide type can also be obtained via the known methods of acid activation using coupling agents, such as carbonyldiimidazole or, in a non-limiting manner, 1-hydroxybenzotriazole (HOBt) or benzotriazol-1-yloxytripyrrolidinophosphonium hexafluorophosphate (PyBOP).

According to another embodiment, if R3 represents an alkyl group substituted by a group of the formula —NR11—S(O)$_p$—R15, as defined in the general formula (I), the process according to the invention includes the following step:

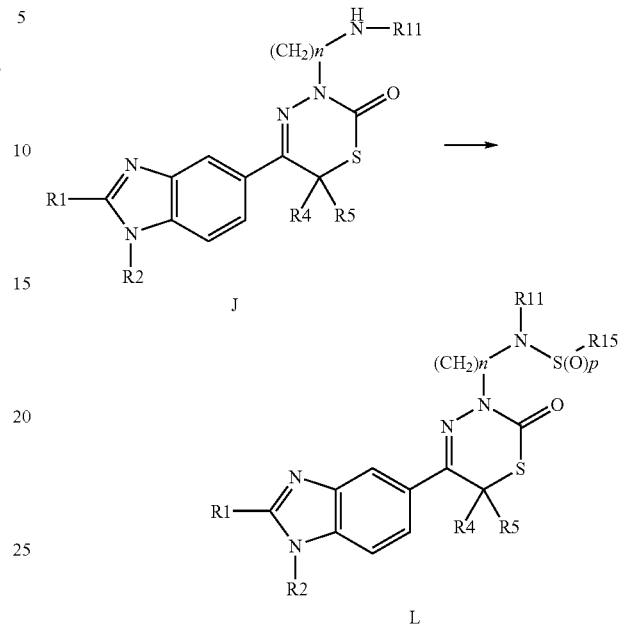

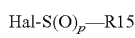

in which R1, R2, R4, R5, R11, R15, n and p are as described above.

Compound L can be obtained via the action of a suitably selected sulfonyl halide of the formula Hal-S(O)$_p$—R15 in which Hal represents a halogen atom and p is as defined above, for example a sulfonyl chloride, such as, for example, benzenesulfonyl chloride, on compound J in the presence of an organic base, such as, in a non-limiting manner, triethylamine, pyridine or diisopropylethylamine, in a solvent that is inert with respect to the reaction, such as acetonitrile, toluene or dichloromethane, or alternatively an ether, such as tetrahydrofuran or dioxane. A mineral base can also be used, such as, in a non-limiting manner, sodium hydrogen carbonate or caesium carbonate. The reaction can be performed at a temperature of between −10° C. and the boiling point of the solvent used; in the present case, the reaction can be performed at a temperature close to room temperature.

According to another embodiment, if R3 represents an alkyl group substituted by a group of the formula —NR11—C(O)—NR12R13, as defined in the general formula (I), the process according to the invention includes the following step:

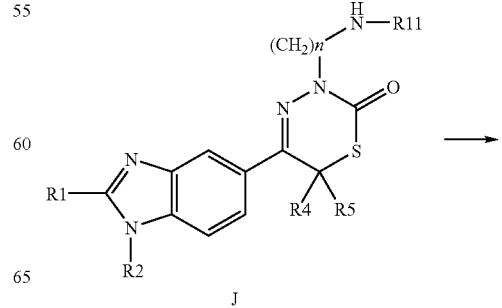

-continued

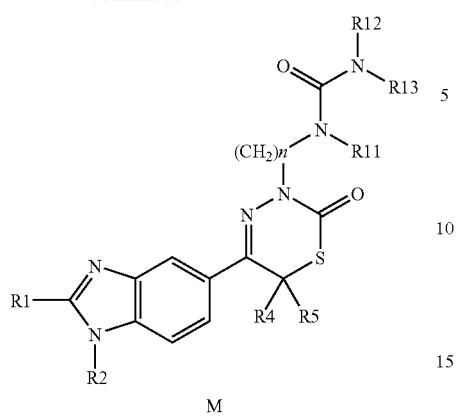

M

-continued

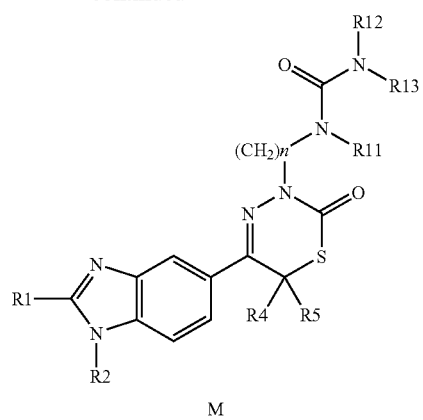

M in which R1, R2, R4, R5, R11, R12, R13 and n are as described above.

If R12 is a hydrogen and R13 is other than a hydrogen, compound M can be obtained by reacting compound J with a suitably selected isothiocyanate of the formula $$R13-N=C=O$$

in a solvent of ether type, such as tetrahydrofuran or dioxane, at a temperature of between 0° C. and the boiling point of the solvent used.

If R12 and R13 are both other than hydrogen, compound M can be obtained from compound J via the action of carbonyl-diimidazole, to give compound J1:

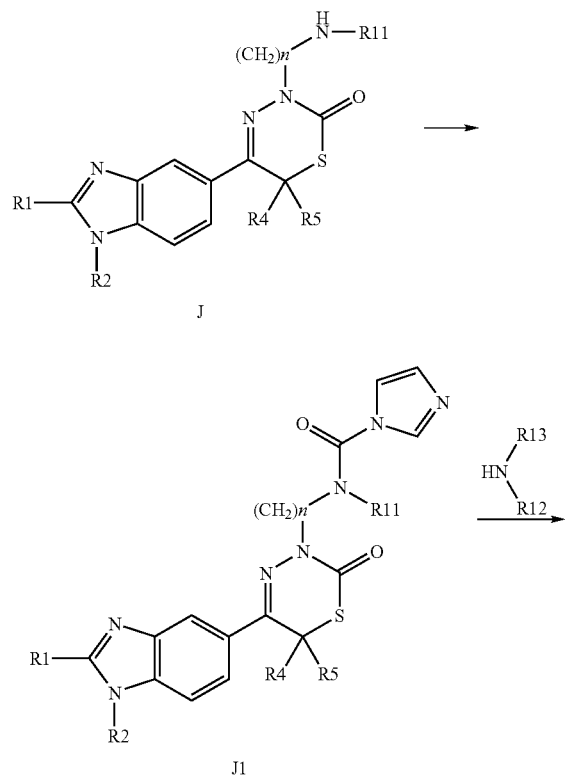

followed by reacting the obtained compound J1 with a suitably selected amine to give compound M.

The reaction can be performed in a solvent, such as dichloromethane, at a temperature ranging from room temperature to the boiling point of the solvent used.

According to another embodiment, if R3 represents an alkyl group substituted by an OH group, the process according to the invention includes the following steps:

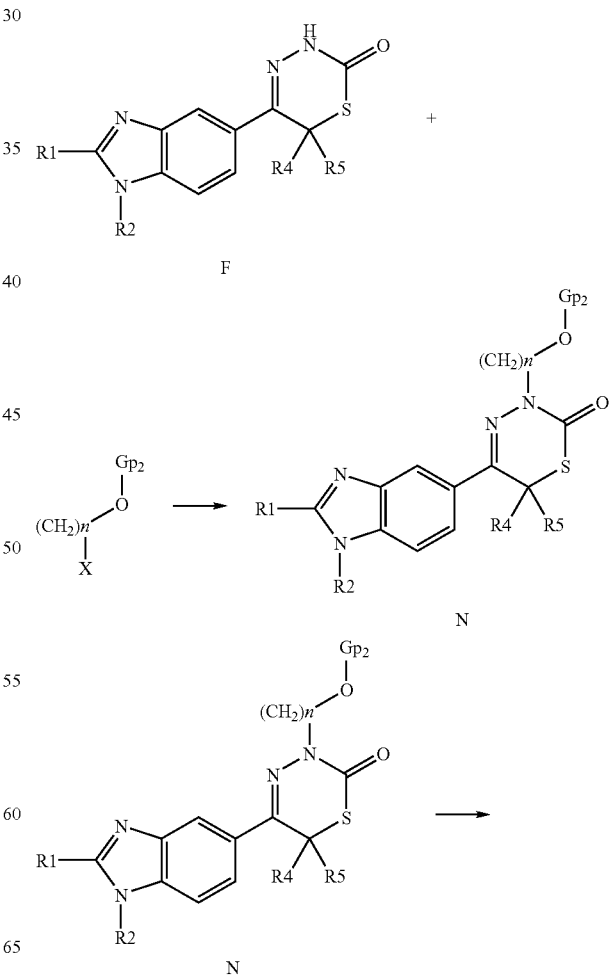

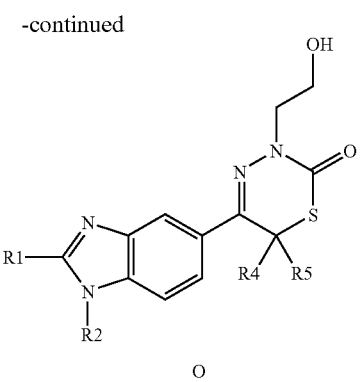

in which R1, R2, R4, R5, and n are as described above and in which the protecting group Gp2 can be chosen from those commonly used in the practice of organic synthesis for the protection of alcohols.

Under similar or slightly modified reaction conditions, just as for compound G, compound N can be obtained by reacting compound F with, for example, a branched or unbranched alkyl halide bearing, in this case, an alcohol function protected with a protecting group, such as, in a non-limiting manner, a tetrahydro-pyranyl group. The alcohol may also be protected in silyl ether form.

Compound O can be obtained from compound N using the known deprotection methods. If the alcohol is protected with a tetrahydropyranyl group, it is possible to use a solution of hydrochloric acid in a solvent of alcohol type, such as methanol, at a temperature of between 0° C. and the boiling point of the solvent used. In this case, the reaction can be performed at room temperature, the reaction time possibly being between 30 minutes and 24 hours.

Advantageously, it is also possible to use a solution of hydrochloric acid in a solvent, such as dioxane, at a temperature of between 0° C. and the boiling point of the solvent used.

The compounds of the formula (I) in which the group R3 represents an alternative functional group can be obtained from the intermediates F, G, I, J, K, L, M, N or O, by application or adaptation of methods known to those skilled in the art, especially those described by Larock in *Comprehensive Organic Transformations*, VCH Pub 1989 or those described in the examples that follow.

The compound of the formula F can be obtained via one or other of the following embodiments:

According to a first embodiment, the process for the preparation of the compound of the formula F includes the following steps:

Step 1a

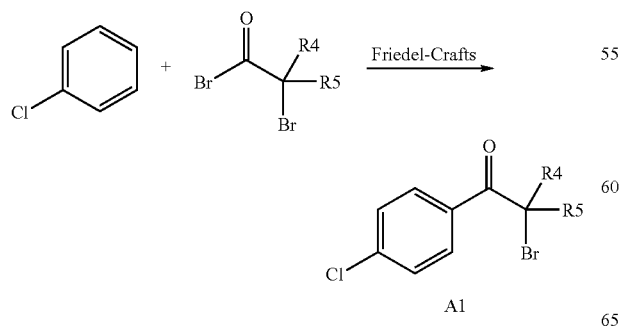

in which R4 and R5 are as described above;

or according to the variant

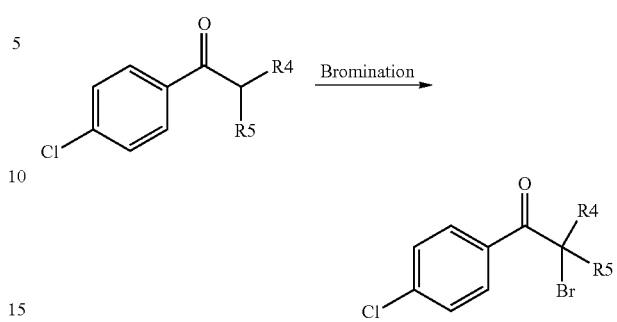

in which R4 and R5 are as described above;

Step 2a

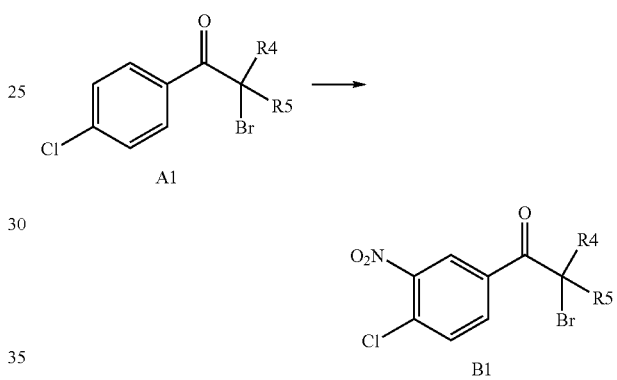

in which R4 and R5 are as described above;

Step 3a

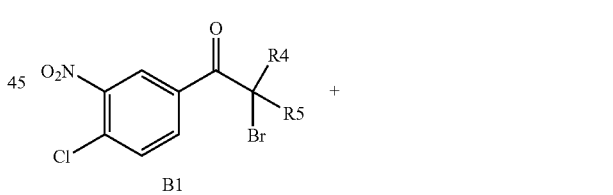

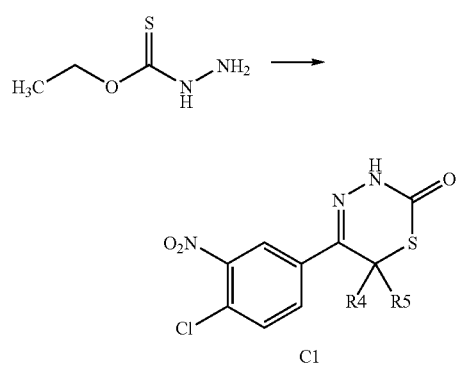

in which R4 and R5 are as described above;

Step 4a

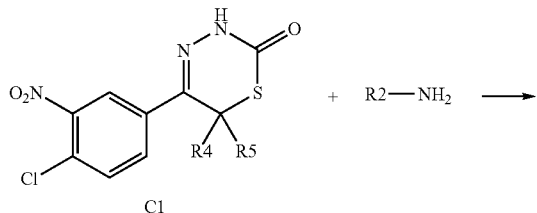

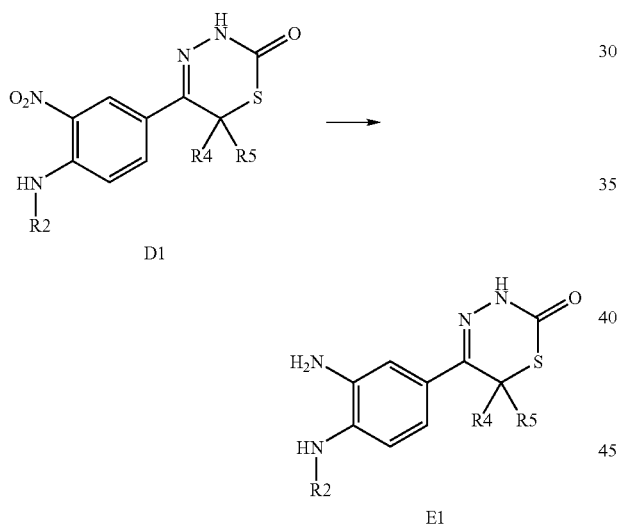

in which R2, R4 and R5 are as described above;
Step 6a

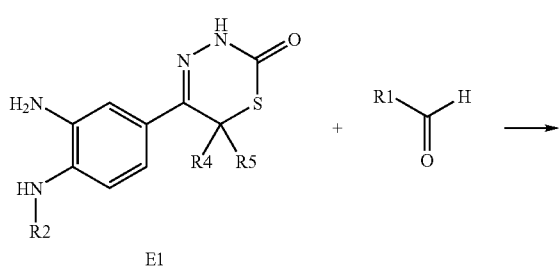

-continued

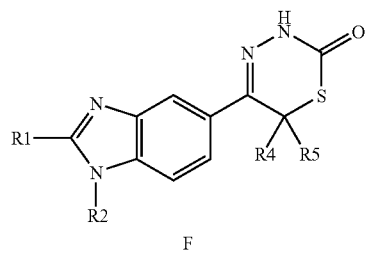

in which R1, R2, R4 and R5 are as described above;
in which steps, more specifically:

Compound A1 can be obtained via the action of a suitably selected acyl halide on chlorobenzene, using a Friedel-Crafts reaction in the presence of a catalyst, such as aluminium chloride.

Compound A1 can also be obtained by bromination of a suitably selected ketone, using the known techniques of organic chemistry.

It is possible to use bromine in a solvent, such as, in a non-limiting manner, acetic acid.

The synthesis of compound B1 can be performed via the action of nitric acid on compound A1. The reaction can be performed at a temperature ranging from −30° C. to 0° C. and preferably from −25° C. to 15° C., over a period that can range from 10 minutes to 2 hours.

Compound C1 can be obtained by cyclisation of compound B1 with O-ethyl hydrazinecarbothioate in a solvent of alcohol type, such as ethanol, or alternatively in an aprotic solvent, such as acetonitrile. The reaction can be performed at a temperature ranging from room temperature to the boiling point of the solvent used, preferably at the boiling point of the solvent used.

Compound D1 can be obtained by reaction of compound C1 with a suitably selected amine. The reaction can be performed in a solvent, such as acetonitrile in the presence of a mineral base, such as sodium carbonate, potassium carbonate or sodium hydrogen carbonate, or alternatively in the presence of an organic base, such as triethylamine, or alternatively in the presence of an excess of the base used in the reaction. The reaction temperature can be between 0° C. and the boiling point of the solvent used.

Compound E1 can be obtained from compound D1 via reduction of the nitro group. This reduction will be performed using the known reduction methods; mention may be made especially of hydrogenation in the presence of a catalyst, such as palladium-on-charcoal or Raney nickel in a solvent of alcohol type, such as methanol, at a temperature of between 10° C. and the boiling point of the solvent under consideration.

This reduction can be performed at a temperature ranging from atmospheric pressure to a pressure of 100 bar.

In the present case, a reduction using a metal, such as zinc in a solvent, such as acetic acid will advantageously be used.

According to a second embodiment, the process for the preparation of the compound of the formula F includes the following steps:

Step 1b

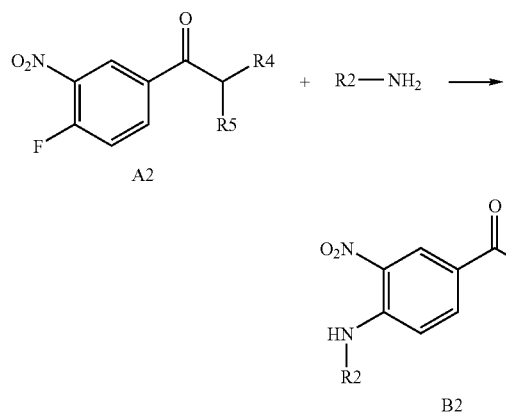

in which R2, R4 and R5 are as described above;

Step 2b

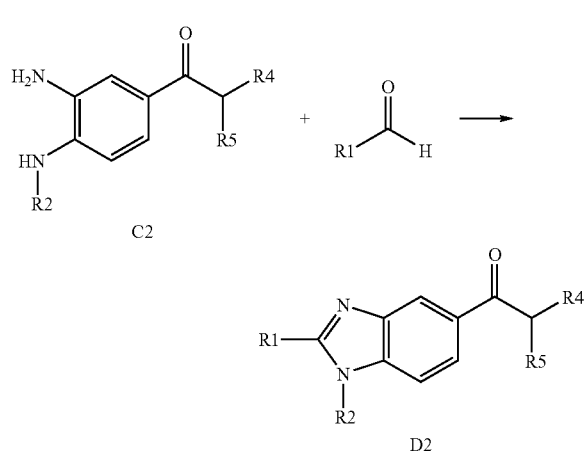

in which R2, R4 and R5 are as described above;

Step 3b

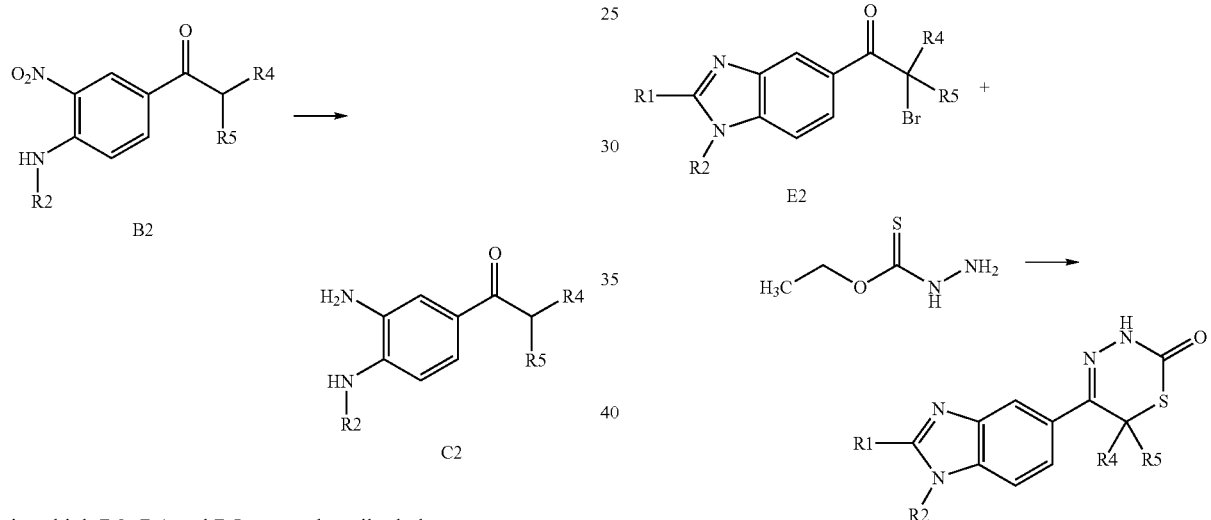

in which R1, R2, R4 and R5 are as described above.

Step 4b

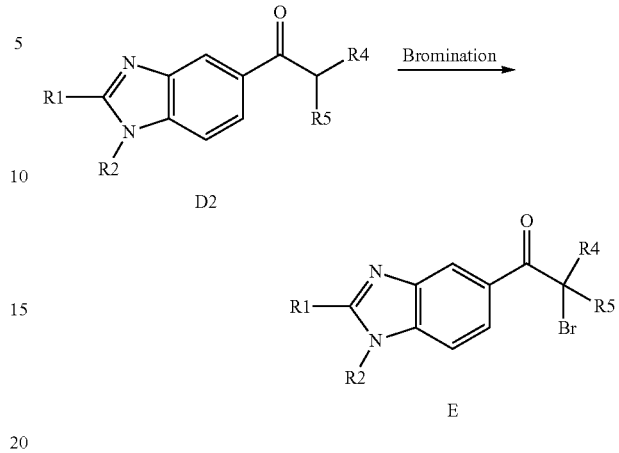

in which R1, R2, R4 and R5 are as described above;

Step 5b in which R1, R2, R4 and R5 are as described above;
in which steps, more specifically:

Compound B2 can be obtained by reacting compound A2 with a suitably selected amine. The reaction can be performed in a solvent, such as acetonitrile in the presence of a mineral base, such as, in a non-limiting manner, sodium carbonate, potassium carbonate or sodium hydrogen carbonate, or alternatively in the presence of an organic base, such as triethylamine. The reaction can also be performed in the presence of an excess of the base used in the reaction. The reaction temperature can be between 0° C. and the boiling point of the solvent used.

Compound C2 can be obtained from compound B2 via reduction of the nitro group. This reduction will be performed using the known reduction methods. Mention may be made especially of hydrogenation in the presence of a catalyst, such as palladium-on-charcoal in a solvent of alcohol type, such as methanol, or in a solvent of ether type, such as dioxane, at a temperature of between 10° C. and the boiling point of the solvent under consideration. This reduction can be performed at a pressure ranging from atmospheric pressure to a pressure of 100 bar.

Compound D2 can be obtained by reacting compound C2 with a suitably selected aldehyde in order to obtain the benzimidazole group by cyclisation.

The reaction can be performed in a solvent, such as N-methylpyrrolidone in the presence of sodium bisulfite, at a temperature of between room temperature and the boiling point of the solvent used. Preferably, the reaction will be performed at temperature close to the boiling point of the solvent used, for a time that can range from 1 hour to 24 hours.

Compound E2 will be obtained by selected halogenation of compound D2 using a brominating agent, such as bromine in a solvent, such as acetic acid.

Compound F can be obtained by cyclisation of compound E2 with O-ethyl hydrazinecarbothioate in a solvent of alcohol type, such as ethanol or in an aprotic solvent, such as acetonitrile. The reaction can be performed at a temperature ranging from room temperature to the boiling point of the solvent used, preferably at the boiling point of the solvent used.

Optionally, the said process may also include the step that consists in isolating the product obtained.

In the reactions described hereinbelow, it may be necessary to protect the reactive functional groups, for example the hydroxyl, amino, imino, thio or carboxyl groups, if they are desired in the final product, to avoid their unwanted participation in the reactions. The conventional protecting groups can be used in accordance with the standard practice; for examples, see T. W. Green and P. G. M. Wuts in *Protective Groups in Organic Chemistry*, John Wiley and Sons, 1991; J. F. W. McOmie in *Protective Groups in Organic Chemistry*, Plenum Press, 1973.

The compound thus prepared can be recovered from the reaction mixture via the conventional means. For example, the compounds can be recovered by distilling the solvent from the reaction mixture or, if necessary, after distilling off the solvent from the mixture of the solution, pouring the remainder into water, followed by extraction with a water-immiscible organic solvent, and distilling the solvent from the extract. In addition, the product can also be purified, if so desired, by various techniques, such as recrystallisation, reprecipitation or various chromatographic techniques, especially column chromatography or preparative thin-layer chromatography.

It will be appreciated that the compounds that are useful according to the present invention may contain asymmetric centres. These asymmetric centres can be, independently, of R or S configuration. It will be apparent to a person skilled in the art that certain compounds that are useful according to the invention may also exhibit geometrical isomerism. It should be understood that the present invention includes individual geometrical isomers and stereoisomers, and mixtures thereof, including racemic mixtures, of compounds of the formula (I) above. Isomers of this type can be separated from their mixtures by application or adaptation of known processes, for example chromatography techniques or recrystallisation techniques, or they are prepared separately from suitable isomers of their intermediates.

For the purposes of the present text, it is understood that the tautomeric forms are included in the citation of a given group, for example thio/mercapto or oxo/hydroxyl.

The acid-addition salts are formed with the compounds that are useful according to the invention in which a basic function, such as an amino, alkylamino or dialkylamino group is present. The pharmaceutically acceptable, i.e. non-toxic, acid-addition salts are preferred. The selected salts are optimally chosen so as to be compatible with the usual pharmaceutical vehicles and suitable for oral or parenteral administration. The acid-addition salts of the compounds that are useful according to the present invention can be prepared by reacting the free base with the appropriate acid, by application or adaptation of known processes. For example, the acid-addition salts of the compounds that are useful according to the present invention can be prepared either by dissolving the free base in water or in a basified aqueous solution or suitable solvents containing the appropriate acid, and isolating the solvent by evaporating the solution, or by reacting the free base and the acid in an organic solvent, in which case the salt separates out directly or can be obtained by concentrating the solution. Among the acids that are suitable for use in the preparation of these salts are hydrochloric acid, hydrobromic acid, phosphoric acid, sulfuric acid, various organic carboxylic and sulfonic acids, such as acetic acid, citric acid, propionic acid, succinic acid, benzoic acid, tartaric acid, fumaric acid, mandelic acid, ascorbic acid, malic acid, methanesulfonic acid, toluenesulfonic acid, fatty acids, adipate, alginate, ascorbate, aspartate, benzenesulfonate, benzoate, cyclopentanepropionate, digluconate, dodecyl sulfate, bisulfate, butyrate, lactate, laurate, lauryl sulfate, malate, hydriodide, 2-hydroxyethanesulfonate, glycerophosphate, picrate, pivalate, pamoate, pectinate, persulfate, 3-phenylpropionate, thiocyanate, 2-naphthalenesulfonate, undecanoate, nicotinate, hemisulfate, heptonate, hexanoate, camphorate, camphorsulfonate and the like.

The acid-addition salts of the compounds that are useful according to the present invention can be regenerated from the salts by application or adaptation of known processes. For example, the parent compounds that are useful according to the invention can be regenerated from their acid-addition salts by treatment with an alkali, for example aqueous sodium bicarbonate solution or aqueous ammonia solution.

The compounds that are useful according to the present invention can be regenerated from their base-addition salts by application or adaptation of known processes. For example, the parent compounds that are useful according to the invention can be regenerated from their base-addition salts by treatment with an acid, for example hydrochloric acid.

The base-addition salts can be formed if the compound that is useful according to the invention contains a carboxyl group, or a sufficiently acidic bio-isostere. The bases that can be used to prepare the base-addition salts preferably include those that produce, if they are combined with a free acid, pharmaceutically acceptable salts, i.e. salts whose cations are not toxic to the patient in the pharmaceutical doses of the salts, such that the beneficial inhibitory effects intrinsic to the free base are not negated by the side effects attributable to the cations. The pharmaceutically acceptable salts, including those derived from alkaline-earth metal salts, within the scope of the present invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide and the like.

The compounds that are useful according to the present invention can be readily prepared, or formed during the process of the invention, in the form of solvates (for example hydrates). The hydrates of the compounds that are useful according to the present invention can be readily prepared by recrystallisation of an aqueous/organic solvent mixture, using organic solvents, such as dioxane, tetrahydrofuran or methanol.

The starting materials or the reagents used are commercially available and/or can be prepared by application or adaptation of known processes, for example processes as described in the Reference Examples or obvious chemical equivalents thereof.

The compounds of the invention as defined above show hypoglycaemiant activity and, in this respect, are useful in the treatment of pathologies associated with insulin resistance syndrome.

Specifically, insulin resistance is characterised by a reduction in the action of insulin (cf. "Presse Médicale", (1997), 26(14), 671-677) and is involved in a large number of pathological states, such as diabetes and more particularly non-insulin-dependent diabetes (type II diabetes or NIDDM), dyslipidaemia, obesity, arterial hypertension and also certain microvascular and macrovascular complications, for instance atherosclerosis, retinopathy and neuropathy.

In this respect, reference will be made, for example, to *Diabetes,* 37, (1988), 1595-1607; *Journal of Diabetes and its complications* 12, (1998), 110-119 or *Horm. Res,* 38, (1992), 28-32.

A subject of the present invention is thus also pharmaceutical compositions comprising, as active principle, at least one compound according to the invention.

The pharmaceutical compositions according to the invention can be in forms intended for parenteral, oral, rectal, permucous or percutaneous administration.

They will thus be in the form of injectable solutions or suspensions or multi-dose bottles, in the form of plain or coated tablets, sugar-coated tablets, wafer capsules, gel capsules, pills, cachets, powders, suppositories or rectal capsules, or solutions or suspensions, for percutaneous use in a polar solvent, or for permucous use.

The excipients that are suitable for such administrations are pharmaceutically acceptable excipients, for instance cellulose or microcrystalline cellulose derivatives, alkaline-earth metal carbonates, magnesium phosphate, starches, modified starches and lactose for the solid forms.

Cocoa butter or polyethylene glycol stearates are the preferred excipients for rectal use.

Water, aqueous solutions, physiological saline or isotonic solutions are the vehicles most conveniently used for parenteral use.

For example, if the compounds according to the present invention are administered orally, in the form of plain or coated tablets, sugar-coated tablets, wafer capsules, gel capsules, pills, cachets or powders, the dosage can range between about 0.1 mg/kg and about 100 mg/kg, preferably between about 0.5 mg/kg and about 50 mg/kg, more preferably between 1 mg/kg and 10 mg/kg and most preferably between about 2 mg/kg and about 5 mg/kg.

Assuming that the weight of the patient to be treated can range between 10 kg and 100 kg, and according to the dosage mentioned above, the daily intakes can be between about 1 to 10 mg/day and about 1000 to 10 000 mg/day, preferably between about 5 to 50 mg/day and about 500 to 5000 mg/day, more preferably between about 10 to 100 mg/day and about 100 to 1000 mg/day and most preferably between about 20 to 200 mg/day and about 50 to 500 mg/day.

As indicated above, the formulations of the present invention that are suitable for oral administration can be in the form of individual doses, such as tablets, cachets or sugar-coated tablets, each containing a predetermined amount of active material; the formulations can also be in the form of powder or granules, in the form of a solution or a suspension in an aqueous or non-aqueous medium, or alternatively in the form of a liquid emulsion of oil-in-water type or in the form of a liquid emulsion of water-in-oil type. The active material can also be administered in the form of a bolus, paste or electuary.

In the case of non-insulin-dependent diabetes, in man, hyperglycaemia is the result of two major defects: an impairment in insulin secretion and a reduction in the efficacy of insulin at three sites, namely the liver, the muscles and the adipose tissue.

By inhibiting gluconeogenesis via inhibition of the key enzyme fructose-1,6-bisphosphatase, the compounds of the present invention are thus capable of improving the glycaemia of non-insulin-dependent diabetic patients.

Thus, and according to another aspect, the present invention relates to the use of at least one compound of the general formula (I), the possible tautomeric forms thereof and the possible enantiomers, diastereoisomers, epimers and organic or mineral salts thereof, and also "prodrugs" thereof, for the treatment or prevention of pathologies associated with excessive glycogen storage or diseases, such as cardiovascular diseases, including atherosclerosis, myocardial ischaemia, for the treatment of or preventing type II diabetes and diseases associated with metabolic disorders, such as hypercholesterolaemia or hyperlipidaemia, which are exacerbated by hyperinsulinaemia and hyperglycaemia, and the treatment and prevention of obesity, or alternatively of diabetes complications, such as nephropathy, retinopathy or neuropathy.

According to another subject, the present invention also relates to the use of a compound of the general formula (I) for the manufacture of a medicament for inhibiting or limiting the hepatic production of glucose.

The examples that follow illustrate the invention without, however, limiting it. The starting materials used are known products or are prepared by known procedures.

The percentages are expressed on a weight basis, unless otherwise mentioned.

The compounds were characterised especially via the following analytical techniques:

The NMR spectra were acquired using a Brüker Avance DPX 300 MHz spectrometer.

The masses were determined by HPLC coupled to an Agilent Series 1100 mass detector.

The melting points (m.p.) were measured on a Köfler Leica VMBH block.

EXAMPLE 1

2-bromo-1-(4-chlorophenyl)propan-1-one

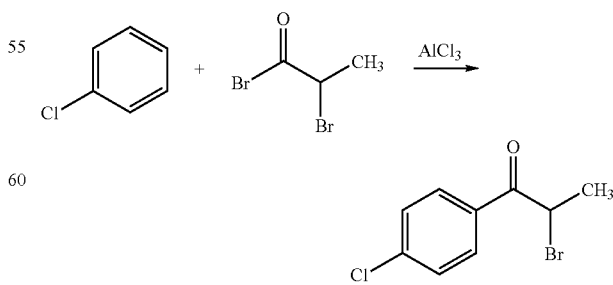

To 200 ml of dichloromethane are added 23.7 g (0.176 M) of aluminium chloride. The mixture is cooled to 10° C. and 10 g (0.089 M) of chlorobenzene are added dropwise. The resulting mixture is stirred for one hour at 15° C. followed by dropwise addition of 9.2 ml (0.089 M) of 2-bromopropionyl bromide. The reaction medium is then stirred for 16 hours at room temperature. The reaction medium is then poured into an ice/water mixture. The organic phase is separated out by settling, washed twice with demineralised water and then dried over sodium sulfate. After evaporating under vacuum, an oil is obtained, which crystallises to give 21 g of 2-bromo-1-(4-chlorophenyl)propan-1-one.

Yield: 95.5%

$^1$H NMR (300 MHz/DMSO-d6) δ: 1.75 (d, 3H), 5.78 (q, 1H), 7.62 (d, 2H), 8.05 (d, 2H)

EXAMPLE 2

1-(4-chloro-3-nitrophenyl)-2-bromopropan-1-one

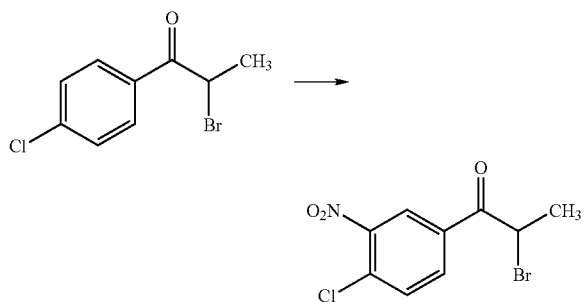

To 80 ml of fuming nitric acid at −20° C. are added portionwise 20.5 g (0.08 M) of 2-bromo-1-(4-chlorophenyl)propan-1-one. After addition, the reaction medium is stirred at −20° C. for 15 minutes. The reaction medium is then poured onto ice and extracted with 300 ml of dichloromethane.

The combined organic phases are washed twice with water and then dried over sodium sulfate and concentrated under vacuum. The oil obtained is purified by chromatography on silica using dichloromethane as eluent, to give 22.5 g of 1-(4-chloro-3-nitrophenyl)-2-bromopropan-1-one in the form of a colourless oil.

Yield: 93.5%

$^1$H NMR (300 MHz/DMSO-d6) δ: 1.79 (d, 3H), 5.87 (q, 1H), 7.98 (d, 1H), 8.29 (dd, 1H), 8.65 (s, 1H)

EXAMPLE 3

5-(4-chloro-3-nitrophenyl)-6-methyl-3,6-dihydro-2H-1,3,4-thiadiazin-2-one

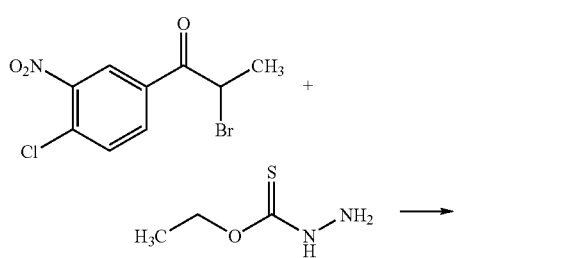

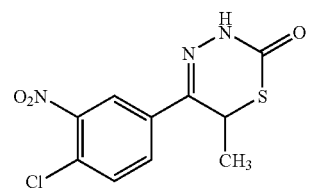

22 g (75 mM) of 1-(4-chloro-3-nitrophenyl)-2-bromopropan-1-one and 8 ml (75 mM) of O-ethyl hydrazinecarbothioate in 150 ml of ethanol are refluxed for 16 hours with stirring. The reaction medium is then concentrated under vacuum and the residue obtained is taken up in water. The aqueous phase is extracted twice with ethyl acetate and the combined organic phases are washed with water and then dried over anhydrous sodium sulfate. The solvent is evaporated off under vacuum to give an oil, which is purified on a column of silica using a dichloromethane/acetone mixture (95/5) as eluent. 5 g of 5-(4-chloro-3-nitrophenyl)-6-methyl-3,6-dihydro-2H-1,3,4-thiadiazin-2-one are obtained.

Yield: 23%

$^1$H NMR (300 MHz/CDCl$_3$) δ: 1.67 (d, 3H), 4.23 (q, 1H), 7.62 (d, 1H), 7.88 (dd, 1H), 8.23 (s, 1H), 9.04 (s, 1H)

EXAMPLE 4

5-[4-(isobutylamino)-3-nitrophenyl]-6-methyl-3,6-dihydro-2H-1,3,4-thiadiazin-2-one

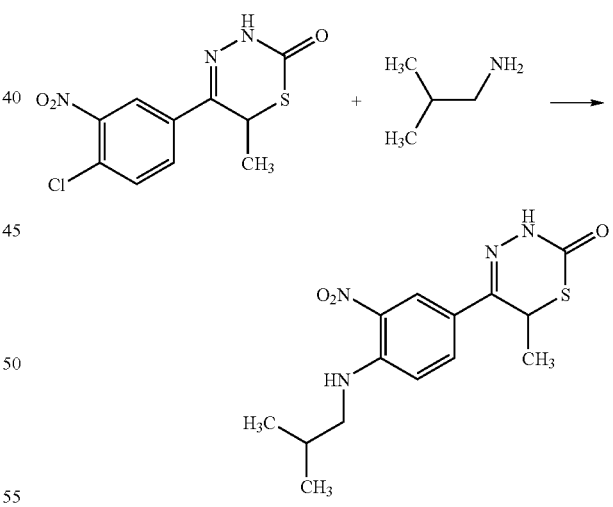

To 15 ml of acetonitrile are added 2.9 g (10.1 mM) of 5-(4-chloro-3-nitrophenyl)-6-methyl-3,6-dihydro-2H-1,3,4-thiadiazin-2-one and 5 ml (50 mM) of isobutylamine. The reaction medium is maintained at 60° C. for 20 hours with stirring and is then concentrated under vacuum. The residue obtained is purified on silica using dichloromethane as eluent. The product obtained is taken up and crystallised from diethyl ether. The solid is filtered off and washed to give 2.6 g of 5-[4-(isobutylamino)-3-nitrophenyl]-6-methyl-3,6-dihydro-2H-1,3,4-thiadiazin-2-one.

Yield: 80.6%

¹H NMR (300 MHz/CDCl₃) δ: 1.05 (d, 6H), 1.62 (d, 3H), 2.02 (m, 1H), 3.18 (t, 2H), 4.27 (q, 1H), 6.92 (d, 1H), 8.00 (dd, 1H), 8.4 (d, 1H), 8.46 (s, 1H), 9.10 (s, 1H)

EXAMPLE 5

5-[3-amino-4-(isobutylamino)phenyl]-6-methyl-3,6-dihydro-2H-1,3,4-thiadiazin-2-one

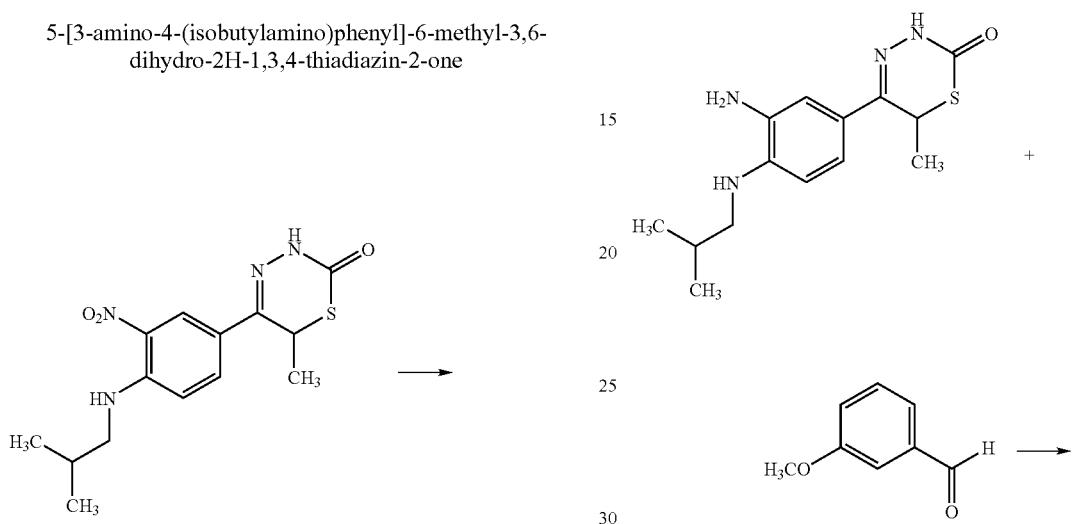

EXAMPLE 6

5-[1-isobutyl-2-(3-methoxyphenyl)-1H-benzimidazol-5-yl]-6-methyl-3,6-dihydro-2H-1,3,4-thiadiazin-2-one

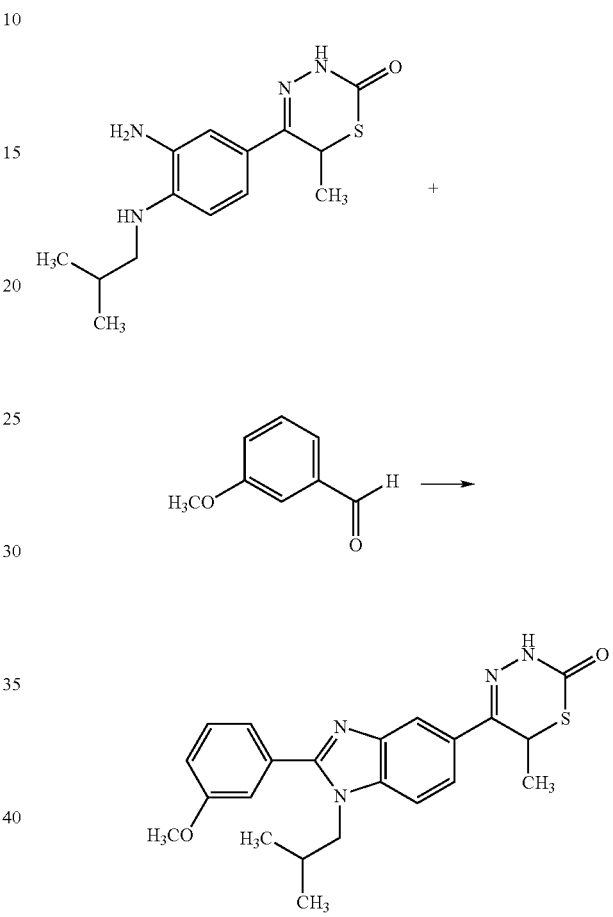

1.3 g (4.03 mM) of 5-{4-(isobutylamino)-3-nitrophenyl}-6-methyl-3,6-dihydro-2H-1,3,4-thiadiazin-2-one are added with stirring to 40 ml of acetic acid. To the solution obtained are added portionwise, over 45 minutes, 1.7 g (26 mM) of zinc. The reaction medium is then poured gently into 300 ml of saturated aqueous sodium hydrogen carbonate solution and 200 ml of dichloromethane.

Neutralisation is completed by adding sodium hydrogen carbonate. The organic phase is separated out by settling, washed with demineralised water and then dried over anhydrous sodium sulfate. After evaporation, 1.1 g of 5-[3-amino-4-(isobutylamino)phenyl]-6-methyl-3,6-dihydro-2H-1,3,4-thiadiazin-2-one are obtained.

Yield: 93%.

¹H NMR (300 MHz/CDCl₃) δ: 1.02 (d, 6H), 1.63 (d, 3H), 1.96 (m, 1H), 2.96 (d, 2H), 3.4 (s, 2H), 3.75 (s, 1H), 4.25 (q, 1H), 6.60 (d, 1H), 7.2 (dd, 1H), 7.28 (s, 1H), 9.27 (s, 1H)

To 12 ml of 1-methyl-2-pyrrolidone are added 560 mg (4.1 mM) of 4-methoxybenzaldehyde, 1.2 g (4.1 mM) of 5-[3-amino-4-(isobutylamino)phenyl]-6-methyl-3,6-dihydro-2H-1,3,4-thiadiazin-2-one and 780.2 mg (4.1 mM) of sodium bisulfite. The reaction medium is then maintained at 110° C. with stirring for 3 hours. The reaction medium is then poured into an ice/water mixture.

The resulting mixture is extracted with ethyl acetate and the organic phase is washed with demineralised water and then dried over anhydrous sodium sulfate. The solvent is evaporated off under vacuum to give an oil, which is purified on a column of silica using a heptane/ethyl acetate mixture (80/20) as eluent to give 960 mg of 5-[1-Isobutyl-2-(3-methoxyphenyl)-1H-benzimidazol-5-yl]-6-methyl-3,6-dihydro-2H-1,3,4-thiadiazin-2-one.

Yield: 57.3%

¹H NMR (300 MHz/CDCl₃) δ: 0.68 (d, 6H), 1.63 (d, 3H), 2.04 (m, 1H), 3.81 (s, 3H), 4.07 (d, 2H), 4.33 (m, 1H), 6.99 (d, 1H), 7.21 (s, 1H), 7.37 (m, 2H), 7.75 (m, 1H), 8.09 (s, 1H), 9.47 (s, 1H)

Melting point: 100-105° C.
$C_{22}H_{24}N_4O_2S=408.52$
Mass spectrometry M+1=409.1

The following compounds are prepared via a similar or slightly modified method:

EXAMPLE 6-2

5-[1-cyclopropylmethyl-2-(3-methoxyphenyl)-1H-benzimidazol-5-yl]-6-methyl-3,6-dihydro-2H-1,3,4-thiadiazin-2-one

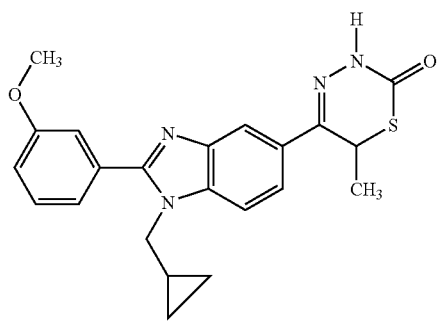

$C_{22}H_{22}N_4O_2S=406.5$
Mass spectrometry M+1=407.2

EXAMPLE 6-3

5-[2-(3-methoxyphenyl)-1-methyl-1H-benzimidazol-5-yl]-6-methyl-3,6-dihydro-2H-1,3,4-thiadiazin-2-one

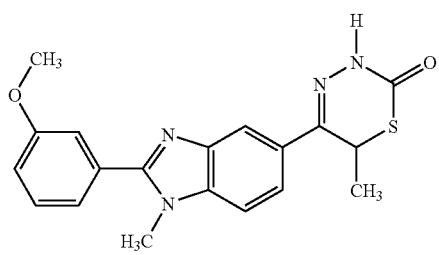

$C_{19}H_{18}N_4O_2S=366.4$
Mass spectrometry M+1=367.1

EXAMPLE 6-4

5-[1-Benzyl-2-(4-methoxyphenyl)-1H-benzimidazol-5-yl]-6-methyl-3,6-dihydro-2H-1,3,4-thiadiazin-2-one

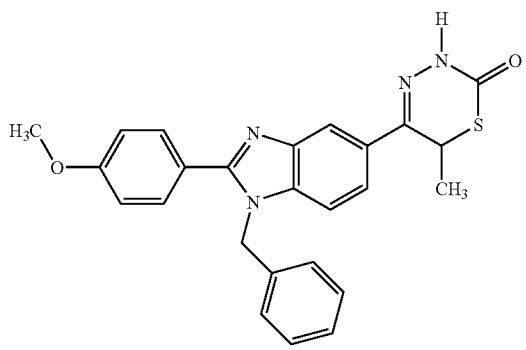

$C_{25}H_{22}N_4O_2S=442.53$
Mass spectrometry M+1=443.0

EXAMPLE 6-5

5-[2-(2-methoxyphenyl)-1-methyl-1H-benzimidazol-5-yl]-6-methyl-3,6-dihydro-2H-1,3,4-thiadiazin-2-one

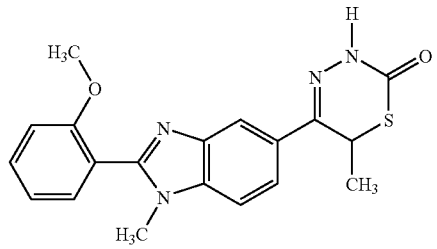

$C_{19}H_{18}N_4O_2S=366.44$
Mass spectrometry M+1=367.1

EXAMPLE 6-6

5-[2-(3-fluorophenyl)-1-methyl-1H-benzimidazol-5-yl]-6-methyl-3,6-dihydro-2H-1,3,4-thiadiazin-2-one

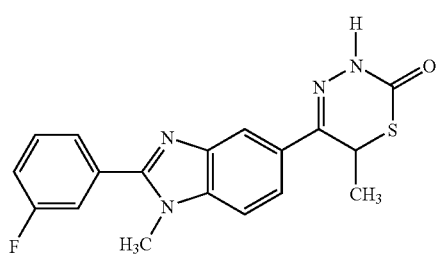

$C_{18}H_{15}FN_4OS=354.4$
Mass spectrometry M+1=355.1

EXAMPLE 7

1-[4-(isobutylamino)-3-nitrophenyl]ethanone

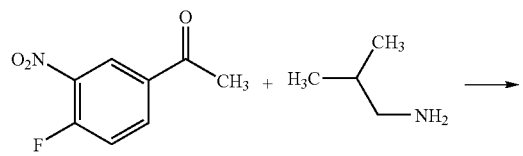

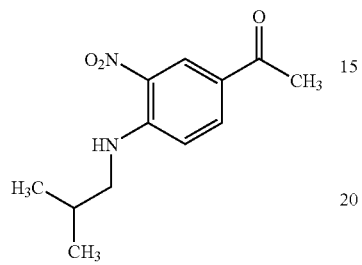

To 24.5 g (133.8 mM) of 1-(4-fluoro-3-nitrophenyl)ethanone in 100 ml of acetonitrile and 11.2 g (133.8 mM) of sodium hydrogen carbonate are added 26.6 ml (267.6 mM) of isobutylamine. The reaction is exothermic: the temperature of the reaction medium is maintained below 50° C. and the resulting mixture is then stirred for 1 hour at room temperature. Demineralised water is added, and a solid precipitates out. The solid is filtered off and washed with water to give after drying 31.6 g of 1-[4-(isobutylamino)-3-nitrophenyl]ethanone in quantitative yield.

$^1$H NMR (300 MHz/DMSO-d6) δ: 1.17 (d, 6H), 2.16 (m, 1H), 2.71 (s, 3H), 3.46 (t, 2H), 7.3 (d, 1H), 8.21 (d, 1H), 8.97 (s, 1H)

EXAMPLE 8

1-[3-amino-4-(isobutylamino)phenyl]ethanone

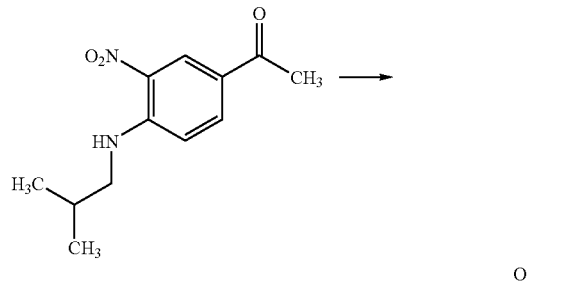

To a solution of 31.6 g (134 mM) of 1-[4-(isobutylamino)-3-nitrophenyl]-ethanone in 400 ml of methanol are added 3.2 g of 10% palladium-on-charcoal. The reaction medium is then placed under a hydrogen atmosphere at ambient pressure with vigorous stirring for 1 hour. The reaction medium is filtered through Celite and the solvent is evaporated off under vacuum to give 27.6 g of 1-[3-amino-4-(isobutylamino)phenyl]ethanone in quantitative yield, in the form of an oil.

$^1$H NMR (300 MHz/DMSO-d6) δ: 1.16 (d, 6H), 2.11 (m, 1H), 2.58 (s, 3H), 3.16 (t, 2H), 4.97 (s, 2H), 5.54 (s, 1H), 6.64 (d, 1H), 7.37 (s, 1H), 7.42 (d, 1H)

EXAMPLE 9

1-[1-(isobutyl)-2-(3-methoxyphenyl)-1H-benzimidazol-5-yl]ethanone

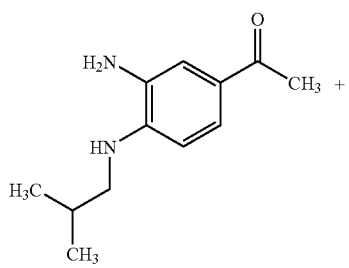

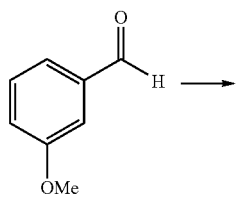

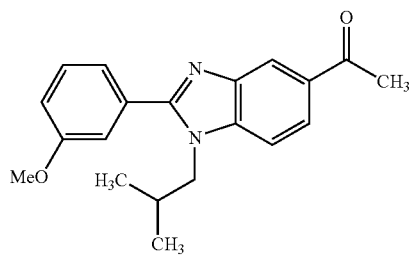

To 276 ml of 1-methyl-2-pyrrolidone are added 27.6 g (134 mM) of 1-[3-amino-4-(isobutylamino)phenyl]ethanone, 16.3 ml (134 mM) of 3-methoxybenzaldehyde and 25.4 g (134 mM) of sodium bisulfite. The reaction medium is maintained at 130° C. with stirring for 18 hours, and, after cooling, is added to an ice/water mixture. The resulting mixture is extracted with ethyl acetate and the organic phase is washed with water and then dried over anhydrous sodium sulfate. The resulting solution is evaporated under vacuum and the residue is purified on a column of silica, using a dichloromethane/acetone mixture (90/10) as eluent.

32.1 g of 1-[1-isobutyl-2-(3-methoxyphenyl)-1H-benzimidazol-5-yl]ethanone are obtained in the form of an oil. Yield: 74.4%

$^1$H NMR (300 MHz/DMSO-d6) δ: 1.07 (d, 6H), 2.29 (m, 1H), 3.07 (s, 3H), 4.25 (s, 3H), 4.66 (d, 2H), 7.57 (dd, 1H), 7.76 (m, 2H), 7.87 (t, 1H), 8.15 (d, 1H), 8.36 (d, 1H), 8.79 (s, 1H)

EXAMPLE 10

2-bromo-1-[1-isobutyl-2-(3-methoxyphenyl)-1H-benzimidazol-5-yl]-ethanone

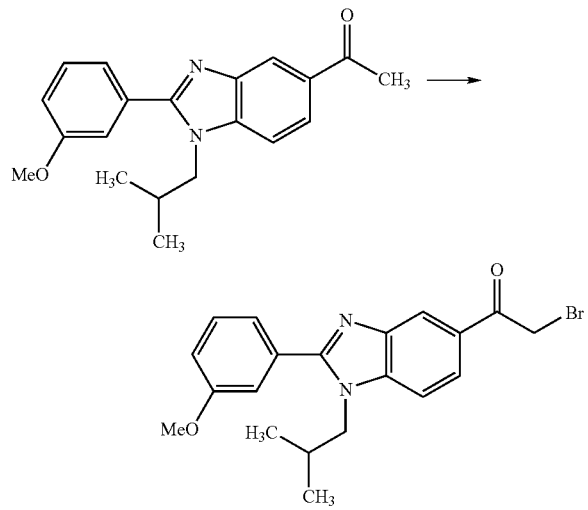

To a solution of 32.7 g (91.3 mM) of 1-[1-isobutyl-2-(3-methoxy phenyl)-1H-benzimidazol-5-yl]ethanone hydrochloride in 330 ml of acetic acid are added dropwise 4.7 ml (91.4 mM) of bromine. 100 ml of diethyl ether are then added and the crystalline product is filtered off. It is washed with diethyl ether and dried under vacuum to give 35 g of 2-bromo-1-[1-isobutyl-2-(3-methoxyphenyl)-1H-benzimidazol-5-yl]ethanone hydrochloride.

Yield: 63.2%

$C_{20}H_{21}BrN_2O_2$=401.3

Mass spectrometry M+1=403.1

EXAMPLE 11

5-[1-isobutyl-2-(3-methoxyphenyl)-1H-benzimidazol-5-yl]-3,6-dihydro-2H-1,3,4-thiadiazin-2-one

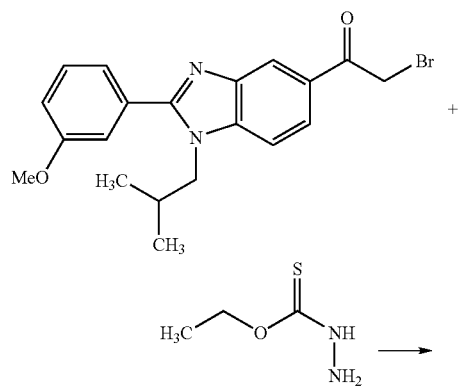

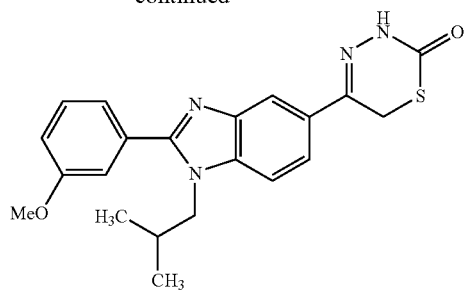

To a solution of 24 g (54.8 mM) of 2-bromo-1-[1-isobutyl-2-(3-methoxyphenyl)-1H-benzimidazol-5-yl]ethanone hydrochloride in 500 ml of ethanol are added 6.3 ml (78.4 mM) of pyridine and then 8.2 g (78.4 mM) of O-ethyl hydrazinecarbothioate. The reaction medium is then maintained at 80° C. with stirring for 20 hours. Water is then added and the resulting mixture is extracted with ethyl acetate. The organic phase is washed with water and then dried over anhydrous sodium sulfate and evaporated under vacuum. The residue is purified on a column of silica, using a dichloromethane/methanol mixture (98/2). The residue obtained after evaporation is taken up in diethyl ether to give, after filtration, 10 g of 5-[1-isobutyl-2-(3-methoxyphenyl)-1H-benzimidazol-5-yl]-3,6-dihydro-2H-1,3,4-thiadiazin-2-one in the form of a light-beige solid.

Yield: 46.2%

$^1$H NMR (300 MHz/DMSO-d6) δ: 0.65 (d, 6H), 1.90 (m, 1H), 3.83 (s, 3H), 4.20 (d, 2H), 4.32 (s, 2H), 7.14 (dd, 1H), 7.32 (m, 2H), 7.48 (t, 1H), 7.77 (m, 2H), 8.14 (d, 1H), 11.56 (s, 1H)

Melting point: 207-209° C.

$C_{21}H_{22}N_4O_2S$=394.55

Mass spectrometry M+1=395.1

The following compounds are prepared via a similar or slightly modified method:

EXAMPLE 11-2

5-[2-(3-fluorophenyl)-1-methyl-1H-benzimidazol-5-yl]-3,6-dihydro-2H-1,3,4-thiadiazin-2-one

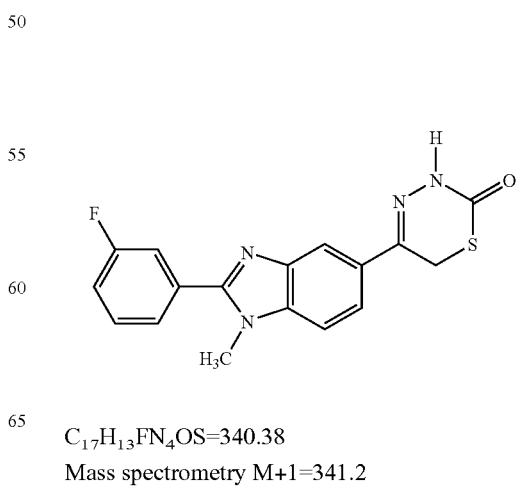

$C_{17}H_{13}FN_4OS$=340.38

Mass spectrometry M+1=341.2

EXAMPLE 11-3

5-{1-methyl-2-[3-(trifluoromethyl)phenyl]-1H-benzimidazol-5-yl}-3,6-dihydro-2H-1,3,4-thiadiazin-2-one

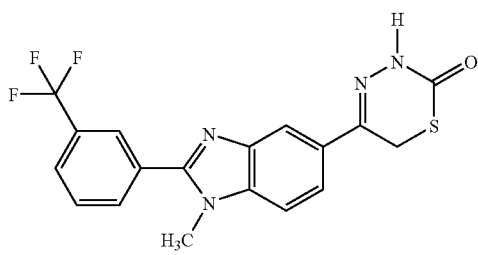

$C_{18}H_{13}F_3N_4OS=390.38$
Mass spectrometry M+1=391.1

EXAMPLE 11-4

5-[1-ethyl-2-(3-fluorophenyl)-1H-benzimidazol-5-yl]-3,6-dihydro-2H-1,3,4-thiadiazin-2-one

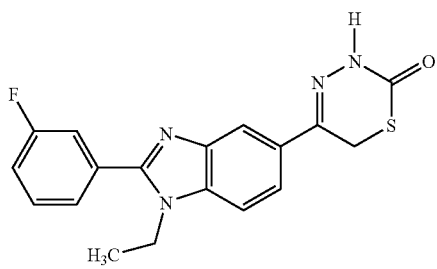

$C_{18}H_{15}FN_4OS=354.4$
Mass spectrometry M+1=355.1
Melting point: 214-216° C.

EXAMPLE 11-5

5-{1-methyl-2-[3-(trifluoromethyl)phenyl]-1H-benzimidazol-5-yl}-6-propyl-3,6-dihydro-2H-1,3,4-thiadiazin-2-one

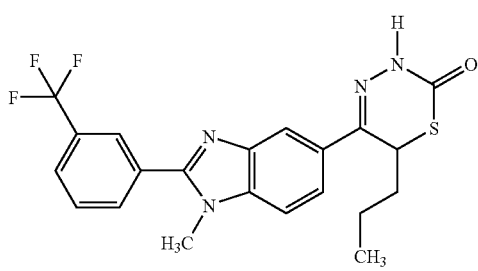

$C_{21}H_{19}F_3N_4OS=432.46$
Mass spectrometry M+1=433.1
Melting point: 190-192° C.

EXAMPLE 11-6

5-[1-ethyl-2-(3-methoxyphenyl)-1H-benzimidazol-5-yl]-3,6-dihydro-2H-1,3,4-thiadiazin-2-one

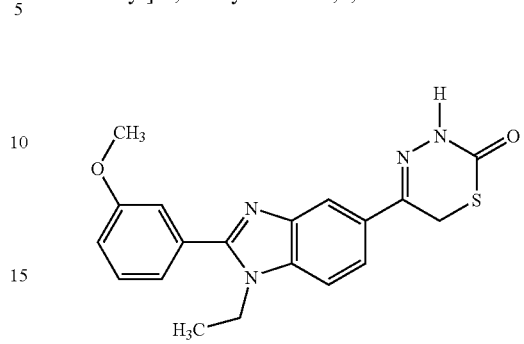

$C_{19}H_{18}N_4O_2S=366.44$
Mass spectrometry M+1=367.1
Melting point: 221-223° C.

EXAMPLE 12

3-Isopropyl-6-methyl-5-{1-methyl-2-[(3-trifluoromethyl)phenyl]-1H-benzimidazol-5-yl}-3,6-dihydro-2H-1,3,4-thiadiazin-2-one

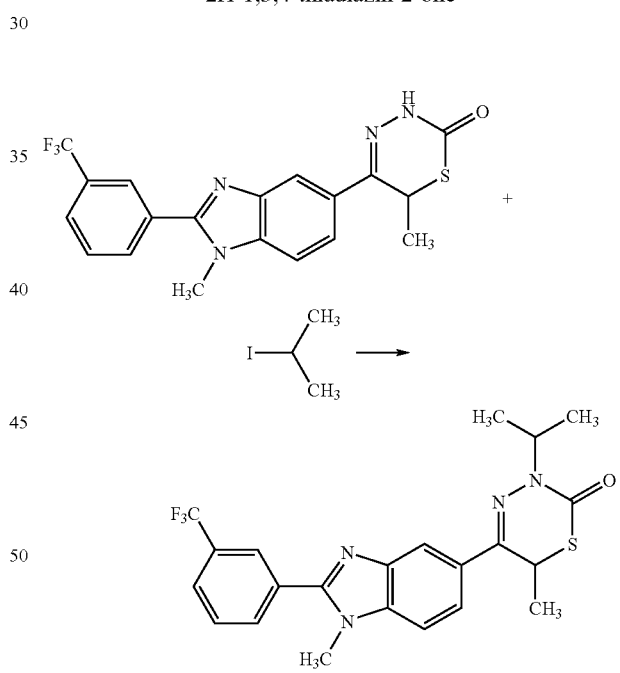

To 2 ml of dimethylformamide are added 200 mg (0.49 mM) of 6-methyl-5-{1-methyl-2-[(3-trifluoromethyl)phenyl]-1H-benzimidazol-5-yl}-3,6-dihydro-2H-1,3,4-thiadiazin-2-one, 168.3 mg (0.99 mM) of isopropyl iodide and 484 mg (1.48 mM) of caesium carbonate. The reaction medium is stirred at room temperature for 16 hours. 5 ml of water are added and the resulting mixture is extracted with 5 ml of ethyl acetate.

The organic phase is washed with water, dried over anhydrous sodium sulfate and then concentrated under vacuum to give an oil, which is purified by chromatography on silica, using a dichloromethane/acetone mixture (98/2) as eluent. 200 mg of 3-Isopropyl-6-methyl-5-{1-methyl-2-[(3-trifluoromethyl)phenyl]-1H-benzimidazol-5-yl}-3,6-dihydro-2H-1,3,4-thiadiazin-2-one are obtained in the form of an oil.

Yield: 90.5%

$^1$H NMR (300 MHz/DMSO-d6) δ: 1.26 (d, 3H), 1.36 (d, 3H), 1.54 (d, 3H), 3.98 (s, 3H), 4.94 (m, 2H), 7.95 (m, 4H), 8.25 (m, 3H)

$C_{22}H_{21}F_3N_4OS=446.49$

Mass spectrometry M+1=447.1

The following compounds are prepared via a similar or slightly modified method:

EXAMPLE 12-2

2-[5-[2-(3-methoxyphenyl)-1-methyl-1H-benzimidazol-5-yl]-6-methyl-2-oxo-2H-1,3,4-thiadiazin-3(6H)-yl]acetamide

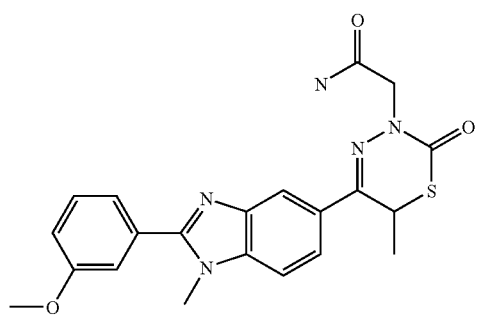

$C_{21}H_{21}N_5O_3S=423.49$

Mass spectrometry M+1=424.1

EXAMPLE 12-3

5-[2-(3-fluorophenyl)-1-methyl-1H-benzimidazol-5-yl]-3-isopropyl-6-methyl-3,6-dihydro-2H-1,3,4-thiadiazin-2-one

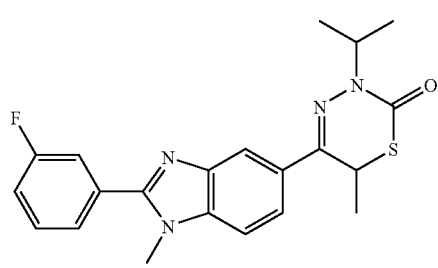

$^1$H NMR (300 MHz/DMSO-d6) δ: 1.30 (d, 3H), 1.40 (d, 3H), 1.58 (d, 3H), 4.01 (s, 3H), 4.98 (m, 2H), 7.51 (m, 1H), 7.70 (m, 1H), 7.81 (m, 3H), 7.99 (m, 1H), 8.27 (s, 1H)

$C_{21}H_{21}FNO_4S=396.48$

Mass spectrometry M+1=397.1

EXAMPLE 12-4

3-isobutyl-5-{1-methyl-2-[3-(trifluoromethyl)phenyl]-1H-benzimidazol-5-yl}-6-propyl-3,6-dihydro-2H-1,3,4-thiadiazin-2-one

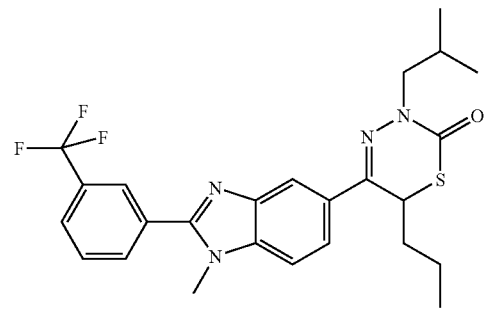

$C_{25}H_{27}F_3N_4OS=488.58$

Mass spectrometry M+1=489.0

EXAMPLE 12-5

3-(cyclohexylmethyl)-5-[2-(2-furyl)-1-methyl-1H-benzimidazol-5-yl]-3,6-dihydro-2H-1,3,4-thiadiazin-2-one

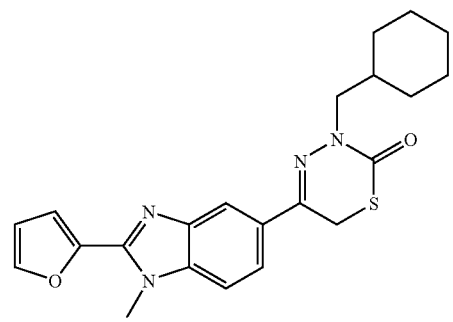

$C_{22}H_{24}N_4O_2S=408.53$

Mass spectrometry M+1=409.2

EXAMPLE 12-6

5-[2-(3-fluorophenyl)-1-methyl-1H-benzimidazol-5-yl]-6-methyl-3-propyl-3,6-dihydro-2H-1,3,4-thiadiazin-2-one

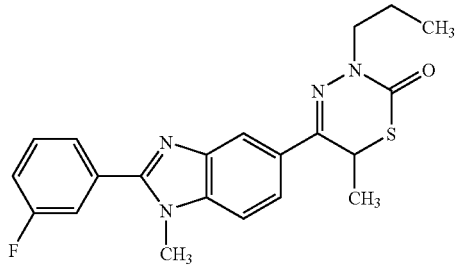

$C_{21}H_{21}FN_4OS=396.48$

Mass spectrometry M+1=397.1

EXAMPLE 12-7

5-[1-cycloheptyl-2-(3-methoxyphenyl)-1H-benzimidazol-5-yl]-3-methyl-3,6-dihydro-2H-1,3,4-thiadiazin-2-one

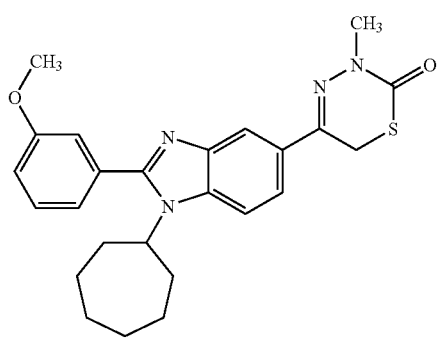

$^1$H NMR (300 MHz/DMSO-d6) δ: 1.59 (m, 6H), 1.86 (m, 2H), 2.10 (m, 2H), 2.93 (m, 2H), 3.48 (s, 3H), 3.89 (s, 3H), 4.43 (s, 2H), 4.53 (m, 1H), 7.39 (m, 3H), 7.66 (t, 1H), 8.02 (d, 1H), 8.16 (d, 1H), 8.24 (s, 1H)

$C_{25}H_{28}N_4O_2S=448.59$

Mass spectrometry M+1=449.1

EXAMPLE 13 tert-butyl 2-[5-[2-(3-fluorophenyl)-1-methyl-1H-benzimidazol-5-yl]-6-methyl-2-oxo-2H-1,3,4-thiadiazin-3(6H)-yl]ethylcarbamate

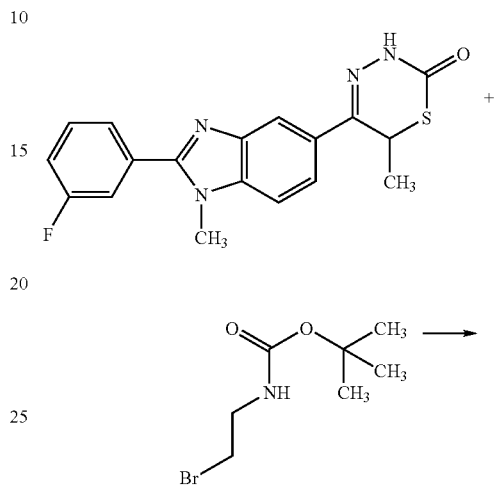

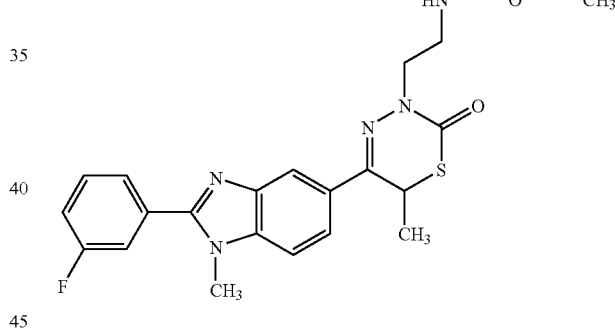

4.9 g (14 mM) of 5-[2-(3-fluorophenyl)-1-methyl)-1H-benzimidazol-5-yl]-6-methyl-3,6-dihydro-2H-1,3,4-thiadiazin-2-one, 3.4 g (15 mM) of 2-(Boc-amino)ethyl bromide and 16.6 g (42 mM) of caesium carbonate are added to 40 ml of dimethylformamide. The mixture is stirred at room temperature for 20 hours, and 200 ml of demineralised water are then added. A whitish precipitate forms, which is filtered off. After washing with water and drying, 6.3 g of tert-butyl 2-[5-[2-(3-fluorophenyl)-1-methyl-1H-benzimidazol-5-yl]-6-methyl-2-oxo-2H-1,3,4-thiadiazin-3(6H)-yl]ethylcarbamate are obtained.

Yield: 90.8%

$^1$H NMR (300 MHz/DMSO-d6) δ: 1.35 (s, 9H), 1.56 (d, 3H), 3.37 (m, 2H), 3.83 (m, 1H), 3.97 (s, 3H), 4.14 (m, 1H), 4.94 (q, 1H), 6.99 (t, 1H), 7.46 (t, 1H), 7.74 (m, 4H), 7.91 (d, 1H), 8.22 (s, 1H)

$C_{25}H_{28}FN_5O_3S=497.59$

Mass spectrometry M+1=498

EXAMPLE 14

3-(2-aminoethyl)-5-[2-(3-fluorophenyl)-1-methyl-1H-benzimidazol-5-yl]-6-methyl-3,6-dihydro-2H-1,3,4-thiadiazin-2-one

EXAMPLE 15

N-(4-chlorophenyl)-N'-{3-[5-[2-(2-furyl)-1-methyl-1H-benzimidazol-5-yl]-2-oxo-2H-1,3,4-thiadiazin-3(6H)-yl]propyl}urea

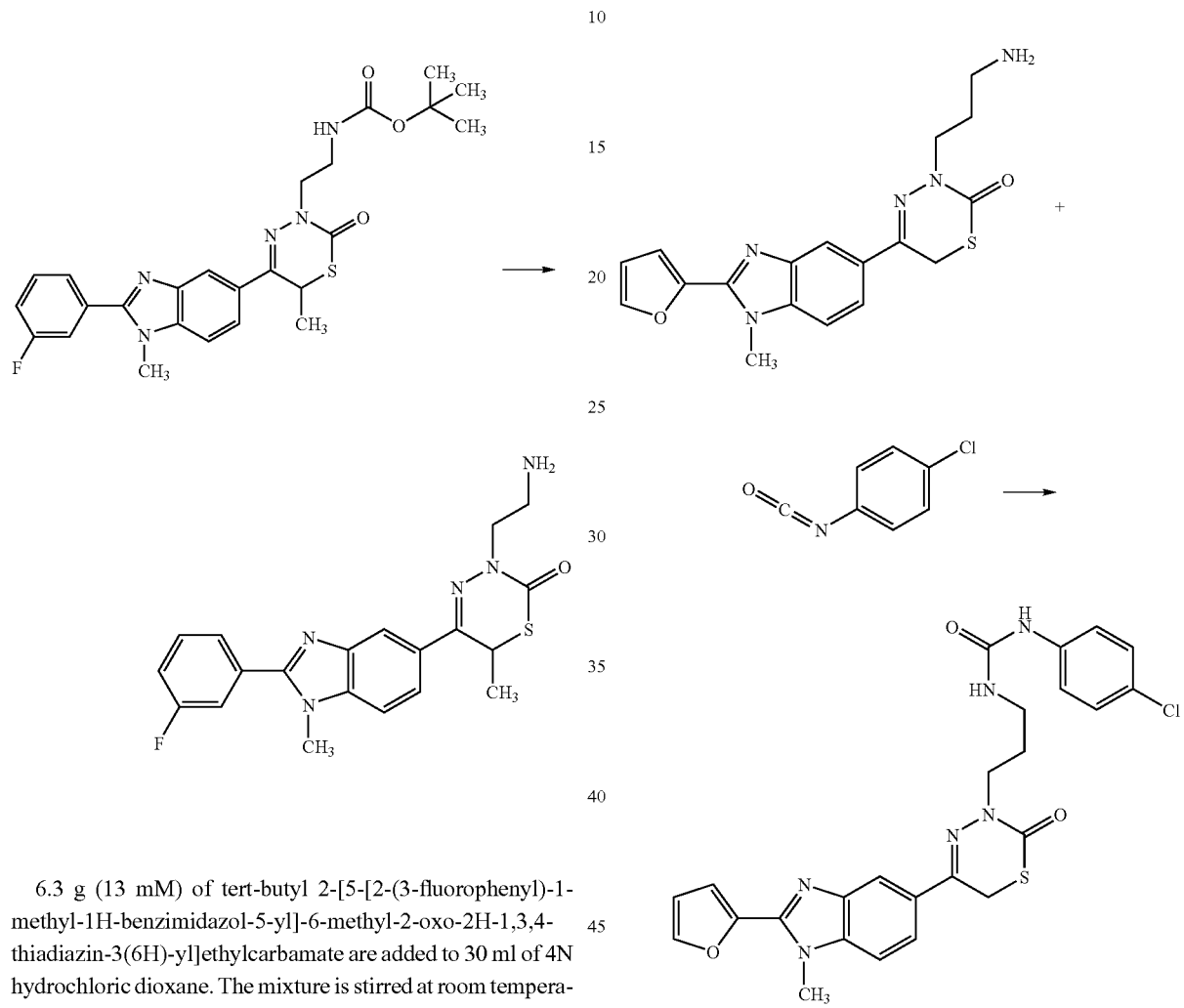

6.3 g (13 mM) of tert-butyl 2-[5-[2-(3-fluorophenyl)-1-methyl-1H-benzimidazol-5-yl]-6-methyl-2-oxo-2H-1,3,4-thiadiazin-3(6H)-yl]ethylcarbamate are added to 30 ml of 4N hydrochloric dioxane. The mixture is stirred at room temperature for 20 hours. The crystalline solid, which is the hydrochloride of the desired compound, is filtered off. The free base is obtained via the action of aqueous sodium hydrogen carbonate solution and extraction with ethyl acetate. The aqueous phase is washed with water and then dried over sodium sulfate and concentrated under vacuum to give 3.85 g of 3-(2-aminoethyl)-5-[2-(3-fluorophenyl)-1-methyl-1H-benzimidazol-5-yl]-6-methyl-3,6-dihydro-2H-1,3,4-thiadiazin-2-one in solid form.

Yield: 76.5%

$^1$H NMR (300 MHz/DMSO-d6) δ: 1.59 (d, 3H), 3.20 (m, 2H), 4.05 (s, 3H), 4.21 (m, 2H), 5.02 (m, 1H), 7.83 (m, 5H), 8.29 (m, 3H)

$C_{20}H_{20}FN_5OS=397.47$

Mass spectrometry M+1=398.0

120 mg (0.30 mM) of 3-(3-aminopropyl)-5-[2-(2-furyl)-1-methyl-1H-benzimidazol-5-yl]-3,6-dihydro-2H-1,3,4-thiadiazin-2-one and 50.1 mg (0.33 mM) of 1-chloro-4-isocyanatobenzene are added to 2 ml of THF and 164.33 μl (1.33 mM) of triethylamine. The mixture is stirred at room temperature for 20 hours. The solid is filtered off and washed with water and then with isopropanol to give, after drying, 106 mg of N-(4-chlorophenyl)-N'-{3-[5-[2-(2-furyl)-1-methyl-1H-benzimidazol-5-yl]-2-oxo-2H-1,3,4-thiadiazin-3(6H)-yl]propyl}urea.

Yield: 68%

$^1$H NMR (300 MHz/DMSO-d6) δ: 1.90 (t, 2H), 3.20 (q, 2H), 3.93 (t, 2H), 4.07 (s, 3H), 4.38 (s, 2H), 6.28 (t, 1H), 6.81 (m, 1H), 7.25 (d, 2H), 7.32 (d, 1H), 7.42 (d, 2H), 7.71 (d, 1H), 7.87 (d, 1H), 8.05 (s, 1H), 8.16 (s, 1H)

The following compounds are prepared via a similar or slightly modified method:

EXAMPLE 15-2

N-ethyl-N'-[2-[5-[1-methyl-2-[3-(trifluoromethyl)phenyl]-1H-benzimidazol-5-yl]-2-oxo-2H-1,3,4-thiadiazin-3(6H)-yl]ethyl]urea

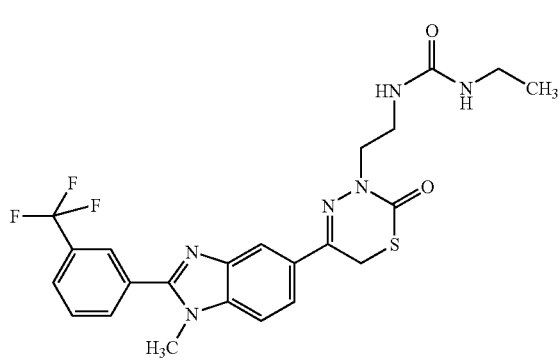

$C_{23}H_{23}F_3N_6O_2S=504.53$
Mass spectrometry M+1=505.1

EXAMPLE 15-3

N-benzyl-N'-{2-[5-[2-(2-furyl)-1-methyl-1H-benzimidazol-5-yl]-2-oxo-2H-1,3,4-thiadiazin-3(6H)-yl]ethyl}urea

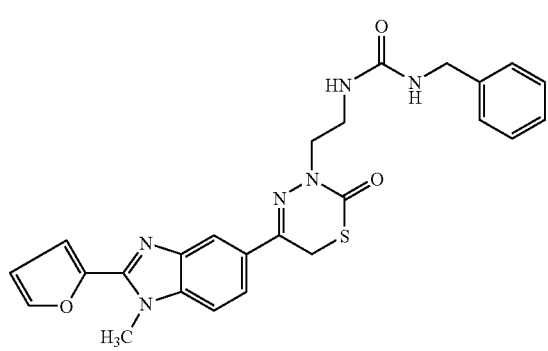

$C_{25}H_{24}N_6O_3S=488.56$
Mass spectrometry M+1=489.0

EXAMPLE 15-4

N-(2-fluorophenyl)-N'-{3-[5-[2-(2-furyl)-1-methyl-1H-benzimidazol-5-yl]-2-oxo-2H-1,3,4-thiadiazin-3(6H)-yl]propyl}urea

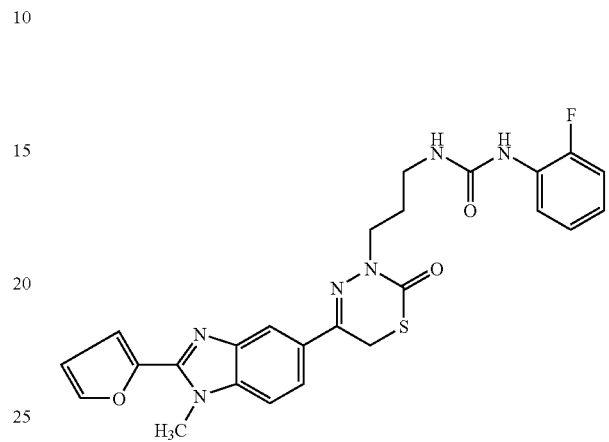

$C_{25}H_{23}FN_6O_3S=506.55$
Mass spectrometry M+1=507.0

EXAMPLE 15-5

N-(4-acetylphenyl)-N'-{2-[5-[2-(3-fluorophenyl)-1-methyl-1H-benzimidazol-5-yl]-6-methyl-2-oxo-2H-1,3,4-thiadiazin-3(6H)-yl]ethyl}urea

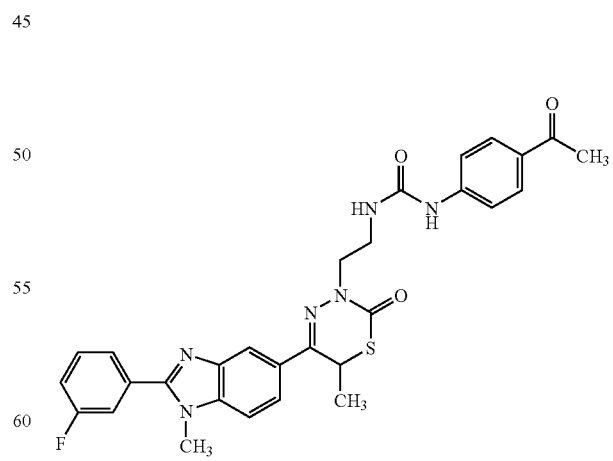

$C_{29}H_{27}FN_6O3S=558.63$
Mass spectrometry M+1=559.1

EXAMPLE 16

N-{2-[5-{1-methyl-2-[3-(trifluoromethyl)phenyl]-1H-benzimidazol-5-yl}-2-oxo-2H-1,3,4-thiadiazin-3(6H)-yl]ethyl}benzenesulfonamide

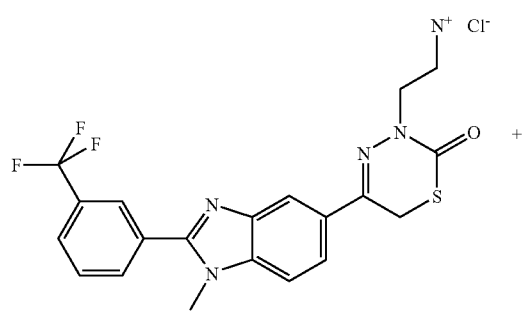

+

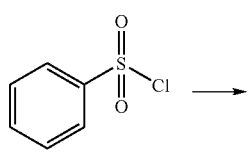

→

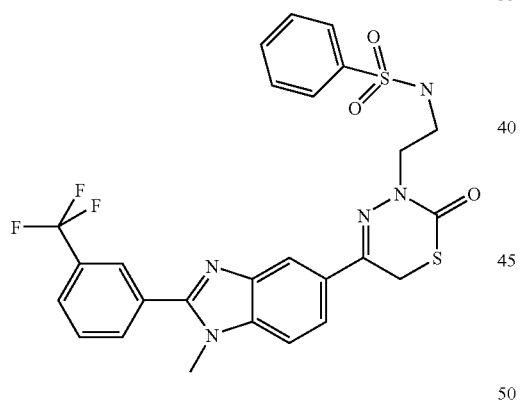

To 2 ml of dichloromethane in 177 µl (1.28 mM) of triethylamine are added 150 mg (0.32 mM) of 3-(2-aminoethyl)-5-{1-methyl-2-[3-(trifluoromethyl)phenyl]-1H-benzimidazol-5-yl}-3,6-dihydro-2H-1,3,4-thiadiazin-2-one hydrochloride and 67.7 µl (0.38 mM) of benzenesulfonyl chloride. The mixture is stirred at room temperature for 20 hours. The solid is filtered off and washed with water to give, after drying, 138 mg of N-{2-[5-{1-methyl-2-[3-(trifluoromethyl)phenyl]-1H-benzimidazol-5-yl}-2-oxo-2H-1,3,4-thiadiazin-3(6H)-yl]ethyl}benzenesulfonamide.

Yield: 75%

$^1$H NMR (300 MHz/DMSO-d6) δ: 3.14 (m, 2H), 3.93 (t, 2H), 4.02 (s, 3H), 4.37 (s, 2H), 7.32 (m, 1H), 7.61 (m, 3H), 7.81 (m, 1H), 7.91 (m, 3H), 8.03 (d, 2H), 8.24 (m, 3H)

$C_{26}H_{22}F_3N_5O_3S_2 = 573.61$

Mass spectrometry M+1=574.1

The following compounds are prepared via a similar or slightly modified method:

EXAMPLE 16-2

N-{2-[5-[2-(2-furyl)-1-methyl-1H-benzimidazol-5-yl]-2-oxo-2H-1,3,4-thiadiazin-3(6H)-yl]ethyl}butane-1-sulfonamide

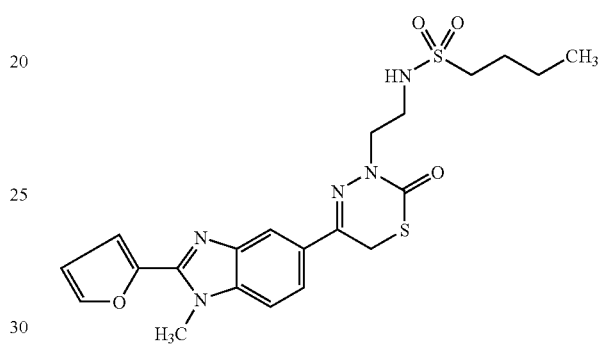

$C_{21}H_{25}N_5O_4S_2 = 475.59$

Mass spectrometry M+1=476.0

EXAMPLE 16-3

N-{2-[5-[2-(2-furyl)-1-methyl-1H-benzimidazol-5-yl]-2-oxo-2H-1,3,4-thiadiazin-3(6H)-yl]ethyl}methanesulfonamide

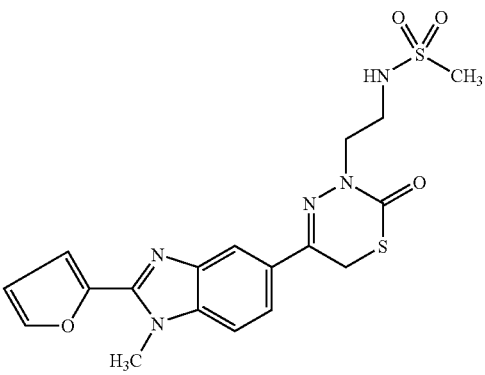

$C_{18}H_{19}N_5O_4S_2 = 433.51$

Mass spectrometry M+1=434.1

EXAMPLE 16-4

N-{2-[5-{1-methyl-2-[3-(trifluoromethyl)phenyl]-1H-benzimidazol-5-yl}-2-oxo-2H-1,3,4-thiadiazin-3(6H)-yl]ethyl}methanesulfonamide

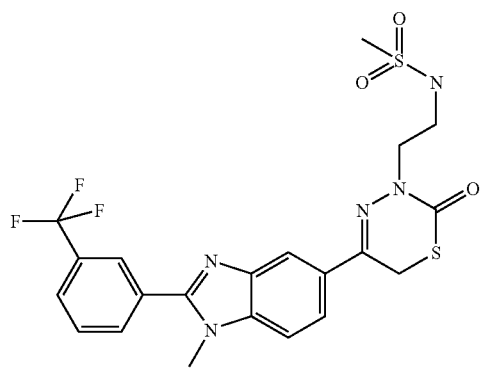

$C_{21}H_{20}F_3N_5O_3S_2=511.54$
Mass spectrometry M+1=512.0

EXAMPLE 17

N-{3-[5-[2-(2-furyl)-1-methyl-1H-benzimidazol-5-yl]-2-oxo-2H-1-1,3,4-thiadiazin-3(6H)-yl]ethyl}cyclopropanecarboxamide

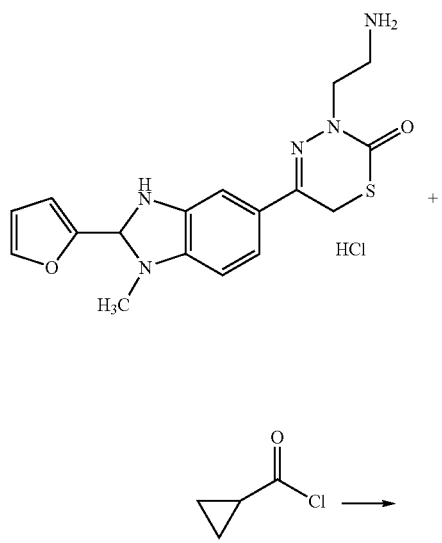

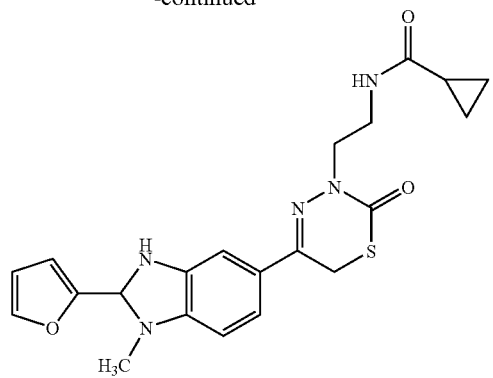

To 4 ml of THF and 212 μl (1.53 mM) of triethylamine are added 150 mg (0.38 mM) of 3-(2-aminoethyl)-5-[2-(2-furyl)-1-methyl-1H-benzimidazol-5-yl]-3,6-dihydro-2H-1,3,4-thiadiazin-2-one hydrochloride and 41.7 μl (0.46 mM) of cyclopropanecarbonyl chloride. The mixture is stirred at room temperature for 20 hours. The solid is filtered off and washed with water to give, after drying, 106 mg of N-{3-[5-[2-(2-furyl)-1-methyl-1H-benzimidazol-5-yl]-2-oxo-2H-1,3,4-thiadiazin-3(6H)-yl]ethyl}cyclopropanecarboxamide.

Yield: 65%

$^1$H NMR (300 MHz/DMSO-d6) δ: 0.66 (m, 4H), 1.51 (m, 1H), 3.43 (q, 2H), 3.95 (t, 2H), 4.08 (s, 3H), 4.34 (s, 2H), 6.80 (m, 1H), 7.33 (d, 1H), 7.77 (d, 1H), 7.88 (d, 1H), 8.05 (s, 1H), 8.17 (s, 1H), 8.23 (s, 1H)

$C_{21}H_{21}N_5O_3S=423.49$
Mass spectrometry M+1=424.1

The following compounds are prepared via a similar or slightly modified method:

EXAMPLE 17-2

N-{2-[5-{1-methyl-2-[3-(trifluoromethyl)phenyl]-1H-benzimidazol-5-yl}-2-oxo-2H-1,3,4-thiadiazin-3(6H)-yl]ethyl}acetamide

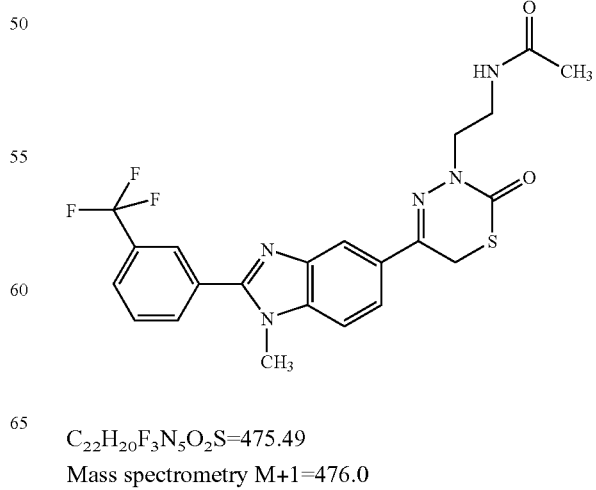

$C_{22}H_{20}F_3N_5O_2S=475.49$
Mass spectrometry M+1=476.0

EXAMPLE 17-3

N-{2-[5-[2-(3-fluorophenyl)-1-methyl-1H-benzimidazol-5-yl]-6-methyl-2-oxo-2H-1,3,4-thiadiazin-3(6H)-yl]ethyl}-4-methylbenzamide

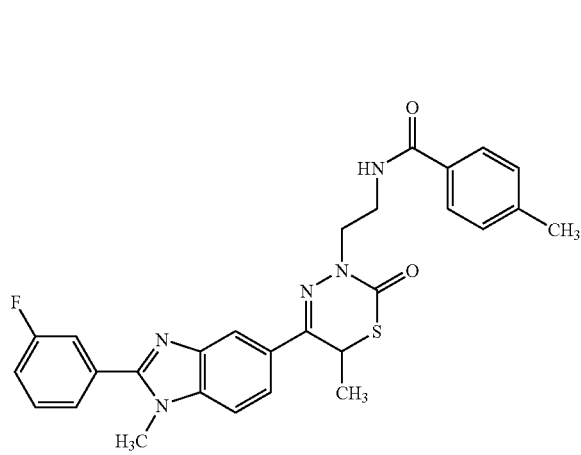

$C_{28}H_{26}FN_5O_2S=515.6$
Mass spectrometry M+1=516.2

EXAMPLE 17-4

N-{2-[5-[2-(2-furyl)-1-methyl-1H-benzimidazol-5-yl]-2-oxo-2H-1,3,4-thiadiazin-3(6H)-yl]ethyl}benzamide

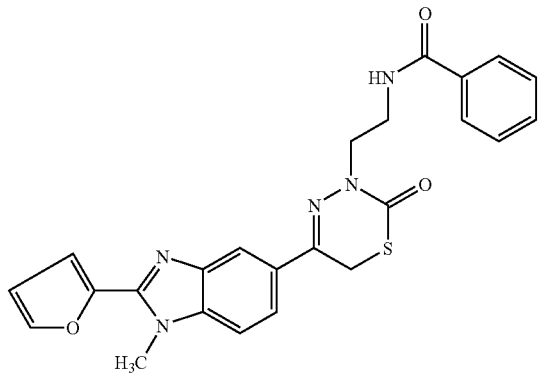

$C_{24}H_{21}N_5O_3S=459.52$
Mass spectrometry M+1=460.1

EXAMPLE 17-5

N-{3-[5-[2-(2-furyl)-1-methyl-1H-benzimidazol-5-yl]-2-oxo-2H-1,3,4-thiadiazin-3(6H)-yl]propyl}benzamide

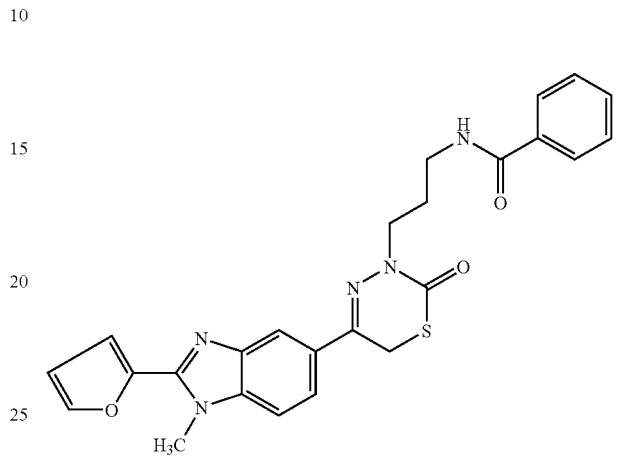

$C_{25}H_{23}N_5O_3S=473.55$
Mass spectrometry M+1=474.0

EXAMPLE 18

5-[1-ethyl-2-(3-methoxyphenyl)-1H-benzimidazol-5-yl]-3-[2-(tetrahydro-2H-pyran-2-yloxy)ethyl]-3,6-dihydro-2H-1,3,4-thiadiazin-2-one

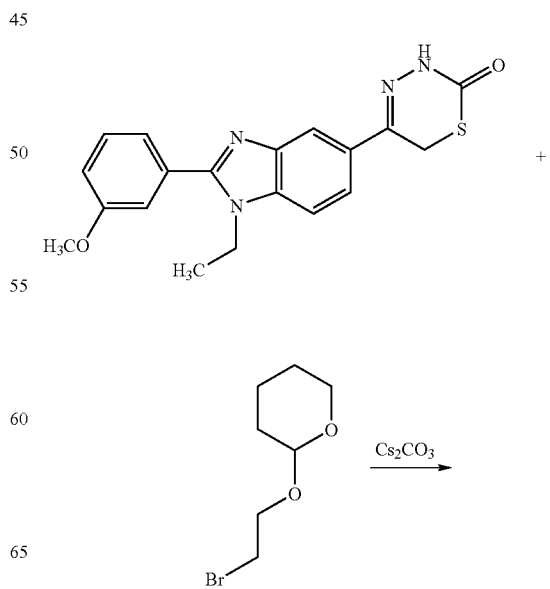

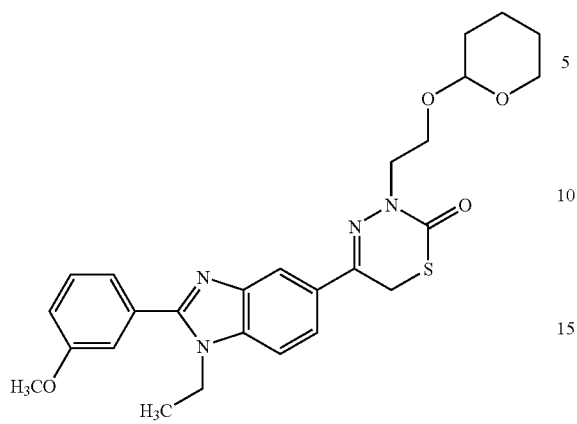

To 200 mg (0.55 mM) of 5-[1-ethyl-2-(3-methoxyphenyl)-1H-benzimidazol-5-yl]-3,6-dihydro-2H-1,3,4-thiadiazin-2-one in 4 ml of dimethylformamide are added 91 μl (0.6 mM) of 2-(2-bromoethoxy)tetrahydro-2H-pyran and 533.5 mg (1.64 mM) of caesium carbonate. The reaction medium is then stirred at room temperature for 16 hours. Demineralised water is added and the organic phase is isolated, washed with demineralised water and then dried over anhydrous sodium sulfate. The solvent is then evaporated off under vacuum and the residue is purified by chromatography on silica, using a dichloromethane/acetone mixture (90/10) as eluent, to give 200 mg of 5-[1-ethyl-2-(3-methoxyphenyl)-1H-benzimidazol-5-yl]-3-[2-(tetrahydro-2H-pyran-2-yloxy)ethyl]-3,6-dihydro-2H-1,3,4-thiadiazin-2-one in the form of an oil.

Yield: 74%

$C_{26}H_{30}N_4O_4S = 494.61$

Mass spectrometry M+1=495.2

EXAMPLE 19

5-[1-ethyl-2-(3-methoxyphenyl)-1H-benzimidazol-5-yl]-3-(2-hydroxyethyl)-3,6-dihydro-2H-1,3,4-thiadiazin-2-one

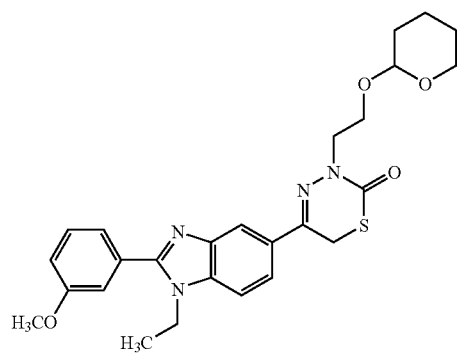

HCl/H₂O/MeOH →

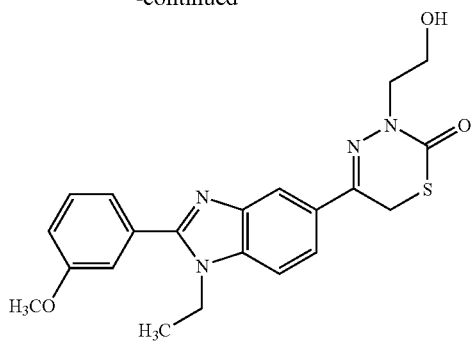

200 mg (0.40 mM) of 5-[1-ethyl-2-(3-methoxyphenyl)-1H-benzimidazol-5-yl]-3-[2-(tetrahydro-2H-pyran-2-yloxy)ethyl]-3,6-dihydro-2H-1,3,4-thiadiazin-2-one and 50 μl (0.6 mM) of 37% hydrochloric acid in 2 ml of methanol are stirred for 16 hours at room temperature. The solvent is evaporated off under vacuum and the residue obtained is taken up in aqueous sodium hydrogen carbonate solution. The resulting mixture is extracted with ethyl acetate and the organic phase is washed with demineralised water and then dried over anhydrous sodium sulfate. The solvent is evaporated off under vacuum to give an oil, which is purified by chromatography on silica, using a dichloromethane/acetone mixture (90/10) as eluent, to give 119 mg of 5-[1-ethyl-2-(3-methoxyphenyl)-1H-benzimidazol-5-yl]-3-(2-hydroxyethyl)-3,6-dihydro-2H-1,3,4-thiadiazin-2-one in the form of an oil that crystallises.

Yield: 72%

¹H NMR (300 MHz/DMSO-d6) δ: 1.40 (t, 3H), 3.74 (t, 2H), 3.91 (s, 3H), 4.00 (t, 2H), 4.42-4.44 (m, 2×2H), 7.24 (d, 1H), 7.38 (m, 2H), 7.58 (m, 1H), 7.85 (d, 1H), 7.93 (d, 1H), 8.26 (s, 1H)

$C_{21}H_{22}N_4O_3S = 410.49$

Mass spectrometry M+1=411.1

EXAMPLE 20

N-(4-propanoylphenyl)acetamide

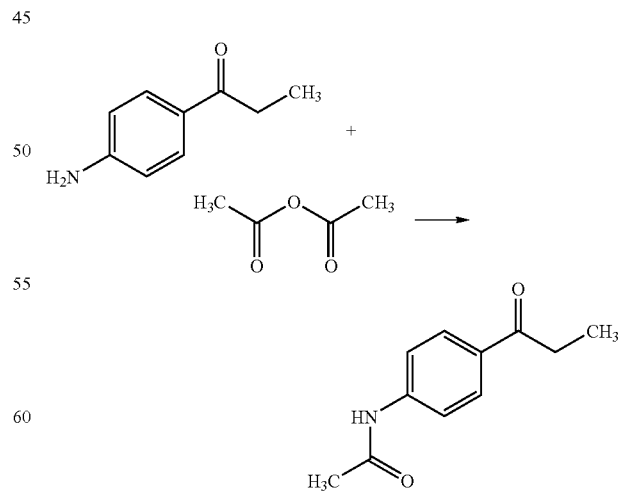

To 400 ml of toluene are added 30 g of 1-(4-aminophenyl)propan-1-one and 38 ml (402 mM) of acetic anhydride. The reaction medium is heated at 60° C. with stirring for 1 hour. A solid precipitates out. After filtration and washing with toluene, 37.9 g of N-(4-propanoylphenyl)acetamide are obtained in the form of a white powder.

Yield: 99%

$^1$H NMR (300 MHz/DMSO-d6) δ: 1.08 (t, 3H), 2.10 (s, 3H), 3.00 (q, 2H), 7.73 (d, 2H) 7.92 (d, 2H), 10.29 (s, 1H)

EXAMPLE 21

N-(2-nitro-4-propanoylphenyl)acetamide

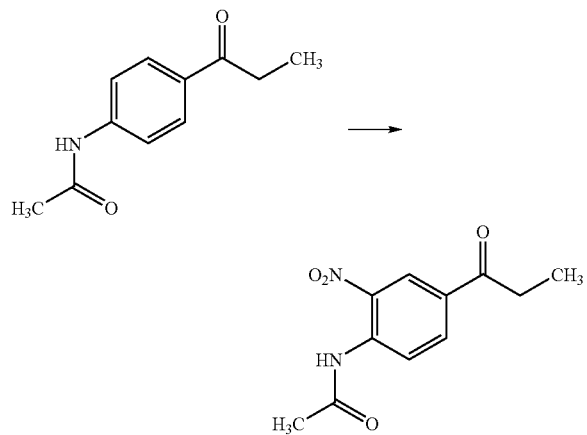

To 140 ml of nitric acid are added portionwise, while maintaining the temperature at −20° C., 37.8 g (198 mM) of N-(4-propanoylphenyl)acetamide. The reaction medium is then poured into a water/ice mixture. The solid that precipitates out is filtered off and washed with water to give, after drying, 37.6 g of N-(2-nitro-4-propanoylphenyl)acetamide in the form of a pale yellow solid.

Yield: 80.4%

$^1$H NMR (300 MHz/DMSO-d6) δ: 1.1 (t, 3H), 2.14 (s, 3H), 3.11 (q, 2H), 7.85 (d, 1H), 8.23 (d, 1H), 8.41 (s, 1H), 10.56 (s, 1H)

EXAMPLE 22

N-[4-(2-bromopropanoyl)-2-nitrophenyl]acetamide

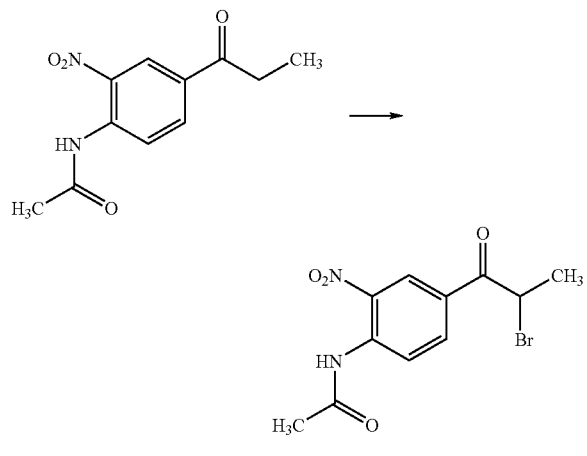

To 1600 ml of acetic acid are added 46.7 g (198 mM) of N-(2-nitro-4-propanoylphenyl)acetamide. To the solution obtained, heated to 35° C., is added over 2 hours a solution of 10.13 ml (198 mM) of bromine in 200 ml of acetic acid. The reaction medium is then added gently to 5000 ml of water, and a solid crystallises out. After filtering off the solid and washing with water, 56.8 g of N-[4-(2-bromopropanoyl)-2-nitrophenyl]acetamide are obtained in the form of a pale yellow solid.

Yield: 91%

$C_{11}H_{11}BrN_2O_4$=315.12

Mass spectrometry M−1=313.0

EXAMPLE 23

1-(4-amino-3-nitrophenyl)-2-bromopropan-1-one

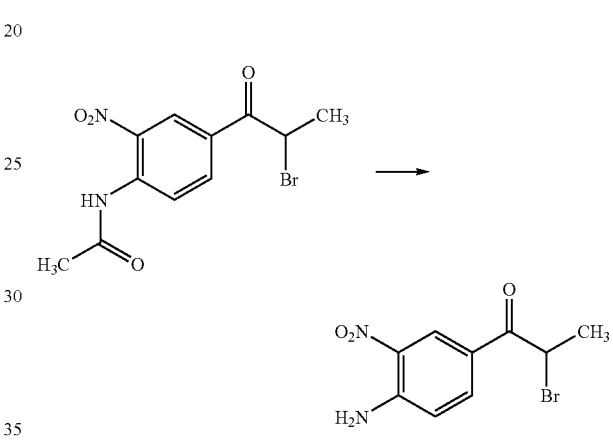

11.65 g (37 mM) of N-[4-(2-bromopropanoyl)-2-nitrophenyl]acetamide dissolved in aqueous 47% hydrobromic acid solution are maintained at 120° C. for 15 minutes with stirring. The reaction medium is then poured into water and extracted with ethyl acetate. The organic phase is washed with water, with aqueous sodium hydrogen carbonate solution and finally with saturated aqueous sodium chloride solution. The organic phase is separated out by settling, dried over anhydrous sodium sulfate and then evaporated under vacuum to give 35.7 g of 1-(4-amino-3-nitrophenyl)-2-bromopropan-1-one in the form of a yellow solid.

Yield: 96.5%

$^1$H NMR (300 MHz/DMSO-d6) δ: 1.91 (d, 3H), 5.92 (q, 1H), 7.26 (d, 1H), 8.15 (d, 1H) 8.35 (s, 2H), 8.85 (s, 1H)

EXAMPLE 24

5-(4-amino-3-nitrophenyl)-6-methyl-3,6-dihydro-2H-1,3,4-thiadiazin-2-one

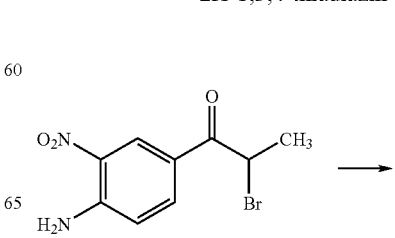

-continued

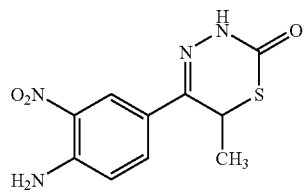

36.5 g (134 mM) of 1-(4-amino-3-nitrophenyl)-2-bromopropan-1-one and 24.3 g (202.5 mM) of O-ethyl hydrazinecarbothioate dissolved in 190 ml of acetonitrile are refluxed for 4 hours with stirring. The reaction mixture is cooled and maintained at 0° C. for 16 hours. The crystalline solid is filtered off and washed with cold acetonitrile to give, after drying, 10.4 g of 5-(4-amino-3-nitrophenyl)-6-methyl-3,6-dihydro-2H-1,3,4-thiadiazin-2-one in the form of a solid.

Yield: 29%

$^1$H NMR (300 MHz/DMSO-d6) δ: 1.51 (d, 3H), 4.80 (q, 1H), 7.14 (d, 1H), 7.88 (m, 3H) 8.41 (s, 1H)

EXAMPLE 25

5-(3,4-diaminophenyl)-6-methyl-3,6-dihydro-2H-1,3,4-thiadiazin-2-one

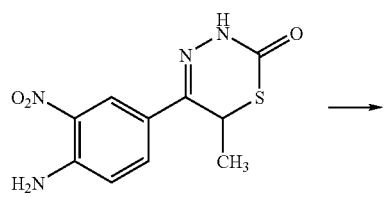

13.7 g (51.4 mM) of 5-(4-amino-3-nitrophenyl)-6-methyl-3,6-dihydro-2H-1,3,4-thiadiazin-2-one are placed under a hydrogen atmosphere at 3 bar for 4 hours in the presence of 24 g of Raney nickel in 280 ml of methanol. The reaction medium is then filtered and the filtrate is concentrated under vacuum to give 10.5 g of 5-(3,4-diaminophenyl)-6-methyl-3,6-dihydro-2H-1,3,4-thiadiazin-2-one in the form of a solid, which is treated with diisopropyl ether, filtered off and stored under argon at low temperature.

Yield: 86%

$C_{10}H_{12}N_4OS$=236.295

Mass spectrometry M+1=237.2

EXAMPLE 26

5-[2-(3-methoxyphenyl)-1H-benzimidazol-5-yl]-6-methyl-3,6-dihydro-2H-1,3,4-thiadiazin-2-one

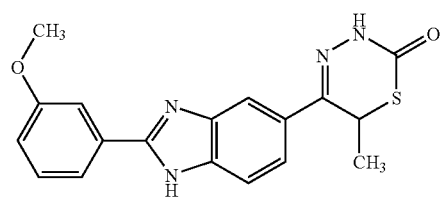

To 145 ml of 1-methyl-2-pyrrolidone are added 8 g (33.8 mM) of 5-(3,4-diaminophenyl)-6-methyl-3,6-dihydro-2H-1,3,4-thiadiazin-2-one, 4.11 ml (33.8 mM) of 3-methoxybenzaldehyde and 6.43 g (33.8 mM) of sodium bisulfite. The reaction medium is maintained at 110° C. for 2 hours 30 minutes. The reaction medium is poured into 1500 ml of water, and the solid that precipitates out is filtered off and washed with water to give 9.6 g of 5-[(2-[3-methoxyphenyl)-1H-benzimidazol-5-yl]-6-methyl-3,6-dihydro-2H-1,3,4-thiadiazin-2-one in the form of a solid.

Yield: 81%

$^1$H NMR (300 MHz/DMSO-d6) δ: 1.55 (d, 3H), 3.94 (s, 3H), 4.92 (q, 1H), 7.33 (d, 1H), 7.64 (t, 1H), 7.91 (d, 1H), 8.00 (t, 2H), 8.05 (s, 1H), 8.18 (s, 1H), 11.84 (s, 1H)

The following compounds are prepared via a similar or slightly modified method.

EXAMPLE 26-2

5-{2-[3-methoxy-4-(methylthio)phenyl]-1H-benzimidazol-5-yl}-6-methyl-3,6-dihydro-2H-1,3,4-thiadiazin-2-one hydrochloride

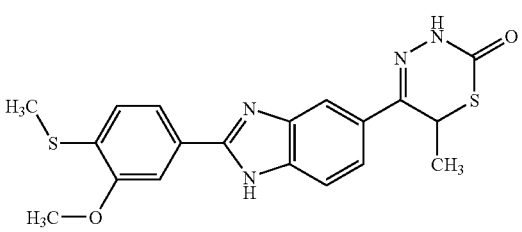

¹H NMR (300 MHz/DMSO-d6) δ: 1.45 (d, 3H), 2.39 (s, 3H), 3.89 (s, 3H), 4.79 (q, 1H), 7.34 (d, 1H), 7.73 (d, 1H), 7.81 (m, 3H), 7.99 (s, 1H), 11.68 (m, 1H)

EXAMPLE 26-3

5-{2-[3-methoxy-4-(methylsulfinyl)phenyl]-1H-benzimidazol-5-yl}-6-methyl-3,6-dihydro-2H-1,3,4-thiadiazin-2-one hydrochloride

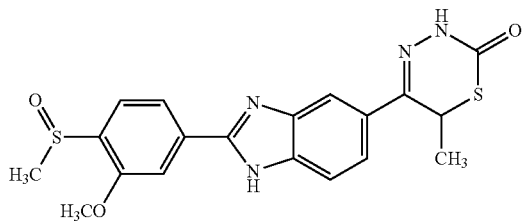

¹H NMR (300 MHz/DMSO-d6) δ: 1.56 (d, 3H), 2.83 (s, 3H), 4.07 (s, 3H), 4.93 (q, 1H), 7.90 (m, 3H), 8.17 (m, 2H), 8.23 (s, 1H), 11.81 (s, 1H)

EXAMPLE 26-4

5-{2-[4-(1H-imidazol-1-yl)phenyl]-1H-benzimidazol-5-yl}-6-methyl-3,6-dihydro-2H-1,3,4-thiadiazin-2-one dihydrochloride

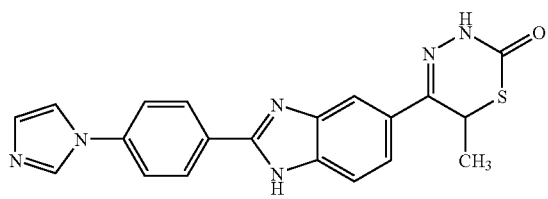

¹H NMR (300 MHz/DMSO-d6) δ: 1.58 (d, 3H), 4.92 (q, 1H), 7.80 (d, 1H), 7.86 (d, 1H), 7.99 (s, 1H), 8.13 (m, 3H), 8.44 (m, 1H), 8.55 (d, 2H), 9.83 (s, 1H), 11.74 (s, 1H)

The following compounds were prepared by application or adaptation of the methods described above:

5-[2-(4-methoxyphenyl)-1H-benzimidazol-5-yl]-3,6-dihydro-2H-1,3,4-thiadiazin-2-one,
6-methyl-5-[2-(1H-pyrazol-3-yl)-1H-benzimidazol-5-yl]-3,6-dihydro-2H-1,3,4-thiadiazin-2-one,
6-methyl-5-[2-(2-thienyl)-1H-benzimidazol-5-yl]-3,6-dihydro-2H-1,3,4-thiadiazin-2-one,
5-[2-(3-methoxyphenyl)-1H-benzimidazol-5-yl]-6-methyl-3,6-dihydro-2H-1,3,4-thiadiazin-2-one,
6-methyl-5-(2-pyrid-4-yl-1H-benzimidazol-5-yl)-3,6-dihydro-2H-1,3,4-thiadiazin-2-one,
5-{2-[3-methoxy-4-(methylthio)phenyl]-1H-benzimidazol-5-yl}-6-methyl-3,6-dihydro-2H-1,3,4-thiadiazin-2-one,
5-{2-[2-methoxy-4-(methylthio)phenyl]-1H-benzimidazol-5-yl}-6-methyl-3,6-dihydro-2H-1,3,4-thiadiazin-2-one,
6-methyl-5-[2-(1,3-thiazol-4-yl)-1H-benzimidazol-5-yl]-3,6-dihydro-2H-1,3,4-thiadiazin-2-one,
5-{2-[3-methoxy-4-(methylsulfinyl)phenyl]-1H-benzimidazol-5-yl}-6-methyl-3,6-dihydro-2H-1,3,4-thiadiazin-2-one,
5-[2-(1H-imidazol-1-yl)-1H-benzimidazol-5-yl]-6-methyl-3,6-dihydro-2H-1,3,4-thiadiazin-2-one,
5-{2-[4-(dimethylamino)phenyl]-1H-benzimidazol-5-yl}-6-methyl-3,6-dihydro-2H-1,3,4-thiadiazin-2-one,
6-methyl-5-{2-[4-(methylthio)phenyl]-1H-benzimidazol-5-yl}-3,6-dihydro-2H-1,3,4-thiadiazin-2-one,
6-methyl-5-{2-[4-(methylsulfinyl)phenyl]-1H-benzimidazol-5-yl}-3,6-dihydro-2H-1,3,4-thiadiazin-2-one,
5-[2-(2-methoxyphenyl)-1H-benzimidazol-5-yl]-6-methyl-3,6-dihydro-2H-1,3,4-thiadiazin-2-one,
5-[2-(3-methoxyphenyl)-1H-benzimidazol-5-yl]-6-methyl-3,6-dihydro-2H-1,3,4-thiadiazin-2-one,
3-methoxy-4-[5-(6-methyl-2-oxo-3,6-dihydro-2H-1,3,4-thiadiazin-5-yl)-1H-benzimidazol-2-yl]phenyl thiocyanate,
5-{2-[2-chloro-4-(methylthio)phenyl]-1H-benzimidazol-5-yl}-6-methyl-3,6-dihydro-2H-1,3,4-thiadiazin-2-one,
6-methyl-5-{2-[4-(pyrid-4-ylamino)phenyl]-1H-benzimidazol-5-yl}-3,6-dihydro-2H-1,3,4-thiadiazin-2-one,
5-[2-(4-methoxyphenyl)-1H-benzimidazol-5-yl]-3,6-dimethyl-3,6-dihydro-2H-1,3,4-thiadiazin-2-one,
3,6-dimethyl-5-[2-(1H-pyrazol-3-yl)-1H-benzimidazol-5-yl]-3,6-dihydro-2H-1,3,4-thiadiazin-2-one,
3,6-dimethyl-5-[2-(1,3-thiazol-4-yl)-1H-benzimidazol-5-yl]-3,6-dihydro-2H-1,3,4-thiadiazin-2-one,
3,6-dimethyl-5-(2-pyrid-4-yl-1H-benzimidazol-5-yl)-3,6-dihydro-2H-1,3,4-thiadiazin-2-one,
3-ethyl-6-methyl-5-[2-(1H-pyrazol-3-yl)-1H-benzimidazol-5-yl]-3,6-dihydro-2H-1,3,4-thiadiazin-2-one,
3-ethyl-6-methyl-5-[2-(1,3-thiazol-4-yl)-1H-benzimidazol-5-yl]-3,6-dihydro-2H-1,3,4-thiadiazin-2-one,
3-ethyl-5-[2-(4-methoxyphenyl)-1H-benzimidazol-5-yl]-6-methyl-3,6-dihydro-2H-1,3,4-thiadiazin-2-one,
5-[1-cycloheptyl-2-(3-methoxyphenyl)-1H-benzimidazol-5-yl]-3,6-dihydro-2H-1,3,4-thiadiazin-2-one,
5-[1-isobutyl-2-(3-methoxyphenyl)-1H-benzimidazol-5-yl]-3,6-dihydro-2H-1,3,4-thiadiazin-2-one,
5-[1-isobutyl-2-(3-methoxyphenyl)-1H-benzimidazol-5-yl]-3-(4-methylbenzyl)-3,6-dihydro-2H-1,3,4-thiadiazin-2-one,
3-(4-tert-butylbenzyl)-5-[1-isobutyl-2-(3-methoxyphenyl)-1H-benzimidazol-5-yl]-3,6-dihydro-2H-1,3,4-thiadiazin-2-one,
3-(2-fluorobenzyl)-5-[1-isobutyl-2-(3-methoxyphenyl)-1H-benzimidazol-5-yl]-3,6-dihydro-2H-1,3,4-thiadiazin-2-one,
5-[1-cycloheptyl-2-(3-methoxyphenyl)-1H-benzimidazol-5-yl]-3-methyl-3,6-dihydro-2H-1,3,4-thiadiazin-2-one,
5-[1-cycloheptyl-2-(3-methoxyphenyl)-1H-benzimidazol-5-yl]-3-propyl-3,6-dihydro-2H-1,3,4-thiadiazin-2-one,
5-[1-cycloheptyl-2-(3-methoxyphenyl)-1H-benzimidazol-5-yl]-3-isobutyl]-3,6-dihydro-2H-1,3,4-thiadiazin-2-one,
5-[1-cycloheptyl-2-(3-methoxyphenyl)-1H-benzimidazol-5-yl]-3-(2-methoxyethyl)]-3,6-dihydro-2H-1,3,4-thiadiazin-2-one,
5-[1-isobutyl-2-(3-methoxyphenyl)-1H-benzimidazol-5-yl]-3-(3-methylbenzyl)]-3,6-dihydro-2H-1,3,4-thiadiazin-2-one,
3-(3-fluorobenzyl)-5-[1-isobutyl-2-(3-methoxyphenyl)-1H-benzimidazol-5-yl]-3,6-dihydro-2H-1,3,4-thiadiazin-2-one,
3-benzyl-5-[1-isobutyl-2-(3-methoxyphenyl)-1H-benzimidazol-5-yl]-3,6-dihydro-2H-1,3,4-thiadiazin-2-one,
3-(4-fluorobenzyl)-5-[1-isobutyl-2-(3-methoxyphenyl)-1H-benzimidazol-5-yl]-3,6-dihydro-2H-1,3,4-thiadiazin-2-one, 3-(3-chlorobenzyl)-5-[1-isobutyl-2-(3-methoxyphenyl)-1H-benzimidazol-5-yl]-3,6-dihydro-2H-1,3,4-thiadiazin-2-one, 5-[1-isobutyl-2-(3-methoxyphenyl)-1H-benzimidazol-5-yl]-3-(3-methoxybenzyl)]-3,6-dihydro-2H-1,3,4-thiadiazin-2-one, 5-[1-isobutyl-2-(3-methoxyphenyl)-1H-benzimidazol-5-yl]-3-(4-trifluoromethoxybenzyl)]-3,6-dihydro-2H-1,3,4-thiadiazin-2-one, 5-[1-isobutyl-2-(3-methoxyphenyl)-1H-benzimidazol-5-yl]-3-(3-trifluoromethylbenzyl)]-3,6-dihydro-2H-1,3,4-thiadiazin-2-one, 5-[1-isobutyl-2-(3-methoxyphenyl)-1H-benzimidazol-5-yl]-3-(4-trifluoromethylbenzyl)]-3,6-dihydro-2H-1,3,4-thiadiazin-2-one, 3-(2,3-difluorobenzyl)-5-[1-isobutyl-2-(3-methoxyphenyl)-1H-benzimidazol-5-yl]-3,6-dihydro-2H-1,3,4-thiadiazin-2-one, 3-(2,4-difluorobenzyl)-5-[1-isobutyl-2-(3-methoxyphenyl)-1H-benzimidazol-5-yl]-3,6-dihydro-2H-1,3,4-thiadiazin-2-one, 3-(2,5-difluorobenzyl)-5-[1-isobutyl-2-(3-methoxyphenyl)-1H-benzimidazol-5-yl]-3,6-dihydro-2H-1,3,4-thiadiazin-2-one, 3-(2,6-difluorobenzyl)-5-[1-isobutyl-2-(3-methoxyphenyl)-1H-benzimidazol-5-yl]-3,6-dihydro-2H-1,3,4-thiadiazin-2-one, 3-(3,4-difluorobenzyl)-5-[1-isobutyl-2-(3-methoxyphenyl)-1H-benzimidazol-5-yl]-3,6-dihydro-2H-1,3,4-thiadiazin-2-one, 3-(3,5-dimethoxybenzyl)-5-[1-isobutyl-2-(3-methoxyphenyl)-1H-benzimidazol-5-yl]-3,6-dihydro-2H-1,3,4-thiadiazin-2-one, 3-cyclopropylmethyl-5-[1-isobutyl-2-(3-methoxyphenyl)-1H-benzimidazol-5-yl]-3,6-dihydro-2H-1,3,4-thiadiazin-2-one, 3-(2-hydroxyethyl)-5-[1-isobutyl-2-(3-methoxyphenyl)-1H-benzimidazol-5-yl]-3,6-dihydro-2H-1,3,4-thiadiazin-2-one, 3-ethyl-5-[1-isobutyl-2-(3-methoxyphenyl)-1H-benzimidazol-5-yl]-3,6-dihydro-2H-1,3,4-thiadiazin-2-one, 5-[1-isobutyl-2-(3-methoxyphenyl)-1H-benzimidazol-5-yl]-3-propyl]-3,6-dihydro-2H-1,3,4-thiadiazin-2-one, 5-[1-isobutyl-2-(3-methoxyphenyl)-1H-benzimidazol-5-yl]-3-isopropyl]-3,6-dihydro-2H-1,3,4-thiadiazin-2-one, 2-{5-[1-isobutyl-2-(3-methoxyphenyl)-1H-benzimidazol-5-yl]-2-oxo-6H-1,3,4-thiadiazin-3-yl}acetamide, 5-[1-isobutyl-2-(3-methoxyphenyl)-1H-benzimidazol-5-yl]-3-(2-methoxyethyl)]-3,6-dihydro-2H-1,3,4-thiadiazin-2-one, {5-[1-isobutyl-2-(3-methoxyphenyl)-1H-benzimidazol-5-yl]-2-oxo-6H-1,3,4-thiadiazin-3-yl}acetic acid, 5-[1-isobutyl-2-(3-methoxyphenyl)-1H-benzimidazol-5-yl]-6-methyl]-3,6-dihydro-2H-1,3,4-thiadiazin-2-one, 3-(2-hydroxyethyl)-5-[1-isobutyl-2-(3-methoxyphenyl)-1H-benzimidazol-5-yl]-6-methyl]-3,6-dihydro-2H-1,3,4-thiadiazin-2-one, 5-[1-isobutyl-2-(3-methoxyphenyl)-1H-benzimidazol-5-yl]-3-propyl]-3,6-dihydro-2H-1,3,4-thiadiazin-2-one, 5-[1-isobutyl-2-(3-methoxyphenyl)-1H-benzimidazol-5-yl]-3,6-dimethyl]-3,6-dihydro-2H-1,3,4-thiadiazin-2-one, 3-ethyl-5-[1-isobutyl-2-(3-methoxyphenyl)-1H-benzimidazol-5-yl]-6-methyl]-3,6-dihydro-2H-1,3,4-thiadiazin-2-one, 5-[1-isobutyl-2-(3-methoxyphenyl)-1H-benzimidazol-5-yl]-3-isopropyl-6-methyl]-3,6-dihydro-2H-1,3,4-thiadiazin-2-one, 3-cyclopropylmethyl-5-[1-isobutyl-2-(3-methoxyphenyl)-1H-benzimidazol-5-yl]-6-methyl]-3,6-dihydro-2H-1,3,4-thiadiazin-2-one, 3-ethyl-5-[2-(3-methoxyphenyl)-1-methyl-1H-benzimidazol-5-yl]-3,6-dihydro-2H-1,3,4-thiadiazin-2-one, 5-[2-(3-methoxyphenyl)-1-methyl-1H-benzimidazol-5-yl]-3-propyl]-3,6-dihydro-2H-1,3,4-thiadiazin-2-one hydrochloride, 3-cyclohexylmethyl-5-[2-(3-methoxyphenyl)-1-methyl-1H-benzimidazol-5-yl]-3,6-dihydro-2H-1,3,4-thiadiazin-2-one, 3-[2-(4-fluorophenoxy)ethyl]-5-[2-(3-methoxyphenyl)-1-methyl-1H-benzimidazol-5-yl]-3,6-dihydro-2H-1,3,4-thiadiazin-2-one, 5-[2-(3-methoxyphenyl)-1-methyl-1H-benzimidazol-5-yl]-3-methyl]-3,6-dihydro-2H-1,3,4-thiadiazin-2-one, 3-isopropyl-5-[2-(3-methoxyphenyl)-1-methyl-1H-benzimidazol-5-yl]-3,6-dihydro-2H-1,3,4-thiadiazin-2-one, 3-isobutyl-5-[2-(3-methoxyphenyl)-1-methyl-1H-benzimidazol-5-yl]-3,6-dihydro-2H-1,3,4-thiadiazin-2-one, 3-cyclopropylmethyl-5-[2-(3-methoxyphenyl)-1-methyl-1H-benzimidazol-5-yl]-3,6-dihydro-2H-1,3,4-thiadiazin-2-one, 5-[2-(3-methoxyphenyl)-1-methyl-1H-benzimidazol-5-yl]-6-methyl]-3,6-dihydro-2H-1,3,4-thiadiazin-2-one, 3-ethyl-5-[2-(3-methoxyphenyl)-1-methyl-1H-benzimidazol-5-yl]-6-methyl]-3,6-dihydro-2H-1,3,4-thiadiazin-2-one, 5-[2-(3-methoxyphenyl)-1-methyl-1H-benzimidazol-5-yl]-6-methyl-3-propyl]-3,6-dihydro-2H-1,3,4-thiadiazin-2-one, 5-[2-(3-methoxyphenyl)-1-methyl-1H-benzimidazol-5-yl]-6-methyl-3-(2-piperidin-1-ylethyl)]-3,6-dihydro-2H-1,3,4-thiadiazin-2-one, 3-isobutyl-5-[2-(3-methoxyphenyl)-1-methyl-1H-benzimidazol-5-yl]-6-methyl]-3,6-dihydro-2H-1,3,4-thiadiazin-2-one, 5-[2-(3-methoxyphenyl)-1-methyl-1H-benzimidazol-5-yl]-3,6-dimethyl]-3,6-dihydro-2H-1,3,4-thiadiazin-2-one, 6-methyl-5-[1-methyl-2-(3-trifluoromethylphenyl)-1H-benzimidazol-5-yl]-3,6-dihydro-2H-1,3,4-thiadiazin-2-one, 3-benzyl-6-methyl-5-[1-methyl-2-(3-trifluoromethylphenyl)-1H-benzimidazol-5-yl]-3,6-dihydro-2H-1,3,4-thiadiazin-2-one, 3-cyclopropylmethyl-6-methyl-5-[1-methyl-2-(3-trifluoromethylphenyl)-1H-benzimidazol-5-yl]-3,6-dihydro-2H-1,3,4-thiadiazin-2-one, 3-isopropyl-6-methyl-5-[1-methyl-2-(3-trifluoromethylphenyl)-1H-benzimidazol-5-yl]-3,6-dihydro-2H-1,3,4-thiadiazin-2-one, 3,6-dimethyl-5-[1-methyl-2-(3-trifluoromethylphenyl)-1H-benzimidazol-5-yl]-3,6-dihydro-2H-1,3,4-thiadiazin-2-one, 3-ethyl-6-methyl-5-[1-methyl-2-(3-trifluoromethylphenyl)-1H-benzimidazol-5-yl]-3,6-dihydro-2H-1,3,4-thiadiazin-2-one, 5-[1-benzyl-2-(1-methyl-1H-pyrrol-2-yl)-1H-benzimidazol-5-yl]-6-methyl]-3,6-dihydro-2H-1,3,4-thiadiazin-2-one, 5-[1-benzyl-2-(1-methyl-1H-imidazol-2-yl)-1H-benzimidazol-5-yl]-6-methyl]-3,6-dihydro-2H-1,3,4-thiadiazin-2-one, 5-(1-benzyl-2-thiophen-2-yl-1H-benzimidazol-5-yl)-6-methyl]-3,6-dihydro-2H-1,3,4-thiadiazin-2-one, 5-[1-benzyl-2(3-methoxyphenyl)-1H-benzimidazol-5-yl]-6-methyl]-3,6-dihydro-2H-1,3,4-thiadiazin-2-one, 5-[1-benzyl-2-(4-methoxyphenyl)-1H-benzimidazol-5-yl]-6-methyl]-3,6-dihydro-2H-1,3,4-thiadiazin-2-one, 5-[1-benzyl-2-(3-hydroxy-4-methoxyphenyl)-1H-benzimidazol-5-yl]-6-methyl]-3,6-dihydro-2H-1,3,4-thiadiazin-2-one,
5-[1-benzyl-2-(2,4-dihydroxyphenyl)-1H-benzimidazol-5-yl]-6-methyl]-3,6-dihydro-2H-1,3,4-thiadiazin-2-one,
5-[1-benzyl-2-(3,4-dihydroxyphenyl)-1H-benzimidazol-5-yl]-6-methyl]-3,6-dihydro-2H-1,3,4-thiadiazin-2-one,
5-[1-benzyl-2-(3,4,5-trihydroxyphenyl)-1H-benzimidazol-5-yl]-6-methyl]-3,6-dihydro-2H-1,3,4-thiadiazin-2-one,
6-methyl-5-[1-methyl-2-(1-methyl-1H-pyrrol-2-yl)-1H-benzimidazol-5-yl]-3,6-dihydro-2H-1,3,4-thiadiazin-2-one,
5-[2-(1H-imidazol-4-yl)-1-methyl-1H-benzimidazol-5-yl]-6-methyl]-3,6-dihydro-2H-1,3,4-thiadiazin-2-one,
5-[2-(1H-Imidazol-2-yl)-1-methyl-1H-benzimidazol-5-yl]-6-methyl]-3,6-dihydro-2H-1,3,4-thiadiazin-2-one,
6-methyl-5-[1-methyl-2-(5-methyl-3H-imidazol-4-yl)-1H-benzimidazol-5-yl]-3,6-dihydro-2H-1,3,4-thiadiazin-2-one,
6-methyl-5-[1-methyl-2-(1-methyl-1H-imidazol-2-yl)-1H-benzimidazol-5-yl]-3,6-dihydro-2H-1,3,4-thiadiazin-2-one,
6-methyl-5-(1-methyl-2-thiophen-2-yl-1H-benzimidazol-5-yl)]-3,6-dihydro-2H-1,3,4-thiadiazin-2-one,
6-methyl-5-(1-methyl-2-thiophen-3-yl-1H-benzimidazol-5-yl)]-3,6-dihydro-2H-1,3,4-thiadiazin-2-one,
5-[2-(2-methoxyphenyl)-1-methyl-1H-benzimidazol-5-yl]-6-methyl]-3,6-dihydro-2H-1,3,4-thiadiazin-2-one,
5-[2-(4-methoxyphenyl)-1-methyl-1H-benzimidazol-5-yl]-6-methyl]-3,6-dihydro-2H-1,3,4-thiadiazin-2-one,
5-[2-(3-hydroxy-4-methoxyphenyl)-1-methyl-1H-benzimidazol-5-yl]-6-methyl]-3,6-dihydro-2H-1,3,4-thiadiazin-2-one,
5-[2-(3,4-dihydroxyphenyl)-1-methyl-1H-benzimidazol-5-yl]-6-methyl]-3,6-dihydro-2H-1,3,4-thiadiazin-2-one,
6-methyl-5-[1-methyl-2-(3,4,5-trihydroxyphenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-(3-methylbenzyl)]-3,6-dihydro-2H-1,3,4-thiadiazin-2-one,
5-[1-ethyl-2-(3-fluorophenyl)-1H-benzimidazol-5-yl]-3-(4-methylbenzyl)]-3,6-dihydro-2H-1,3,4-thiadiazin-2-one,
3-(4-tert-butylbenzyl)-5-[1-ethyl-2-(3-fluorophenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-(2-fluorobenzyl)]-3,6-dihydro-2H-1,3,4-thiadiazin-2-one,
5-[1-ethyl-2-(3-fluorophenyl)-1H-benzimidazol-5-yl]-3-(3-fluorobenzyl)]-3,6-dihydro-2H-1,3,4-thiadiazin-2-one,
3-benzyl-5-[1-ethyl-2-(3-fluorophenyl)-1H-benzimidazol-5-yl]-3,6-dihydro-2H-1,3,4-thiadiazin-2-one,
3-(3-chlorobenzyl)-5-[1-ethyl-2-(3-fluorophenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-methyl]-3,6-dihydro-2H-1,3,4-thiadiazin-2-one,
3-cyclohexylmethyl-5-[1-ethyl-2-(3-fluorophenyl)-1H-benzimidazol-5-yl]-3,6-dihydro-2H-1,3,4-thiadiazin-2-one,
3-(2-dimethylaminoethyl)-5-[1-ethyl-2-(3-fluorophenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-(2-pyrrolidin-1-ylethyl)]-3,6-dihydro-2H-1,3,4-thiadiazin-2-one,
5-[1-isobutyl-2-(3-methoxyphenyl)-1H-benzimidazol-5-yl]-3-(3-methylbenzyl)]-3,6-dihydro-2H-1,3,4-thiadiazin-2-one,
5-[2-(4-methoxyphenyl)-1H-benzimidazol-5-yl]-6-methyl]-3,6-dihydro-2H-1,3,4-thiadiazin-2-one, 3-(2-dimethylaminoethyl)-6-methyl-5-[1-methyl-2-(3-trifluoromethylphenyl)-1H-benzimidazol-5-yl]-3,6-dihydro-2H-1,3,4-thiadiazin-2-one,
6-methyl-5-[1-methyl-2-(3-trifluoromethylphenyl)-1H-benzimidazol-5-yl]-3-(2-piperidin-1-ylethyl)]-3,6-dihydro-2H-1,3,4-thiadiazin-2-one,
3-cyclohexylmethyl-6-methyl-5-[1-methyl-2-(3-trifluoromethylphenyl)-1H-benzimidazol-5-yl]-3,6-dihydro-2H-1,3,4-thiadiazin-2-one,
6-methyl-5-[1-methyl-2-(3-trifluoromethylphenyl)-1H-benzimidazol-5-yl]-3-(2-morpholin-4-ylethyl)]-3,6-dihydro-2H-1,3,4-thiadiazin-2-one,
6-methyl-5-[1-methyl-2-(3-trifluoromethylphenyl)-1H-benzimidazol-5-yl]-3-(2-pyrrolidin-1-ylethyl)]-3,6-dihydro-2H-1,3,4-thiadiazin-2-one,
2-{6-methyl-5-[1-methyl-2-(3-trifluoromethylphenyl)-1H-benzimidazol-5-yl]-2-oxo-6H-1,3,4-thiadiazin-3-yl}acetamide,
3-(2-methoxyethyl)-6-methyl-5-[1-methyl-2-(3-trifluoromethylphenyl)-1H-benzimidazol-5-yl]-3,6-dihydro-2H-1,3,4-thiadiazin-2-one,
5-[2-(3-fluorophenyl)-1-methyl-1H-benzimidazol-5-yl]-3-(2-hydroxyethyl)-6-methyl]-3,6-dihydro-2H-1,3,4-thiadiazin-2-one,
3-cyclohexylmethyl-5-[2-(3-fluorophenyl)-1-methyl-1H-benzimidazol-5-yl]-6-methyl]-3,6-dihydro-2H-1,3,4-thiadiazin-2-one,
2-{5-[2-(3-fluorophenyl)-1-methyl-1H-benzimidazol-5-yl]-6-methyl-2-oxo-6H-1,3,4-thiadiazin-3-yl}acetamide,
3-[2-(4-fluorophenoxy)ethyl]-5-[2-(3-fluorophenyl)-1-methyl-1H-benzimidazol-5-yl]-6-methyl]-3,6-dihydro-2H-1,3,4-thiadiazin-2-one,
5-[2-(3-fluorophenyl)-1-methyl-1H-benzimidazol-5-yl]-3-isopropyl-6-methyl]-3,6-dihydro-2H-1,3,4-thiadiazin-2-one,
5-[2-(3-fluorophenyl)-1-methyl-1H-benzimidazol-5-yl]-3-isobutyl-6-methyl]-3,6-dihydro-2H-1,3,4-thiadiazin-2-one,
ethyl 4-{5-[2-(3-fluorophenyl)-1-methyl-1H-benzimidazol-5-yl]-6-methyl-2-oxo-6H-1,3,4-thiadiazin-3-yl}butyrate,
ethyl 3-{5-[2-(3-fluorophenyl)-1-methyl-1H-benzimidazol-5-yl]-6-methyl-2-oxo-6H-1,3,4-thiadiazin-3-yl}propionate,
3-cyclopropylmethyl-5-[2-(3-fluorophenyl)-1-methyl-1H-benzimidazol-5-yl]-6-methyl]-3,6-dihydro-2H-1,3,4-thiadiazin-2-one,
5-[2-(3-fluorophenyl)-1-methyl-1H-benzimidazol-5-yl]-3-(2-methoxyethyl)-6-methyl]-3,6-dihydro-2H-1,3,4-thiadiazin-2-one,
3-benzyl-5-[2-(3-fluorophenyl)-1-methyl-1H-benzimidazol-5-yl]-6-methyl]-3,6-dihydro-2H-1,3,4-thiadiazin-2-one,
ethyl{5-[2-(3-fluorophenyl)-1-methyl-1H-benzimidazol-5-yl]-6-methyl-2-oxo-6H-1,3,4-thiadiazin-3-yl}acetate,
5-[2-(3-fluorophenyl)-1-methyl-1H-benzimidazol-5-yl]-6-methyl-3-propyl]-3,6-dihydro-2H-1,3,4-thiadiazin-2-one,
5-[2-(3-fluorophenyl)-1-methyl-1H-benzimidazol-5-yl]-6-methyl-3-(2-morpholin-4-ylethyl)]-3,6-dihydro-2H-1,3,4-thiadiazin-2-one
5-[2-(3-fluorophenyl)-1-methyl-1H-benzimidazol-5-yl]-6-methyl-3-(2-piperidin-1-ylethyl)]-3,6-dihydro-2H-1,3,4-thiadiazin-2-one,
5-[2-(3-fluorophenyl)-1-methyl-1H-benzimidazol-5-yl]-6-methyl]-3,6-dihydro-2H-1,3,4-thiadiazin-2-one,
3-cyclohexylmethyl-5-[2-(3-fluorophenyl)-1-methyl-1H-benzimidazol-5-yl]-3,6-dihydro-2H-1,3,4-thiadiazin-2-one, 2-{5-[2-(3-fluorophenyl)-1-methyl-1H-benzimidazol-5-yl]-2-oxo-6H-1,3,4-thiadiazin-3-yl}acetamide,
3-[2-(4-fluorophenoxy)ethyl]-5-[2-(3-fluorophenyl)-1-methyl-1H-benzimidazol-5-yl]-3,6-dihydro-2H-1,3,4-thiadiazin-2-one,
5-[2-(3-fluorophenyl)-1-methyl-1H-benzimidazol-5-yl]-3-isopropyl]-3,6-dihydro-2H-1,3,4-thiadiazin-2-one,
5-[2-(3-fluorophenyl)-1-methyl-1H-benzimidazol-5-yl]-3-isobutyl]-3,6-dihydro-2H-1,3,4-thiadiazin-2-one,
3-cyclopropylmethyl-5-[2-(3-fluorophenyl)-1-methyl-1H-benzimidazol-5-yl]-3,6-dihydro-2H-1,3,4-thiadiazin-2-one
5-[2-(3-fluorophenyl)-1-methyl-1H-benzimidazol-5-yl]-3-(2-methoxyethyl)]-3,6-dihydro-2H-1,3,4-thiadiazin-2-one,
3-benzyl-5-[2-(3-fluorophenyl)-1-methyl-1H-benzimidazol-5-yl]-3,6-dihydro-2H-1,3,4-thiadiazin-2-one,
ethyl{5-[2-(3-fluorophenyl)-1-methyl-1H-benzimidazol-5-yl]-2-oxo-6H-1,3,4-thiadiazin-3-yl}acetate,
5-[2-(3-fluorophenyl)-1-methyl-1H-benzimidazol-5-yl]-3-(2-piperidin-1-ylethyl)]-3,6-dihydro-2H-1,3,4-thiadiazin-2-one,
5-[2-(3-fluorophenyl)-1-methyl-1H-benzimidazol-5-yl]-3,6-dihydro-2H-1,3,4-thiadiazin-2-one,
5-[2-(3-fluorophenyl)-1-methyl-1H-benzimidazol-5-yl]-3-propyl]-3,6-dihydro-2H-1,3,4-thiadiazin-2-one,
5-(1-benzyl-2-thiophen-3-yl-1H-benzimidazol-5-yl)-6-methyl]-3,6-dihydro-2H-1,3,4-thiadiazin-2-one,
5-[1-benzyl-2-(2-methoxyphenyl)-1H-benzimidazol-5-yl]-6-methyl]-3,6-dihydro-2H-1,3,4-thiadiazin-2-one,
5-[1-cyclopropylmethyl-2-(3-methoxyphenyl)-1H-benzimidazol-5-yl]-6-methyl]-3,6-dihydro-2H-1,3,4-thiadiazin-2-one,
3-cyclohexylmethyl-5-(2-furan-2-yl-1-methyl-1H-benzimidazol-5-yl)]-3,6-dihydro-2H-1,3,4-thiadiazin-2-one,
3-benzyl-5-(2-furan-2-yl-1-methyl-1H-benzimidazol-5-yl)]-3,6-dihydro-2H-1,3,4-thiadiazin-2-one,
3-cyclopropylmethyl-5-(2-furan-2-yl-1-methyl-1H-benzimidazol-5-yl)]-3,6-dihydro-2H-1,3,4-thiadiazin-2-one,
5-(2-furan-2-yl-1-methyl-1H-benzimidazol-5-yl)-3-methyl]-3,6-dihydro-2H-1,3,4-thiadiazin-2-one,
3-ethyl-5-(2-furan-2-yl-1-methyl-1H-benzimidazol-5-yl)]-3,6-dihydro-2H-1,3,4-thiadiazin-2-one,
5-(2-furan-2-yl-1-methyl-1H-benzimidazol-5-yl)-3-(2-piperidin-1-ylethyl)]-3,6-dihydro-2H-1,3,4-thiadiazin-2-one,
5-(2-furan-2-yl-1-methyl-1H-benzimidazol-5-yl)-3-(2-pyrrolidin-1-ylethyl)]-3,6-dihydro-2H-1,3,4-thiadiazin-2-one,
5-(2-furan-2-yl-1-methyl-1H-benzimidazol-5-yl)-3-isobutyl]-3,6-dihydro-2H-1,3,4-thiadiazin-2-one,
5-(2-furan-2-yl-1-methyl-1H-benzimidazol-5-yl)]-3,6-dihydro-2H-1,3,4-thiadiazin-2-one,
2-{5-[2-(3-methoxyphenyl)-1-methyl-1H-benzimidazol-5-yl]-6-methyl-2-oxo-6H-1,3,4-thiadiazin-3-yl}acetamide,
3-isopropyl-5-[2-(3-methoxyphenyl)-1-methyl-1H-benzimidazol-5-yl]-6-methyl]-3,6-dihydro-2H-1,3,4-thiadiazin-2-one,
3-(4-tert-butylbenzyl)-5-[1-methyl-2-(3-trifluoromethylphenyl)-1H-benzimidazol-5-yl]-3,6-dihydro-2H-1,3,4-thiadiazin-2-one,
3-(4-fluorobenzyl)-5-[1-methyl-2-(3-trifluoromethylphenyl)-1H-benzimidazol-5-yl]-3,6-dihydro-2H-1,3,4-thiadiazin-2-one,
5-[1-methyl-2-(3-trifluoromethylphenyl)-1H-benzimidazol-5-yl]-3-(4-trifluoromethoxybenzyl)]-3,6-dihydro-2H-1,3,4-thiadiazin-2-one,
5-[1-methyl-2-(3-trifluoromethylphenyl)-1H-benzimidazol-5-yl]-3-(4-trifluoromethylbenzyl)]-3,6-dihydro-2H-1,3,4-thiadiazin-2-one,
3-{5-[1-methyl-2-(3-trifluoromethylphenyl)-1H-benzimidazol-5-yl]-2-oxo-6H-1,3,4-thiadiazin-3-ylmethyl}benzonitrile,
3-(4-methanesulfonylbenzyl)-5-[1-methyl-2-(3-trifluoromethylphenyl)-1H-benzimidazol-5-yl]-3,6-dihydro-2H-1,3,4-thiadiazin-2-one,
3-(3,5-dimethoxybenzyl)-5-[1-methyl-2-(3-trifluoromethylphenyl)-1H-benzimidazol-5-yl]-3,6-dihydro-2H-1,3,4-thiadiazin-2-one,
5-[1-methyl-2-(3-trifluoromethylphenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-(4-fluorobenzyl)]-3,6-dihydro-2H-1,3,4-thiadiazin-2-one,
5-[1-ethyl-2-(3-fluorophenyl)-1H-benzimidazol-5-yl]-3-(3-methoxybenzyl)]-3,6-dihydro-2H-1,3,4-thiadiazin-2-one,
5-[1-ethyl-2-(3-fluorophenyl)-1H-benzimidazol-5-yl]-3-(4-trifluoromethoxybenzyl)]-3,6-dihydro-2H-1,3,4-thiadiazin-2-one,
2-{5-[1-ethyl-2-(3-fluorophenyl)-1H-benzimidazol-5-yl]-2-oxo-6H-1,3,4-thiadiazin-3-yl}acetamide,
3-cyclopropylmethyl-5-[1-ethyl-2-(3-fluorophenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-isopropyl]-3,6-dihydro-2H-1,3,4-thiadiazin-2-one
3-ethyl-5-[1-ethyl-2-(3-fluorophenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-propyl]-3,6-dihydro-2H-1,3,4-thiadiazin-2-one,
5-[1-ethyl-2-(3-fluorophenyl)-1H-benzimidazol-5-yl]-3-(2-methoxyethyl)]-3,6-dihydro-2H-1,3,4-thiadiazin-2-one,
{5-[1-ethyl-2-(3-fluorophenyl)-1H-benzimidazol-5-yl]-2-oxo-6H-1,3,4-thiadiazin-3-yl}acetic acid,
5-[1-ethyl-2-(3-fluorophenyl)-1H-benzimidazol-5-yl]-3-(2-hydroxyethyl)]-3,6-dihydro-2H-1,3,4-thiadiazin-2-one,
5-[1-ethyl-2-(3-fluorophenyl)-1H-benzimidazol-5-yl]-3-(3-hydroxypropyl)]-3,6-dihydro-2H-1,3,4-thiadiazin-2-one,
3-(2-aminoethyl)-5-[1-ethyl-2-(3-fluorophenyl)-1H-benzimidazol-5-yl]-3,6-dihydro-2H-1,3,4-thiadiazin-2-one,
3-(3-aminopropyl)-5-[1-ethyl-2-(3-fluorophenyl)-1H-benzimidazol-5-yl]-3,6-dihydro-2H-1,3,4-thiadiazin-2-one,
3-benzyl-5-[1-ethyl-2-(3-methoxyphenyl)-1H-benzimidazol-5-yl]-3,6-dihydro-2H-1,3,4-thiadiazin-2-one,
5-[1-ethyl-2-(3-methoxyphenyl)-1H-benzimidazol-5-yl]-3-(4-methylbenzyl)]-3,6-dihydro-2H-1,3,4-thiadiazin-2-one,
5-[1-ethyl-2-(3-methoxyphenyl)-1H-benzimidazol-5-yl]-3-(2-fluorobenzyl)]-3,6-dihydro-2H-1,3,4-thiadiazin-2-one,
3-benzyl-5-[1-methyl-2-(3-trifluoromethylphenyl)-1H-benzimidazol-5-yl]-3,6-dihydro-2H-1,3,4-thiadiazin-2-one,
3-methyl-5-[1-methyl-2-(3-trifluoromethylphenyl)-1H-benzimidazol-5-yl]-3,6-dihydro-2H-1,3,4-thiadiazin-2-one,
3-cyclohexylmethyl-5-[1-methyl-2-(3-trifluoromethylphenyl)-1H-benzimidazol-5-yl]-3,6-dihydro-2H-1,3,4-thiadiazin-2-one,
3-(3-aminopropyl)-5-[1-methyl-2-(3-trifluoromethylphenyl)-1H-benzimidazol-5-yl]-3,6-dihydro-2H-1,3,4-thiadiazin-2-one,
3-(2-aminoethyl)-5-[1-methyl-2-(3-trifluoromethylphenyl)-1H-benzimidazol-5-yl]-3,6-dihydro-2H-1,3,4-thiadiazin-2-one, 3-(2-aminoethyl)-5-[1-ethyl-2-(3-methoxyphenyl)-1H-benzimidazol-5-yl]-3,6-dihydro-2H-1,3,4-thiadiazin-2-one,
3-(3-aminopropyl)-5-[1-ethyl-2-(3-methoxyphenyl)-1H-benzimidazol-5-yl]-3,6-dihydro-2H-1,3,4-thiadiazin-2-one,
5-[1-ethyl-2-(3-methoxyphenyl)-1H-benzimidazol-5-yl]-3-(2-hydroxyethyl)]-3,6-dihydro-2H-1,3,4-thiadiazin-2-one
5-[1-ethyl-2-(3-methoxyphenyl)-1H-benzimidazol-5-yl]-3-(3-hydroxypropyl)]-3,6-dihydro-2H-1,3,4-thiadiazin-2-one,
N-(2-{5-[1-methyl-2-(3-trifluoromethylphenyl)-1H-benzimidazol-5-yl]-2-oxo-6H-1,3,4-thiadiazin-3-yl}ethyl)acetamide,
furan-2-carboxylic acid (2-{5-[1-methyl-2-(3-trifluoromethylphenyl)-1H-benzimidazol-5-yl]-2-oxo-6H-1,3,4-thiadiazin-3-yl}ethyl)amide,
N-(2-{5-[1-methyl-2-(3-trifluoromethylphenyl)-1H-benzimidazol-5-yl]-2-oxo-6H-1,3,4-thiadiazin-3-yl}ethyl)isobutyramide,
cyclopentanecarboxylic acid (2-{5-[1-methyl-2-(3-trifluoromethylphenyl)-1H-benzimidazol-5-yl]-2-oxo-6H-1,3,4-thiadiazin-3-yl}ethyl)amide,
N-(2-{5-[1-methyl-2-(3-trifluoromethylphenyl)-1H-benzimidazol-5-yl]-2-oxo-6H-1,3,4-thiadiazin-3-yl}ethyl)benzamide,
N-(2-{5-[1-methyl-2-(3-trifluoromethylphenyl)-1H-benzimidazol-5-yl]-2-oxo-6H-1,3,4-thiadiazin-3-yl}ethyl)methanesulfonamide,
N-(2-{5-[1-methyl-2-(3-trifluoromethylphenyl)-1H-benzimidazol-5-yl]-2-oxo-6H-1,3,4-thiadiazin-3-yl}ethyl)benzenesulfonamide,
5-[1-methyl-2-(3-trifluoromethylphenyl)-1H-benzimidazol-5-yl]-6-propyl]-3,6-dihydro-2H-1,3,4-thiadiazin-2-one,
3-ethyl-5-[1-methyl-2-(3-trifluoromethylphenyl)-1H-benzimidazol-5-yl]-6-propyl]-3,6-dihydro-2H-1,3,4-thiadiazin-2-one,
5-[1-methyl-2-(3-trifluoromethylphenyl)-1H-benzimidazol-5-yl]-3,6-dipropyl]-3,6-dihydro-2H-1,3,4-thiadiazin-2-one,
3-benzyl-5-[1-methyl-2-(3-trifluoromethylphenyl)-1H-benzimidazol-5-yl]-6-propyl]-3,6-dihydro-2H-1,3,4-thiadiazin-2-one,
3-cyclopropylmethyl-5-[1-methyl-2-(3-trifluoromethylphenyl)-1H-benzimidazol-5-yl]-6-propyl]-3,6-dihydro-2H-1,3,4-thiadiazin-2-one,
3-isopropyl-5-[1-methyl-2-(3-trifluoromethylphenyl)-1H-benzimidazol-5-yl]-6-propyl]-3,6-dihydro-2H-1,3,4-thiadiazin-2-one,
3-isobutyl-5-[1-methyl-2-(3-trifluoromethylphenyl)-1H-benzimidazol-5-yl]-6-propyl]-3,6-dihydro-2H-1,3,4-thiadiazin-2-one,
5-[1-methyl-2-(3-trifluoromethylphenyl)-1H-benzimidazol-5-yl]-3-(2-piperidin-1-ylethyl)-6-propyl]-3,6-dihydro-2H-1,3,4-thiadiazin-2-one,
5-[1-methyl-2-(3-trifluoromethylphenyl)-1H-benzimidazol-5-yl]-6-propyl-3-(2-pyrrolidin-1-ylethyl)]-3,6-dihydro-2H-1,3,4-thiadiazin-2-one,
1-(2-{5-[1-methyl-2-(3-trifluoromethylphenyl)-1H-benzimidazol-5-yl]-2-oxo-6H-1,3,4-thiadiazin-3-yl}ethyl)-3-phenylurea,
1-ethyl-3-(2-{5-[1-methyl-2-(3-trifluoromethylphenyl)-1H-benzimidazol-5-yl]-2-oxo-6H-1,3,4-thiadiazin-3-yl}ethyl)urea,
5-[1-ethyl-2-(3-methoxyphenyl)-1H-benzimidazol-5-yl]-3,6-dihydro-2H-1,3,4-thiadiazin-2-one,
3-cyclopropylmethyl-5-[1-methyl-2-(3-trifluoromethylphenyl)-1H-benzimidazol-5-yl]-3,6-dihydro-2H-1,3,4-thiadiazin-2-one,
butane-1-sulfonic acid (2-{5-[1-methyl-2-(3-trifluoromethylphenyl)-1H-benzimidazol-5-yl]-2-oxo-6H-1,3,4-thiadiazin-3-yl}ethyl)amide,
N-{2-[5-(2-furan-2-yl-1-methyl-1H-benzimidazol-5-yl)-2-oxo-6H-1,3,4-thiadiazin-3-yl]ethyl}acetamide,
N-{2-[5-(2-furan-2-yl-1-methyl-1H-benzimidazol-5-yl)-2-oxo-6H-1,3,4-thiadiazin-3-yl]ethyl}isobutyramide,
cyclopentanecarboxylic acid {2-[5-(2-furan-2-yl-1-methyl-1H-benzimidazol-5-yl)-2-oxo-6H-1,3,4-thiadiazin-3-yl]ethyl}amide,
N-{2-[5-(2-furan-2-yl-1-methyl-1H-benzimidazol-5-yl)-2-oxo-6H-1,3,4-thiadiazin-3-yl]ethyl}benzamide,
N-{2-[5-(2-furan-2-yl-1-methyl-1H-benzimidazol-5-yl)-2-oxo-6H-1,3,4-thiadiazin-3-yl]ethyl}nicotinamide,
cyclopropanecarboxylic acid {2-[5-(2-furan-2-yl-1-methyl-1H-benzimidazol-5-yl)-2-oxo-6H-1,3,4-thiadiazin-3-yl]ethyl}amide,
3-fluoro-N-{2-[5-(2-furan-2-yl-1-methyl-1H-benzimidazol-5-yl)-2-oxo-6H-1,3,4-thiadiazin-3-yl]ethyl}benzamide,
N-{2-[5-(2-furan-2-yl-1-methyl-1H-benzimidazol-5-yl)-2-oxo-6H-1,3,4-thiadiazin-3-yl]ethyl}-4-methylbenzamide,
3-(2-aminoethyl)-5-(2-furan-2-yl-1-methyl-1H-benzimidazol-5-yl)]-3,6-dihydro-2H-1,3,4-thiadiazin-2-one,
N-{2-[5-(2-furan-2-yl-1-methyl-1H-benzimidazol-5-yl)-2-oxo-6H-1,3,4-thiadiazin-3-yl]ethyl}benzenesulfonamide,
butane-1-sulfonic acid {2-[5-(2-furan-2-yl-1-methyl-1H-benzimidazol-5-yl)-2-oxo-6H-1,3,4-thiadiazin-3-yl]ethyl}amide,
1-{2-[5-(2-furan-2-yl-1-methyl-1H-benzimidazol-5-yl)-2-oxo-6H-1,3,4-thiadiazin-3-yl]ethyl}-3-isopropylurea,
1-{2-[5-(2-furan-2-yl-1-methyl-1H-benzimidazol-5-yl)-2-oxo-6H-1,3,4-thiadiazin-3-yl]ethyl}-3-phenylurea,
1-cyclopentyl-3-{2-[5-(2-furan-2-yl-1-methyl-1H-benzimidazol-5-yl)-2-oxo-6H-1,3,4-thiadiazin-3-yl]ethyl}urea,
1-ethyl-3-{2-[5-(2-furan-2-yl-1-methyl-1H-benzimidazol-5-yl)-2-oxo-6H-1,3,4-thiadiazin-3-yl]ethyl}urea,
1-benzyl-3-{2-[5-(2-furan-2-yl-1-methyl-1H-benzimidazol-5-yl)-2-oxo-6H-1,3,4-thiadiazin-3-yl]ethyl}urea,
1-(4-fluorobenzyl)-3-{2-[5-(2-furan-2-yl-1-methyl-1H-benzimidazol-5-yl)-2-oxo-6H-1,3,4-thiadiazin-3-yl]ethyl}urea,
1-(4-acetylphenyl)-3-{2-[5-(2-furan-2-yl-1-methyl-1H-benzimidazol-5-yl)-2-oxo-6H-1,3,4-thiadiazin-3-yl]ethyl}urea,
1-{2-[5-(2-furan-2-yl-1-methyl-1H-benzimidazol-5-yl)-2-oxo-6H-1,3,4-thiadiazin-3-yl]ethyl}-3-p-tolylurea,
1-butyl-3-{2-[5-(2-furan-2-yl-1-methyl-1H-benzimidazol-5-yl)-2-oxo-6H-1,3,4-thiadiazin-3-yl]ethyl}urea,
N-{3-[5-(2-furan-2-yl-1-methyl-1H-benzimidazol-5-yl)-2-oxo-6H-1,3,4-thiadiazin-3-yl]propyl}benzamide,
cyclopropanecarboxylic acid {3-[5-(2-furan-2-yl-1-methyl-1H-benzimidazol-5-yl)-2-oxo-6H-1,3,4-thiadiazin-3-yl]propyl}amide,
1-(4-chlorophenyl)-3-{2-[5-(2-furan-2-yl-1-methyl-1H-benzimidazol-5-yl)-2-oxo-6H-1,3,4-thiadiazin-3-yl]ethyl}urea,
1-(4-chlorophenyl)-3-{3-[5-(2-furan-2-yl-1-methyl-1H-benzimidazol-5-yl)-2-oxo-6H-1,3,4-thiadiazin-3-yl]propyl}urea,
1-butyl-3-{3-[5-(2-furan-2-yl-1-methyl-1H-benzimidazol-5-yl)-2-oxo-6H-1,3,4-thiadiazin-3-yl]propyl}urea,
1-benzyl-3-{3-[5-(2-furan-2-yl-1-methyl-1H-benzimidazol-5-yl)-2-oxo-6H-1,3,4-thiadiazin-3-yl]propyl}urea, 1-(3-fluorophenyl)-3-{3-[5-(2-furan-2-yl-1-methyl-1H-benzimidazol-5-yl)-2-oxo-6H-1,3,4-thiadiazin-3-yl]propyl}urea
N-{2-[5-(2-furan-2-yl-1-methyl-1H-benzimidazol-5-yl)-2-oxo-6H-1,3,4-thiadiazin-3-yl]ethyl}methanesulfonamide,
5-(2-furan-2-yl-1-methyl-1H-benzimidazol-5-yl)-3-(2-methoxyethyl)]-3,6-dihydro-2H-1,3,4-thiadiazin-2-one,
5-(2-furan-2-yl-1-methyl-1H-benzimidazol-5-yl)-3-(3-hydroxypropyl)]-3,6-dihydro-2H-1,3,4-thiadiazin-2-one,
5-(2-furan-2-yl-1-methyl-1H-benzimidazol-5-yl)-3-(2-hydroxyethyl)]-3,6-dihydro-2H-1,3,4-thiadiazin-2-one,
3-(3-aminopropyl)-5-(2-furan-2-yl-1-methyl-1H-benzimidazol-5-yl)]-3,6-dihydro-2H-1,3,4-thiadiazin-2-one,
3-(2-aminoethyl)-5-[2-(3-fluorophenyl)-1-methyl-1H-benzimidazol-5-yl]-6-methyl]-3,6-dihydro-2H-1,3,4-thiadiazin-2-one,
N-(2-{5-[2-(3-fluorophenyl)-1-methyl-1H-benzimidazol-5-yl]-6-methyl-2-oxo-6H-1,3,4-thiadiazin-3-yl}ethyl)-2-phenylacetamide,
N-(2-{5-[2-(3-fluorophenyl)-1-methyl-1H-benzimidazol-5-yl]-6-methyl-2-oxo-6H-1,3,4-thiadiazin-3-yl}ethyl)-4-methylbenzamide,
cyclopropanecarboxylic acid (2-{5-[2-(3-fluorophenyl)-1-methyl-1H-benzimidazol-5-yl]-6-methyl-2-oxo-6H-1,3,4-thiadiazin-3-yl}ethyl)amide,
cyclopentanecarboxylic acid (2-{5-[2-(3-fluorophenyl)-1-methyl-1H-benzimidazol-5-yl]-6-methyl-2-oxo-6H-1,3,4-thiadiazin-3-yl}ethyl)amide,
N-(2-{5-[2-(3-fluorophenyl)-1-methyl-1H-benzimidazol-5-yl]-6-methyl-2-oxo-6H-1,3,4-thiadiazin-3-yl}ethyl)-2-methoxyacetamide,
N-(2-{5-[2-(3-fluorophenyl)-1-methyl-1H-benzimidazol-5-yl]-6-methyl-2-oxo-6H-1,3,4-thiadiazin-3-yl}ethyl)nicotinamide,
N-(2-{5-[2-(3-fluorophenyl)-1-methyl-1H-benzimidazol-5-yl]-6-methyl-2-oxo-6H-1,3,4-thiadiazin-3-yl}ethyl)benzamide,
N-(2-{5-[2-(3-fluorophenyl)-1-methyl-1H-benzimidazol-5-yl]-6-methyl-2-oxo-6H-1,3,4-thiadiazin-3-yl}ethyl)acetamide,
N-(2-{5-[2-(3-fluorophenyl)-1-methyl-1H-benzimidazol-5-yl]-6-methyl-2-oxo-6H-1,3,4-thiadiazin-3-yl}ethyl)isobutyramide,
(S)-5-{2-[4-((S)-methanesulfinyl)-3-methoxyphenyl]-1H-benzimidazol-5-yl}-6-methyl]-3,6-dihydro-2H-1,3,4-thiadiazin-2-one,
(R)-5-{2-[4-((S)-methanesulfinyl)-3-methoxyphenyl]-1H-benzimidazol-5-yl}-6-methyl]-3,6-dihydro-2H-1,3,4-thiadiazin-2-one,
(S)-5-{2-[4-((R)-methanesulfinyl)-3-methoxyphenyl]-1H-benzimidazol-5-yl}-6-methyl]-3,6-dihydro-2H-1,3,4-thiadiazin-2-one,
(R)-5-{2-[4-((R)-methanesulfinyl)-3-methoxyphenyl]-1H-benzimidazol-5-yl}-6-methyl]-3,6-dihydro-2H-1,3,4-thiadiazin-2-one,
1-(4-acetylphenyl)-3-(2-{5-[2-(3-fluorophenyl)-1-methyl-1H-benzimidazol-5-yl]-6-methyl-2-oxo-6H-1,3,4-thiadiazin-3-yl}ethyl)urea,
1-(3-fluorophenyl)-3-(2-{5-[2-(3-fluorophenyl)-1-methyl-1H-benzimidazol-5-yl]-6-methyl-2-oxo-6H-1,3,4-thiadiazin-3-yl}ethyl)urea,
5-[1-cyclopropylmethyl-2-(1-methyl-1H-pyrrol-2-yl)-1H-benzimidazol-5-yl]-6-methyl]-3,6-dihydro-2H-1,3,4-thiadiazin-2-one,
5-[1-cyclopropylmethyl-2-(1-methyl-1H-imidazol-2-yl)-1H-benzimidazol-5-yl]-6-methyl]-3,6-dihydro-2H-1,3,4-thiadiazin-2-one,
5-(1-cyclopropylmethyl-2-thiophen-3-yl-1H-benzimidazol-5-yl)-6-methyl]-3,6-dihydro-2H-1,3,4-thiadiazin-2-one,
5-[1-cyclopropylmethyl-2-(2-methoxyphenyl)-1H-benzimidazol-5-yl]-6-methyl]-3,6-dihydro-2H-1,3,4-thiadiazin-2-one,
5-[1-cyclopropylmethyl-2-(4-methoxyphenyl)-1H-benzimidazol-5-yl]-6-methyl]-3,6-dihydro-2H-1,3,4-thiadiazin-2-one,
5-[1-cyclopropylmethyl-2-(3-hydroxy-4-methoxyphenyl)-1H-benzimidazol-5-yl]-6-methyl]-3,6-dihydro-2H-1,3,4-thiadiazin-2-one.

Method for Measuring the Inhibition of Recombinant Human Liver Fructose-1,6-bis-phosphatase The enzymatic activity is measured by using a spectrophotometric method by means of reactions coupling the formation of the product (fructose-6-phosphate) to the reduction of NADP+ via phosphoglucoisomerase (PGI) and glucose-6-phosphate dehydrogenase (G6PDH).

The reaction mixtures (250 µl) are prepared in 96-well plates and are composed of 20 mM triethanolamine, pH 7.5, 2 mM $MgCl_2$, 0.1 mM EDTA, 40 mM ammonium sulfate, 0.5 mM NADP, 1 U/ml G6PDH, 1 U/ml PGI and 0.167 mM of substrate (fructose-1,6-bisphosphate).

The inhibitors are prepared at $10^{-2}$ M in 100% DMSO and tested at $10^{-5}$ M (DMSO 0.1% final).

The reactions are initiated by addition of recombinant human liver enzyme fructose-1,6-bisphosphatase and monitored for 30 minutes at 340 nm, at room temperature, in a Tecan plate reader.

Inhibition of Recombinant Human Liver Fructose-1,6-Bisphosphatase

| Example | Structure | Inhibition of human F-1,6-BPase $IC_{50}$ µM |
|---|---|---|
| 12-6 | 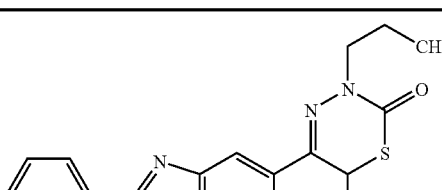 | 8.5 |

| Example | Structure | Inhibition of human F-1,6-BPase IC$_{50}$ μM |
|---|---|---|
| 12-3 | 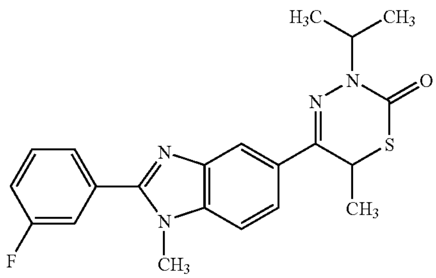 | 7 |
| 26-4 | 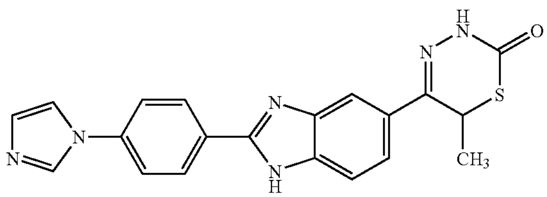 | 3.6 |
| 26-3 | 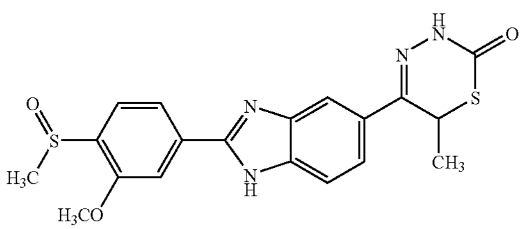 | 6.4 |
| 12-7 | 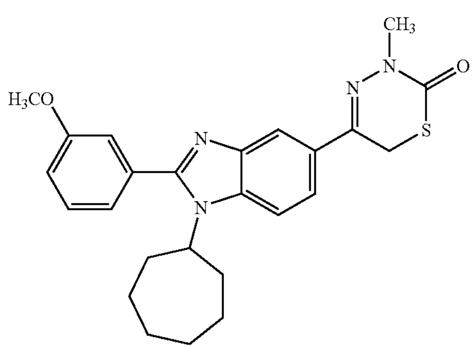 | 36 |

Effects of the Various Compounds Described Previously on the Hepatic Production of Glucose in Rat Hepatocyte Primary Cultures The hepatocytes are isolated from Wistar rat liver via the collagenase perfusion technique described by Seglen (Methods Cell Biol. 1975; 13, 29-83). The cell viability is confirmed by the exclusion test with trypan blue. The isolated hepatocytes are suspended in a William's medium supplemented with foetal calf serum (10%) in 6-well plates. After a 4-hour attachment period, the medium is aspirated to remove the cell debris and replaced with a serum-free and glucose-free MEM medium. The hepatocytes are then cultured for 16 to 18 hours (37° C.; 5% CO$_2$). At the end of culturing and after having aspirated the medium, the glucose production is measured by incubating the hepatocytes for 3 hours in a Krebs buffer supplemented with dihydroxyacetone (DHA) as neoglucogenesis substrate, in the presence or absence of the various compounds described previously. The amount of glucose in the medium is measured in each culture well via a test with glucose oxidase (GOD). The cell protein content is evaluated via the Lowry method. The results are expressed in nanomoles of glucose produced per mg of cell protein. The activity of the test compounds is expressed as a percentage of the control (production of glucose in the presence of DHA but without compounds).
Inhibition of Hepatic Glucose Production

| Example | Structure | Hepatic glucose production. % of the control at 30 µM |
|---|---|---|
| 26 | 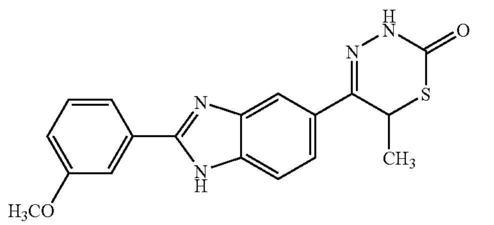 | 38 |
| 26-3 | 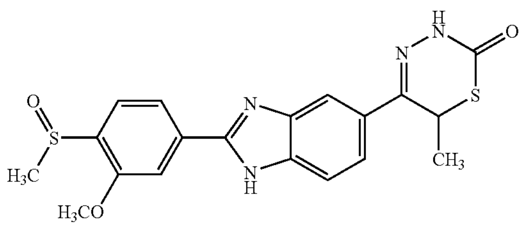 | 34 |
| 26-4 | 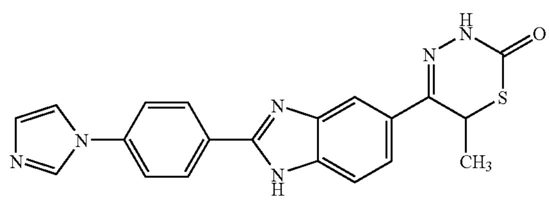 | 28 |

The invention claimed is:
1. A compound of formula (I):

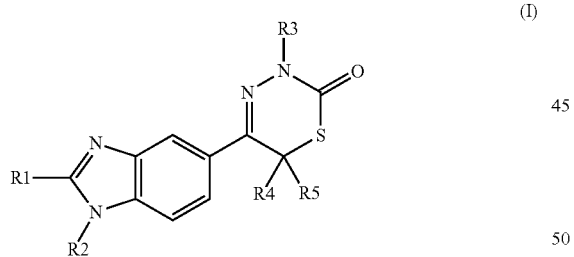

(I)

in which
R1 is an aryl group optionally substituted by one to four identical or different groups independently chosen from halogen, —OR, perhaloalkyl-, —S(O)$_p$—R, —NRR', —S—CH$_2$—CN or heteroaryl, or R1 is a -heteroaryl group which is optionally substituted by one or more -alkyl groups;
p is equal to 0, 1 or 2,
R and R', which may be identical or different, are independently chosen from H, -alkyl, -aryl, -heteroaryl, -cycloalkyl and -heterocycloalkyl, it being understood that R and R' may form a saturated or unsaturated mono- or bicyclic system of 3 to 10 atoms comprising from 1 to 3 heteroatoms;
R2 represents a group chosen, without preference, from:
H,
alkyl-, alkoxyalkyl-, alkenyl-, alkynyl-, each of these groups possibly being substituted by one or more groups chosen from Y,
aryl-, arylalkyl-, aryloxyalkyl-, arylalkyloxyalkyl-, arylthioalkyl-, arylalkylthio-, alkyl-,
heteroaryl-, heteroarylalkyl-, heteroaryloxyalkyl-, heteroarylalkyloxyalkyl-, heteroarylthioalkyl-, heteroarylalkylthioalkyl-,
cycloalkyl-, cycloalkylalkyl-, cycloalkyloxyalkyl-, cycloalkylalkyloxyalkyl-, cycloalkylthioalkyl-, cycloalkylalkylthioalkyl-,
heterocycloalkyl-, heterocycloalkylalkyl-, heterocycloalkyloxyalkyl-, heterocycloalkylalkyloxyalkyl-, heterocycloalkylthioalkyl-, heterocycloalkylalkylthioalkyl-,
each of the groups aryl-, heteroaryl-, cycloalkyl- and heterocycloalkyl- possibly being optionally substituted by one or more groups chosen, without preference, from Y;
R3 represents a group chosen, without preference, from:
H,
alkyl-, alkoxyalkyl-, hydroxyalkyl-, alkenyl-, alkynyl-, each of these groups possibly being optionally substituted by one or more groups chosen from Y,
aryl-, arylalkyl-, aryloxyalkyl-, arylalkyloxyalkyl-, arylthioalkyl-, arylalkylthioalkyl-,
heteroaryl-, heteroarylalkyl-, heteroaryloxyalkyl-, heteroarylalkyloxyalkyl-, heteroarylthioalkyl-, heteroarylalkylthioalkyl-,
cycloalkyl-, cycloalkylalkyl-, cycloalkyloxyalkyl-, cycloalkylalkyloxyalkyl-, cycloalkylthioalkyl-, cycloalkylalkylthioalkyl-, heterocycloalkyl-, heterocycloalkylalkyl-, heterocycloalkyloxyalkyl-, heterocycloalkylalkyloxyalkyl-, heterocycloalkylthioalkyl-, heterocycloalkylalkylthioalkyl-, each of the groups aryl-, heteroaryl-, cycloalkyl- and heterocycloalkyl- possibly being optionally substituted by one or more groups chosen, without preference, from Y;

R4 and R5 independently represent a group chosen, without preference, from:
H,
W;

Y represents a group chosen, without preference, from:
Hydroxyl-; halo-; trifluoromethoxy-; trifluoromethyl-; alkyloxy-; carboxyl-; alkoxycarbonyl-; carbamoyl-; sulfamoyl-; nitro-; guanidino-; amidino-; aryl-; heteroaryl-; amino-;

in which R8 represents a group chosen, without preference, from W;

in which R9 represents a group chosen, without preference, from W and p=0, 1 or 2;

—(CH$_2$)$n$—O—R10 in which R10 represents a group chosen, without preference, from
H,
W,
and n is an integer between 0 and 8;

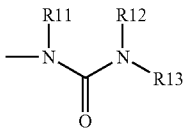

in which R11, R12 and R13 independently represent a group chosen, without preference, from:
H,
W,
it being understood that R12 and R13 may form a saturated or unsaturated mono- or bicyclic system of 3 to 10 atoms comprising from 1 to 3 heteroatoms;

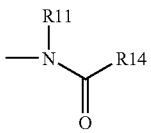

in which R11 represents a group chosen, without preference, from:
H,
W,
and in which R14 represents a group chosen, without preference, from W;

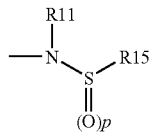

in which R11 represents a group chosen, without preference, from:
H,
W,
and in which R15 represents a group chosen, without preference, from W and p=0, 1 or 2;
in which:
Amino denotes a group

in which Ra and Rb are chosen, without preference, from:
H,
W,
it being understood that Ra and Rb may form a saturated or unsaturated mono- or bicyclic system of 3 to 10 atoms comprising from 1 to 3 heteroatoms; and W represents a group chosen, without preference, from:
alkyl-, alkenyl-, alkynyl-, aryl-, arylalkyl-, aryloxyalkyl-, arylalkyloxyalkyl-, arylthioalkyl-, arylalkylthioalkyl-, heteroaryl-, heteroarylalkyl-, heteroaryloxyalkyl-, heteroarylalkyloxyalkyl-, heteroarylthioalkyl-, heteroarylalkylthioalkyl-, cycloalkyl-, cycloalkylalkyl-, cycloalkyloxyalkyl-, cycloalkylalkyloxyalkyl-, cycloalkylthioalkyl-, cycloalkylalkylthioalkyl-, heterocycloalkyl-, heterocycloalkylalkyl-, heterocycloalkyloxyalkyl-, heterocycloalkylalkyloxyalkyl-, heterocycloalkylthioalkyl-, heterocycloalkylalkylthioalkyl-, each of these groups possibly being optionally substituted by one or more groups chosen, without preference, from hydroxyl-, halo-, trifluoromethoxy-, trifluoromethyl-, alkyloxy-, carboxyl, alkoxycarbonyl-, carbamoyl-, sulfamoyl-, nitro-, guanidino-, amidino-, aryl-, heteroaryl-, amino- which has the same meaning as above, acetyl-;

or the tautomeric forms thereof, enantiomers thereof, diastereoisomers thereof, epimers thereof, pharmaceutically acceptable salts thereof, or mixtures thereof.

2. A compound according to claim 1, wherein R4 and R5, which may be identical or different, are independently chosen from a hydrogen atom and an -alkyl group.

3. A compound according to claim 1, wherein
R1 represents an aryl group optionally substituted by one to four identical or different groups independently chosen from halogen, —OR, perhaloalkyl-, —S(O)$_p$—R, —NRR', —S—CH$_2$—CN or heteroaryl; or a -heteroaryl group, optionally substituted by one or more -alkyl groups;
R2 represents a hydrogen atom; a -cycloalkyl group; an -alkyl group optionally substituted by a -cycloalkyl or -aryl group;

R4 and R5, which may be identical or different, are independently chosen from a hydrogen atom and an -alkyl group;

R3 represents:
a hydrogen atom;
an -alkyl group, optionally substituted by one or more groups chosen from:
OR, —O-heterocycloalkyl,
cycloalkyl,
heterocycloalkyl,
COOR,
CONRR',
NRR',
NRCO-alkyl, —NRCO-alkyl-aryl, —NRCO-cycloalkyl, —NRCO-aryl, —NRCO-heteroaryl, the aryl group being optionally substituted by a halogen atom or an alkyl group,
NRCOO-alkyl,
NRCO—NR-alkyl, —NRCO—NR-aryl or —NRCO—NR-alkyl-aryl, in which the aryl group is optionally substituted by a halogen atom or a group —COR;
NRCO—NR-cycloalkyl,
$NRS(O)_p$-aryl, —$NRS(O)_p$-alkyl, or
aryl or —O-aryl, each aryl group being optionally substituted by one or more substituents chosen from halogen atoms and the groups -alkyl, —OR, perhaloalkyl-, perhaloalkyloxy- and —$S(O)_p$—R;
p=0, 1 or 2;
R and R', which may be identical or different, are independently chosen from H, -alkyl, -aryl, -heteroaryl, -cycloalkyl and -heterocycloalkyl, it being understood that R and R' may form a saturated or unsaturated mono- or bicyclic system of 3 to 10 atoms comprising from 1 to 3 heteroatoms, or the tautomeric forms thereof, enantiomers thereof, diastereoisomers thereof, epimers thereof, pharmaceutically acceptable salts thereof, or mixtures thereof.

4. A compound according to claim 1, wherein

R1 represents an aryl group optionally substituted by one to four identical or different groups independently chosen from halogen, —O-alkyl and —$S(O)_p$-alkyl in which p=0, 1 or 2;

R2 represents a hydrogen atom; a -cycloalkyl group; an -alkyl group;

R4 and R5, which may be identical or different, are independently chosen from a hydrogen atom and an -alkyl group;

R3 represents:
a hydrogen atom;
an -alkyl group, and the tautomeric forms thereof, enantiomers thereof, diastereoisomers thereof, epimers thereof, pharmaceutically acceptable salts thereof, or mixtures thereof.

5. A compound according to claim 1, wherein said compound is selected from:

5-[2-(4-methoxyphenyl)-1H-benzimidazol-5-yl]-3,6-dihydro-2H-1,3,4-thiadiazin-2-one,
6-methyl-5-[2-(1H-pyrazol-3-yl)-1H-benzimidazol-5-yl]-3,6-dihydro-2H-1,3,4-thiadiazin-2-one,
6-methyl-5-[2-(2-thienyl)-1H-benzimidazol-5-yl]-3,6-dihydro-2H-1,3,4-thiadiazin-2-one,
5-[2-(3-methoxyphenyl)-1H-benzimidazol-5-yl]-6-methyl-3,6-dihydro-2H-1,3,4-thiadiazin-2-one,
6-methyl-5-(2-pyrid-4-yl-1H-benzimidazol-5-yl)-3,6-dihydro-2H-1,3,4-thiadiazin-2-one,
5-[2-(3-methoxy-4-(methylthio)phenyl]-1H-benzimidazol-5-yl]-6-methyl-3,6-dihydro-2H-1,3,4-thiadiazin-2-one,
5-[2-(2-methoxy-4-(methylthio)phenyl]-1H-benzimidazol-5-yl]-6-methyl-3,6-dihydro-2H-1,3,4-thiadiazin-2-one,
6-methyl-5-[2-(1,3-thiazol-4-yl)-1H-benzimidazol-5-yl]-3,6-dihydro-2H-1,3,4-thiadiazin-2-one,
5-{2-[3-methoxy-4-(methylsulfinyl)phenyl]-1H-benzimidazol-5-yl}-6-methyl-3,6-dihydro-2H-1,3,4-thiadiazin-2-one,
5-[2-(1H-imidazol-1-yl)-1H-benzimidazol-5-yl]-6-methyl-3,6-dihydro-2H-1,3,4-thiadiazin-2-one,
5-{2-[4-(dimethylamino)phenyl]-1H-benzimidazol-5-yl}-6-methyl-3,6-dihydro-2H-1,3,4-thiadiazin-2-one,
6-methyl-5-{2-[4-(methylthio)phenyl]-1H-benzimidazol-5-yl}-3,6-dihydro-2H-1,3,4-thiadiazin-2-one,
6-methyl-5-{2-[4-(methylsulfinyl)phenyl]-1H-benzimidazol-5-yl}-3,6-dihydro-2H-1,3,4-thiadiazin-2-one,
5-[2-(2-methoxyphenyl)-1H-benzimidazol-5-yl]-6-methyl-3,6-dihydro-2H-1,3,4-thiadiazin-2-one,
5-[2-(3-methoxyphenyl)-1H-benzimidazol-5-yl]-6-methyl-3,6-dihydro-2H-1,3,4-thiadiazin-2-one,
3-methoxy-4-[5-(6-methyl-2-oxo-3,6-dihydro-2H-1,3,4-thiadiazin-5-yl)-1H-benzimidazol-2-yl]phenyl thiocyanate,
5-{2-[2-chloro-4-(methylthio)phenyl]-1H-benzimidazol-5-yl}-6-methyl-3,6-dihydro-2H-1,3,4-thiadiazin-2-one,
6-methyl-5-{2-[4-(pyrid-4-ylamino)phenyl]-1H-benzimidazol-5-yl}-3,6-dihydro-2H-1,3,4-thiadiazin-2-one,
5-[2-(4-methoxyphenyl)-1H-benzimidazol-5-yl]-3,6-dimethyl-3,6-dihydro-2H-1,3,4-thiadiazin-2-one,
3,6-dimethyl-5-[2-(1H-pyrazol-3-yl)-1H-benzimidazol-5-yl]-3,6-dihydro-2H-1,3,4-thiadiazin-2-one,
3,6-dimethyl-5-[2-(1,3-thiazol-4-yl)-1H-benzimidazol-5-yl]-3,6-dihydro-2H-1,3,4-thiadiazin-2-one,
3,6-dimethyl-5-(2-pyrid-4-yl-1H-benzimidazol-5-yl)-3,6-dihydro-2H-1,3,4-thiadiazin-2-one,
3-ethyl-6-methyl-5-[2-(1H-pyrazol-3-yl)-1H-benzimidazol-5-yl]-3,6-dihydro-2H-1,3,4-thiadiazin-2-one,
3-ethyl-6-methyl-5-[2-(1,3-thiazol-4-yl)-1H-benzimidazol-5-yl]-3,6-dihydro-2H-1,3,4-thiadiazin-2-one,
3-ethyl-5-[2-(4-methoxyphenyl)-1H-benzimidazol-5-yl]-6-methyl-3,6-dihydro-2H-1,3,4-thiadiazin-2-one,
5-[1-cycloheptyl-2-(3-methoxyphenyl)-1H-benzimidazol-5-yl]-3,6-dihydro-2H-1,3,4-thiadiazin-2-one,
5-[1-isobutyl-2-(3-methoxyphenyl)-1H-benzimidazol-5-yl]-3,6-dihydro-2H-1,3,4-thiadiazin-2-one,
5-[1-isobutyl-2-(3-methoxyphenyl)-1H-benzimidazol-5-yl]-3-(4-methylbenzyl)-3,6-dihydro-2H-1,3,4-thiadiazin-2-one,
3-(4-tert-butylbenzyl)-5-[1-isobutyl-2-(3-methoxyphenyl)-1H-benzimidazol-5-yl]-3,6-dihydro-2H-1,3,4-thiadiazin-2-one,
3-(2-fluorobenzyl)-5-[1-isobutyl-2-(3-methoxyphenyl)-1H-benzimidazol-5-yl]-3,6-dihydro-2H-1,3,4-thiadiazin-2-one,
5-[1-cycloheptyl-2-(3-methoxyphenyl)-1H-benzimidazol-5-yl]-3-methyl]-3,6-dihydro-2H-1,3,4-thiadiazin-2-one,
5-[1-cycloheptyl-2-(3-methoxyphenyl)-1H-benzimidazol-5-yl]-3-propyl]-3,6-dihydro-2H-1,3,4-thiadiazin-2-one,
5-[1-cycloheptyl-2-(3-methoxyphenyl)-1H-benzimidazol-5-yl]-3-isobutyl]-3,6-dihydro-2H-1,3,4-thiadiazin-2-one, 5-[1-cycloheptyl-2-(3-methoxyphenyl)-1H-benzimidazol-5-yl]-3-(2-methoxyethyl)]-3,6-dihydro-2H-1,3,4-thiadiazin-2-one,
5-[1-isobutyl-2-(3-methoxyphenyl)-1H-benzimidazol-5-yl]-3-(3-methylbenzyl)]-3,6-dihydro-2H-1,3,4-thiadiazin-2-one,
3-(3-fluorobenzyl)-5-[1-isobutyl-2-(3-methoxyphenyl)-1H-benzimidazol-5-yl]-3,6-dihydro-2H-1,3,4-thiadiazin-2-one,
3-benzyl-5-[1-isobutyl-2-(3-methoxyphenyl)-1H-benzimidazol-5-yl]-3,6-dihydro-2H-1,3,4-thiadiazin-2-one,
3-(4-fluorobenzyl)-5-[1-isobutyl-2-(3-methoxyphenyl)-1H-benzimidazol-5-yl]-3,6-dihydro-2H-1,3,4-thiadiazin-2-one,
3-(3-chlorobenzyl)-5-[1-isobutyl-2-(3-methoxyphenyl)-1H-benzimidazol-5-yl]-3,6-dihydro-2H-1,3,4-thiadiazin-2-one,
5-[1-isobutyl-2-(3-methoxyphenyl)-1H-benzimidazol-5-yl]-3-(3-methoxybenzyl)]-3,6-dihydro-2H-1,3,4-thiadiazin-2-one,
5-[1-isobutyl-2-(3-methoxyphenyl)-1H-benzimidazol-5-yl]-3-(4-trifluoromethoxybenzyl)]-3,6-dihydro-2H-1,3,4-thiadiazin-2-one,
5-[1-isobutyl-2-(3-methoxyphenyl)-1H-benzimidazol-5-yl]-3-(3-trifluoromethylbenzyl)]-3,6-dihydro-2H-1,3,4-thiadiazin-2-one,
5-[1-isobutyl-2-(3-methoxyphenyl)-1H-benzimidazol-5-yl]-3-(4-trifluoromethylbenzyl)]-3,6-dihydro-2H-1,3,4-thiadiazin-2-one,
3-(2,3-difluorobenzyl)-5-[1-isobutyl-2-(3-methoxyphenyl)-1H-benzimidazol-5-yl]-3,6-dihydro-2H-1,3,4-thiadiazin-2-one,
3-(2,4-difluorobenzyl)-5-[1-isobutyl-2-(3-methoxyphenyl)-1H-benzimidazol-5-yl]-3,6-dihydro-2H-1,3,4-thiadiazin-2-one,
3-(2,5-difluorobenzyl)-5-[1-isobutyl-2-(3-methoxyphenyl)-1H-benzimidazol-5-yl]-3,6-dihydro-2H-1,3,4-thiadiazin-2-one,
3-(2,6-difluorobenzyl)-5-[1-isobutyl-2-(3-methoxyphenyl)-1H-benzimidazol-5-yl]-3,6-dihydro-2H-1,3,4-thiadiazin-2-one,
3-(3,4-difluorobenzyl)-5-[1-isobutyl-2-(3-methoxyphenyl)-1H-benzimidazol-5-yl]-3,6-dihydro-2H-1,3,4-thiadiazin-2-one,
3-(3,5-dimethoxybenzyl)-5-[1-isobutyl-2-(3-methoxyphenyl)-1H-benzimidazol-5-yl]-3,6-dihydro-2H-1,3,4-thiadiazin-2-one,
3-cyclopropylmethyl-5-[1-isobutyl-2-(3-methoxyphenyl)-1H-benzimidazol-5-yl]-3,6-dihydro-2H-1,3,4-thiadiazin-2-one,
3-(2-hydroxyethyl)-5-[1-isobutyl-2-(3-methoxyphenyl)-1H-benzimidazol-5-yl]-3,6-dihydro-2H-1,3,4-thiadiazin-2-one,
3-ethyl-5-[1-isobutyl-2-(3-methoxyphenyl)-1H-benzimidazol-5-yl]-3,6-dihydro-2H-1,3,4-thiadiazin-2-one,
5-[1-isobutyl-2-(3-methoxyphenyl)-1H-benzimidazol-5-yl]-3-propyl]-3,6-dihydro-2H-1,3,4-thiadiazin-2-one,
5-[1-isobutyl-2-(3-methoxyphenyl)-1H-benzimidazol-5-yl]-3-isopropyl]-3,6-dihydro-2H-1,3,4-thiadiazin-2-one,
2-{5-[1-isobutyl-2-(3-methoxyphenyl)-1H-benzimidazol-5-yl]-2-oxo-6H-1,3,4-thiadiazin-3-yl}acetamide,
5-[1-isobutyl-2-(3-methoxyphenyl)-1H-benzimidazol-5-yl]-3-(2-methoxyethyl)]-3,6-dihydro-2H-1,3,4-thiadiazin-2-one,
{5-[1-isobutyl-2-(3-methoxyphenyl)-1H-benzimidazol-5-yl]-2-oxo-6H-1,3,4-thiadiazin-3-yl}acetic acid,
5-[1-isobutyl-2-(3-methoxyphenyl)-1H-benzimidazol-5-yl]-6-methyl]-3,6-dihydro-2H-1,3,4-thiadiazin-2-one,
3-(2-hydroxyethyl)-5-[1-isobutyl-2-(3-methoxyphenyl)-1H-benzimidazol-5-yl]-6-methyl]-3,6-dihydro-2H-1,3,4-thiadiazin-2-one,
5-[1-isobutyl-2-(3-methoxyphenyl)-1H-benzimidazol-5-yl]-3-propyl]-3,6-dihydro-2H-1,3,4-thiadiazin-2-one,
5-[1-isobutyl-2-(3-methoxyphenyl)-1H-benzimidazol-5-yl]-3,6-dimethyl]-3,6-dihydro-2H-1,3,4-thiadiazin-2-one,
3-ethyl-5-[1-isobutyl-2-(3-methoxyphenyl)-1H-benzimidazol-5-yl]-6-methyl]-3,6-dihydro-2H-1,3,4-thiadiazin-2-one,
5-[1-isobutyl-2-(3-methoxyphenyl)-1H-benzimidazol-5-yl]-3-isopropyl-6-methyl]-3,6-dihydro-2H-1,3,4-thiadiazin-2-one,
3-cyclopropylmethyl-5-[1-isobutyl-2-(3-methoxyphenyl)-1H-benzimidazol-5-yl]-6-methyl]-3,6-dihydro-2H-1,3,4-thiadiazin-2-one,
3-ethyl-5-[2-(3-methoxyphenyl)-1-methyl-1H-benzimidazol-5-yl]-3,6-dihydro-2H-1,3,4-thiadiazin-2-one,
5-[2-(3-methoxyphenyl)-1-methyl-1H-benzimidazol-5-yl]-3-propyl]-3,6-dihydro-2H-1,3,4-thiadiazin-2-one hydrochloride,
3-cyclohexylmethyl-5-[2-(3-methoxyphenyl)-1-methyl-1H-benzimidazol-5-yl]-3,6-dihydro-2H-1,3,4-thiadiazin-2-one,
3-[2-(4-fluorophenoxy)ethyl]-5-[2-(3-methoxyphenyl)-1-methyl-1H-benzimidazol-5-yl]-3,6-dihydro-2H-1,3,4-thiadiazin-2-one,
5-[2-(3-methoxyphenyl)-1-methyl-1H-benzimidazol-5-yl]-3-methyl]-3,6-dihydro-2H-1,3,4-thiadiazin-2-one,
3-isopropyl-5-[2-(3-methoxyphenyl)-1-methyl-1H-benzimidazol-5-yl]-3,6-dihydro-2H-1,3,4-thiadiazin-2-one,
3-isobutyl-5-[2-(3-methoxyphenyl)-1-methyl-1H-benzimidazol-5-yl]-3,6-dihydro-2H-1,3,4-thiadiazin-2-one,
3-cyclopropylmethyl-5-[2-(3-methoxyphenyl)-1-methyl-1H-benzimidazol-5-yl]-3,6-dihydro-2H-1,3,4-thiadiazin-2-one,
5-[2-(3-methoxyphenyl)-1-methyl-1H-benzimidazol-5-yl]-6-methyl]-3,6-dihydro-2H-1,3,4-thiadiazin-2-one,
3-ethyl-5-[2-(3-methoxyphenyl)-1-methyl-1H-benzimidazol-5-yl]-6-methyl]-3,6-dihydro-2H-1,3,4-thiadiazin-2-one,
5-[2-(3-methoxyphenyl)-1-methyl-1H-benzimidazol-5-yl]-6-methyl-3-propyl]-3,6-dihydro-2H-1,3,4-thiadiazin-2-one,
5-[2-(3-methoxyphenyl)-1-methyl-1H-benzimidazol-5-yl]-6-methyl-3-(2-piperidin-1-ylethyl)]-3,6-dihydro-2H-1,3,4-thiadiazin-2-one,
3-isobutyl-5-[2-(3-methoxyphenyl)-1-methyl-1H-benzimidazol-5-yl]-6-methyl]-3,6-dihydro-2H-1,3,4-thiadiazin-2-one,
5-[2-(3-methoxyphenyl)-1-methyl-1H-benzimidazol-5-yl]-3,6-dimethyl]-3,6-dihydro-2H-1,3,4-thiadiazin-2-one,
6-methyl-5-[1-methyl-2-(3-trifluoromethylphenyl)-1H-benzimidazol-5-yl]-3,6-dihydro-2H-1,3,4-thiadiazin-2-one,
3-benzyl-6-methyl-5-[1-methyl-2-(3-trifluoromethylphenyl)-1H-benzimidazol-5-yl]-3,6-dihydro-2H-1,3,4-thiadiazin-2-one,
3-cyclopropylmethyl-6-methyl-5-[1-methyl-2-(3-trifluoromethylphenyl)-1H-benzimidazol-5-yl]-3,6-dihydro-2H-1,3,4-thiadiazin-2-one, 3-isopropyl-6-methyl-5-[1-methyl-2-(3-trifluoromethylphenyl)-1H-benzimidazol-5-yl]-3,6-dihydro-2H-1,3,4-thiadiazin-2-one,
3,6-dimethyl-5-[1-methyl-2-(3-trifluoromethylphenyl)-1H-benzimidazol-5-yl]-3,6-dihydro-2H-1,3,4-thiadiazin-2-one,
3-ethyl-6-methyl-5-[1-methyl-2-(3-trifluoromethylphenyl)-1H-benzimidazol-5-yl]-3,6-dihydro-2H-1,3,4-thiadiazin-2-one,
5-[1-benzyl-2-(1-methyl-1H-pyrrol-2-yl)-1H-benzimidazol-5-yl]-6-methyl]-3,6-dihydro-2H-1,3,4-thiadiazin-2-one,
5-[1-benzyl-2-(1-methyl-1H-imidazol-2-yl)-1H-benzimidazol-5-yl]-6-methyl]-3,6-dihydro-2H-1,3,4-thiadiazin-2-one,
5-(1-benzyl-2-thiophen-2-yl-1H-benzimidazol-5-yl)-6-methyl]-3,6-dihydro-2H-1,3,4-thiadiazin-2-one,
5-[1-benzyl-2-(3-methoxyphenyl)-1H-benzimidazol-5-yl]-6-methyl]-3,6-dihydro-2H-1,3,4-thiadiazin-2-one,
5-[1-benzyl-2-(4-methoxyphenyl)-1H-benzimidazol-5-yl]-6-methyl]-3,6-dihydro-2H-1,3,4-thiadiazin-2-one,
5-[1-benzyl-2-(3-hydroxy-4-methoxyphenyl)-1H-benzimidazol-5-yl]-6-methyl]-3,6-dihydro-2H-1,3,4-thiadiazin-2-one,
5-[1-benzyl-2-(2,4-dihydroxyphenyl)-1H-benzimidazol-5-yl]-6-methyl]-3,6-dihydro-2H-1,3,4-thiadiazin-2-one,
5-[1-benzyl-2-(3,4-dihydroxyphenyl)-1H-benzimidazol-5-yl]-6-methyl]-3,6-dihydro-2H-1,3,4-thiadiazin-2-one,
5-[1-benzyl-2-(3,4,5-trihydroxyphenyl)-1H-benzimidazol-5-yl]-6-methyl]-3,6-dihydro-2H-1,3,4-thiadiazin-2-one,
6-methyl-5-[1-methyl-2-(1-methyl-1H-pyrrol-2-yl)-1H-benzimidazol-5-yl]-3,6-dihydro-2H-1,3,4-thiadiazin-2-one,
5-[2-(1H-imidazol-4-yl)-1-methyl-1H-benzimidazol-5-yl]-6-methyl]-3,6-dihydro-2H-1,3,4-thiadiazin-2-one,
5-[2-(1H-imidazol-2-yl)-1-methyl-1H-benzimidazol-5-yl]-6-methyl]-3,6-dihydro-2H-1,3,4-thiadiazin-2-one,
6-methyl-5-[1-methyl-2-(5-methyl-3H-imidazol-4-yl)-1H-benzimidazol-5-yl]-3,6-dihydro-2H-1,3,4-thiadiazin-2-one,
6-methyl-5-[1-methyl-2-(1-methyl-1H-imidazol-2-yl)-1H-benzimidazol-5-yl]-3,6-dihydro-2H-1,3,4-thiadiazin-2-one,
6-methyl-5-(1-methyl-2-thiophen-2-yl-1H-benzimidazol-5-yl)]-3,6-dihydro-2H-1,3,4-thiadiazin-2-one,
6-methyl-5-(1-methyl-2-thiophen-3-yl-1H-benzimidazol-5-yl)]-3,6-dihydro-2H-1,3,4-thiadiazin-2-one,
5-[2-(2-methoxyphenyl)-1-methyl-1H-benzimidazol-5-yl]-6-methyl]-3,6-dihydro-2H-1,3,4-thiadiazin-2-one,
5-[2-(4-methoxyphenyl)-1-methyl-1H-benzimidazol-5-yl]-6-methyl]-3,6-dihydro-2H-1,3,4-thiadiazin-2-one,
5-[2-(3-hydroxy-4-methoxyphenyl)-1-methyl-1H-benzimidazol-5-yl]-6-methyl]-3,6-dihydro-2H-1,3,4-thiadiazin-2-one,
5-[2-(3,4-dihydroxyphenyl)-1-methyl-1H-benzimidazol-5-yl]-6-methyl]-3,6-dihydro-2H-1,3,4-thiadiazin-2-one,
6-methyl-5-[1-methyl-2-(3,4,5-trihydroxyphenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-(3-methylbenzyl)]-3,6-dihydro-2H-1,3,4-thiadiazin-2-one,
5-[1-ethyl-2-(3-fluorophenyl)-1H-benzimidazol-5-yl]-3-(4-methylbenzyl)]-3,6-dihydro-2H-1,3,4-thiadiazin-2-one,
3-(4-tert-butylbenzyl)-5-[1-ethyl-2-(3-fluorophenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-(2-fluorobenzyl)]-3,6-dihydro-2H-1,3,4-thiadiazin-2-one,
5-[1-ethyl-2-(3-fluorophenyl)-1H-benzimidazol-5-yl]-3-(3-fluorobenzyl)]-3,6-dihydro-2H-1,3,4-thiadiazin-2-one,
3-benzyl-5-[1-ethyl-2-(3-fluorophenyl)-1H-benzimidazol-5-yl]-3,6-dihydro-2H-1,3,4-thiadiazin-2-one,
3-(3-chlorobenzyl)-5-[1-ethyl-2-(3-fluorophenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-methyl]-3,6-dihydro-2H-1,3,4-thiadiazin-2-one,
3-cyclohexylmethyl-5-[1-ethyl-2-(3-fluorophenyl)-1H-benzimidazol-5-yl]-3,6-dihydro-2H-1,3,4-thiadiazin-2-one,
3-(2-dimethylaminoethyl)-5-[1-ethyl-2-(3-fluorophenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-(2-pyrrolidin-1-ylethyl)]-3,6-dihydro-2H-1,3,4-thiadiazin-2-one,
5-[1-isobutyl-2-(3-methoxyphenyl)-1H-benzimidazol-5-yl]-3-(3-methylbenzyl)]-3,6-dihydro-2H-1,3,4-thiadiazin-2-one,
5-[2-(4-methoxyphenyl)-1H-benzimidazol-5-yl]-6-methyl]-3,6-dihydro-2H-1,3,4-thiadiazin-2-one,
3-(2-dimethylaminoethyl)-6-methyl-5-[1-methyl-2-(3-trifluoromethylphenyl)-1H-benzimidazol-5-yl]-3,6-dihydro-2H-1,3,4-thiadiazin-2-one,
6-methyl-5-[1-methyl-2-(3-trifluoromethylphenyl)-1H-benzimidazol-5-yl]-3-(2-piperidin-1-ylethyl)]-3,6-dihydro-2H-1,3,4-thiadiazin-2-one,
3-cyclohexylmethyl-6-methyl-5-[1-methyl-2-(3-trifluoromethylphenyl)-1H-benzimidazol-5-yl]-3,6-dihydro-2H-1,3,4-thiadiazin-2-one,
6-methyl-5-[1-methyl-2-(3-trifluoromethylphenyl)-1H-benzimidazol-5-yl]-3-(2-morpholin-4-ylethyl)]-3,6-dihydro-2H-1,3,4-thiadiazin-2-one,
6-methyl-5-[1-methyl-2-(3-trifluoromethylphenyl)-1H-benzimidazol-5-yl]-3-(2-pyrrolidin-1-ylethyl)]-3,6-dihydro-2H-1,3,4-thiadiazin-2-one,
2-{6-methyl-5-[1-methyl-2-(3-trifluoromethylphenyl)-1H-benzimidazol-5-yl]-2-oxo-6H-1,3,4-thiadiazin-3-yl}acetamide,
3-(2-methoxyethyl)-6-methyl-5-[1-methyl-2-(3-trifluoromethylphenyl)-1H-benzimidazol-5-yl]-3,6-dihydro-2H-1,3,4-thiadiazin-2-one,
5-[2-(3-fluorophenyl)-1-methyl-1H-benzimidazol-5-yl]-3-(2-hydroxyethyl)-6-methyl]-3,6-dihydro-2H-1,3,4-thiadiazin-2-one,
3-cyclohexylmethyl-5-[2-(3-fluorophenyl)-1-methyl-1H-benzimidazol-5-yl]-6-methyl]-3,6-dihydro-2H-1,3,4-thiadiazin-2-one,
2-{5-[2-(3-fluorophenyl)-1-methyl-1H-benzimidazol-5-yl]-6-methyl-2-oxo-6H-1,3,4-thiadiazin-3-yl}acetamide,
3-[2-(4-fluorophenoxy)ethyl]-5-[2-(3-fluorophenyl)-1-methyl-1H-benzimidazol-5-yl]-6-methyl]-3,6-dihydro-2H-1,3,4-thiadiazin-2-one, 5-[2-(3-fluorophenyl)-1-methyl-1H-benzimidazol-5-yl]-3-isopropyl-6-methyl]-3,6-dihydro-2H-1,3,4-thiadiazin-2-one,
5-[2-(3-fluorophenyl)-1-methyl-1H-benzimidazol-5-yl]-3-isobutyl-6-methyl]-3,6-dihydro-2H-1,3,4-thiadiazin-2-one,
ethyl 4-{5-[2-(3-fluorophenyl)-1-methyl-1H-benzimidazol-5-yl]-6-methyl-2-oxo-6H-1,3,4-thiadiazin-3-yl}butyrate,
ethyl 3-{5-[2-(3-fluorophenyl)-1-methyl-1H-benzimidazol-5-yl]-6-methyl-2-oxo-6H-1,3,4-thiadiazin-3-yl}propionate,
3-cyclopropylmethyl-5-[2-(3-fluorophenyl)-1-methyl-1H-benzimidazol-5-yl]-6-methyl]-3,6-dihydro-2H-1,3,4-thiadiazin-2-one,
5-[2-(3-fluorophenyl)-1-methyl-1H-benzimidazol-5-yl]-3-(2-methoxyethyl)-6-methyl]-3,6-dihydro-2H-1,3,4-thiadiazin-2-one,
3-benzyl-5-[2-(3-fluorophenyl)-1-methyl-1H-benzimidazol-5-yl]-6-methyl]-3,6-dihydro-2H-1,3,4-thiadiazin-2-one,
ethyl {5-[2-(3-fluorophenyl)-1-methyl-1H-benzimidazol-5-yl]-6-methyl-2-oxo-6H-1,3,4-thiadiazin-3-yl}acetate,
5-[2-(3-fluorophenyl)-1-methyl-1H-benzimidazol-5-yl]-6-methyl-3-propyl]-3,6-dihydro-2H-1,3,4-thiadiazin-2-one,
5-[2-(3-fluorophenyl)-1-methyl-1H-benzimidazol-5-yl]-6-methyl-3-(2-morpholin-4-ylethyl)]-3,6-dihydro-2H-1,3,4-thiadiazin-2-one
5-[2-(3-fluorophenyl)-1-methyl-1H-benzimidazol-5-yl]-6-methyl-3-(2-piperidin-1-ylethyl)]-3,6-dihydro-2H-1,3,4-thiadiazin-2-one,
5-[2-(3-fluorophenyl)-1-methyl-1H-benzimidazol-5-yl]-6-methyl]-3,6-dihydro-2H-1,3,4-thiadiazin-2-one,
3-cyclohexylmethyl-5-[2-(3-fluorophenyl)-1-methyl-1H-benzimidazol-5-yl]-3,6-dihydro-2H-1,3,4-thiadiazin-2-one,
2-{5-[2-(3-fluorophenyl)-1-methyl-1H-benzimidazol-5-yl]-2-oxo-6H-1,3,4-thiadiazin-3-yl}acetamide,
3-[2-(4-fluorophenoxy)ethyl]-5-[2-(3-fluorophenyl)-1-methyl-1H-benzimidazol-5-yl]-3,6-dihydro-2H-1,3,4-thiadiazin-2-one,
5-[2-(3-fluorophenyl)-1-methyl-1H-benzimidazol-5-yl]-3-isopropyl]-3,6-dihydro-2H-1,3,4-thiadiazin-2-one,
5-[2-(3-fluorophenyl)-1-methyl-1H-benzimidazol-5-yl]-3-isobutyl]-3,6-dihydro-2H-1,3,4-thiadiazin-2-one,
3-cyclopropylmethyl-5-[2-(3-fluorophenyl)-1-methyl-1H-benzimidazol-5-yl]-3,6-dihydro-2H-1,3,4-thiadiazin-2-one
5-[2-(3-fluorophenyl)-1-methyl-1H-benzimidazol-5-yl]-3-(2-methoxyethyl)]-3,6-dihydro-2H-1,3,4-thiadiazin-2-one,
3-benzyl-5-[2-(3-fluorophenyl)-1-methyl-1H-benzimidazol-5-yl]-3,6-dihydro-2H-1,3,4-thiadiazin-2-one,
ethyl {5-[2-(3-fluorophenyl)-1-methyl-1H-benzimidazol-5-yl]-2-oxo-6H-1,3,4-thiadiazin-3-yl}acetate,
5-[2-(3-fluorophenyl)-1-methyl-1H-benzimidazol-5-yl]-3-(2-piperidin-1-ylethyl)]-3,6-dihydro-2H-1,3,4-thiadiazin-2-one,
5-[2-(3-fluorophenyl)-1-methyl-1H-benzimidazol-5-yl]-3,6-dihydro-2H-1,3,4-thiadiazin-2-one,
5-[2-(3-fluorophenyl)-1-methyl-1H-benzimidazol-5-yl]-3-propyl]-3,6-dihydro-2H-1,3,4-thiadiazin-2-one,
5-(1-benzyl-2-thiophen-3-yl-1H-benzimidazol-5-yl)-6-methyl]-3,6-dihydro-2H-1,3,4-thiadiazin-2-one,
5-[1-benzyl-2-(2-methoxyphenyl)-1H-benzimidazol-5-yl]-6-methyl]-3,6-dihydro-2H-1,3,4-thiadiazin-2-one,
5-[1-cyclopropylmethyl-2-(3-methoxyphenyl)-1H-benzimidazol-5-yl]-6-methyl]-3,6-dihydro-2H-1,3,4-thiadiazin-2-one,
3-cyclohexylmethyl-5-(2-furan-2-yl-1-methyl-1H-benzimidazol-5-yl)]-3,6-dihydro-2H-1,3,4-thiadiazin-2-one,
3-benzyl-5-(2-furan-2-yl-1-methyl-1H-benzimidazol-5-yl)]-3,6-dihydro-2H-1,3,4-thiadiazin-2-one,
3-cyclopropylmethyl-5-(2-furan-2-yl-1-methyl-1H-benzimidazol-5-yl)]-3,6-dihydro-2H-1,3,4-thiadiazin-2-one,
5-(2-furan-2-yl-1-methyl-1H-benzimidazol-5-yl)-3-methyl]-3,6-dihydro-2H-1,3,4-thiadiazin-2-one,
3-ethyl-5-(2-furan-2-yl-1-methyl-1H-benzimidazol-5-yl)]-3,6-dihydro-2H-1,3,4-thiadiazin-2-one,
5-(2-furan-2-yl-1-methyl-1H-benzimidazol-5-yl)-3-(2-piperidin-1-ylethyl)]-3,6-dihydro-2H-1,3,4-thiadiazin-2-one,
5-(2-furan-2-yl-1-methyl-1H-benzimidazol-5-yl)-3-(2-pyrrolidin-1-ylethyl)]-3,6-dihydro-2H-1,3,4-thiadiazin-2-one,
5-(2-furan-2-yl-1-methyl-1H-benzimidazol-5-yl)-3-isobutyl]-3,6-dihydro-2H-1,3,4-thiadiazin-2-one,
5-(2-furan-2-yl-1-methyl-1H-benzimidazol-5-yl)]-3,6-dihydro-2H-1,3,4-thiadiazin-2-one,
2-{5-[2-(3-methoxyphenyl)-1-methyl-1H-benzimidazol-5-yl]-6-methyl-2-oxo-6H-1,3,4-thiadiazin-3-yl}acetamide,
3-isopropyl-5-[2-(3-methoxyphenyl)-1-methyl-1H-benzimidazol-5-yl]-6-methyl]-3,6-dihydro-2H-1,3,4-thiadiazin-2-one,
3-(4-tert-butylbenzyl)-5-[1-methyl-2-(3-trifluoromethylphenyl)-1H-benzimidazol-5-yl]-3,6-dihydro-2H-1,3,4-thiadiazin-2-one,
3-(4-fluorobenzyl)-5-[1-methyl-2-(3-trifluoromethylphenyl)-1H-benzimidazol-5-yl]3,6-dihydro-2H-1,3,4-thiadiazin-2-one,
5-[1-methyl-2-(3-trifluoromethylphenyl)-1H-benzimidazol-5-yl]-3-(4-trifluoromethoxybenzyl)]-3,6-dihydro-2H-1,3,4-thiadiazin-2-one,
5-[1-methyl-2-(3-trifluoromethylphenyl)-1H-benzimidazol-5-yl]-3-(4-trifluoromethylbenzyl)]-3,6-dihydro-2H-1,3,4-thiadiazin-2-one,
3-{5-[1-methyl-2-(3-trifluoromethylphenyl)-1H-benzimidazol-5-yl]-2-oxo-6H-1,3,4-thiadiazin-3-ylmethyl}benzonitrile,
3-(4-methanesulfonylbenzyl)-5-[1-methyl-2-(3-trifluoromethylphenyl)-1H-benzimidazol-5-yl]-3,6-dihydro-2H-1,3,4-thiadiazin-2-one,
3-(3,5-dimethoxybenzyl)-5-[1-methyl-2-(3-trifluoromethylphenyl)-1H-benzimidazol-5-yl]-3,6-dihydro-2H-1,3,4-thiadiazin-2-one,
5-[1-methyl-2-(3-trifluoromethylphenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3,6-dihydro-2H-1,3,4-thiadiazin-2-one,
5-[1-ethyl-2-(3-fluorophenyl)-1H-benzimidazol-5-yl]-3-(4-fluorobenzyl)]-3,6-dihydro-2H-1,3,4-thiadiazin-2-one,
5-[1-ethyl-2-(3-fluorophenyl)-1H-benzimidazol-5-yl]-3-(3-methoxybenzyl)]-3,6-dihydro-2H-1,3,4-thiadiazin-2-one,
5-[1-ethyl-2-(3-fluorophenyl)-1H-benzimidazol-5-yl]-3-(4-trifluoromethoxybenzyl)]-3,6-dihydro-2H-1,3,4-thiadiazin-2-one, 2-{5-[1-ethyl-2-(3-fluorophenyl)-1H-benzimidazol-5-yl]-2-oxo-6H-1,3,4-thiadiazin-3-yl}acetamide, 3-cyclopropylmethyl-5-[1-ethyl-2-(3-fluorophenyl)-1H-benzimidazol-5-yl]-3,6-dihydro-2H-1,3,4-thiadiazin-2-one, 5-[1-ethyl-2-(3-fluorophenyl)-1H-benzimidazol-5-yl]-3-isopropyl]-3,6-dihydro-2H-1,3,4-thiadiazin-2-one, 3-ethyl-5-[1-ethyl-2-(3-fluorophenyl)-1H-benzimidazol-5-yl]-3,6-dihydro-2H-1,3,4-thiadiazin-2-one, 5-[1-ethyl-2-(3-fluorophenyl)-1H-benzimidazol-5-yl]-3-propyl]-3,6-dihydro-2H-1,3,4-thiadiazin-2-one, 5-[1-ethyl-2-(3-fluorophenyl)-1H-benzimidazol-5-yl]-3-(2-methoxyethyl)]-3,6-dihydro-2H-1,3,4-thiadiazin-2-one, {5-[1-ethyl-2-(3-fluorophenyl)-1H-benzimidazol-5-yl]-2-oxo-6H-1,3,4-thiadiazin-3-yl}acetic acid, 5-[1-ethyl-2-(3-fluorophenyl)-1H-benzimidazol-5-yl]-3-(2-hydroxyethyl)]-3,6-dihydro-2H-1,3,4-thiadiazin-2-one, 5-[1-ethyl-2-(3-fluorophenyl)-1H-benzimidazol-5-yl]-3-(3-hydroxypropyl)]-3,6-dihydro-2H-1,3,4-thiadiazin-2-one, 3-(2-aminoethyl)-5-[1-ethyl-2-(3-fluorophenyl)-1H-benzimidazol-5-yl]-3,6-dihydro-2H-1,3,4-thiadiazin-2-one, 3-(3-aminopropyl)-5-[1-ethyl-2-(3-fluorophenyl)-1H-benzimidazol-5-yl]-3,6-dihydro-2H-1,3,4-thiadiazin-2-one, 3-benzyl-5-[1-ethyl-2-(3-methoxyphenyl)-1H-benzimidazol-5-yl]-3,6-dihydro-2H-1,3,4-thiadiazin-2-one, 5-[1-ethyl-2-(3-methoxyphenyl)-1H-benzimidazol-5-yl]-3-(4-methylbenzyl)]-3,6-dihydro-2H-1,3,4-thiadiazin-2-one, 5-[1-ethyl-2-(3-methoxyphenyl)-1H-benzimidazol-5-yl]-3-(2-fluorobenzyl)]-3,6-dihydro-2H-1,3,4-thiadiazin-2-one, 3-benzyl-5-[1-methyl-2-(3-trifluoromethylphenyl)-1H-benzimidazol-5-yl]-3,6-dihydro-2H-1,3,4-thiadiazin-2-one, 3-methyl-5-[1-methyl-2-(3-trifluoromethylphenyl)-1H-benzimidazol-5-yl]-3,6-dihydro-2H-1,3,4-thiadiazin-2-one, 3-cyclohexylmethyl-5-[1-methyl-2-(3-trifluoromethylphenyl)-1H-benzimidazol-5-yl]-3,6-dihydro-2H-1,3,4-thiadiazin-2-one, 3-(3-aminopropyl)-5-[1-methyl-2-(3-trifluoromethylphenyl)-1H-benzimidazol-5-yl]-3,6-dihydro-2H-1,3,4-thiadiazin-2-one, 3-(2-aminoethyl)-5-[1-methyl-2-(3-trifluoromethylphenyl)-1H-benzimidazol-5-yl]-3,6-dihydro-2H-1,3,4-thiadiazin-2-one, 3-(2-aminoethyl)-5-[1-ethyl-2-(3-methoxyphenyl)-1H-benzimidazol-5-yl]-3,6-dihydro-2H-1,3,4-thiadiazin-2-one, 3-(3-aminopropyl)-5-[1-ethyl-2-(3-methoxyphenyl)-1H-benzimidazol-5-yl]-3,6-dihydro-2H-1,3,4-thiadiazin-2-one, 5-[1-ethyl-2-(3-methoxyphenyl)-1H-benzimidazol-5-yl]-3-(2-hydroxyethyl)]-3,6-dihydro-2H-1,3,4-thiadiazin-2-one 5-[1-ethyl-2-(3-methoxyphenyl)-1H-benzimidazol-5-yl]-3-(3-hydroxypropyl)]-3,6-dihydro-2H-1,3,4-thiadiazin-2-one, N-(2-{5-[1-methyl-2-(3-trifluoromethylphenyl)-1H-benzimidazol-5-yl]-2-oxo-6H-1,3,4-thiadiazin-3-yl}ethyl)acetamide, furan-2-carboxylic acid (2-{5-[1-methyl-2-(3-trifluoromethylphenyl)-1H-benzimidazol-5-yl]-2-oxo-6H-1,3,4-thiadiazin-3-yl}ethyl)amide, N-(2-{5-[1-methyl-2-(3-trifluoromethylphenyl)-1H-benzimidazol-5-yl]-2-oxo-6H-1,3,4-thiadiazin-3-yl}ethyl)isobutyramide, cyclopentanecarboxylic acid (2-{5-[1-methyl-2-(3-trifluoromethylphenyl)-1H-benzimidazol-5-yl]-2-oxo-6H-1,3,4-thiadiazin-3-yl}ethyl)amide, N-(2-{5-[1-methyl-2-(3-trifluoromethylphenyl)-1H-benzimidazol-5-yl]-2-oxo-6H-1,3,4-thiadiazin-3-yl}ethyl)benzamide, N-(2-{5-[1-methyl-2-(3-trifluoromethylphenyl)-1H-benzimidazol-5-yl]-2-oxo-6H-1,3,4-thiadiazin-3-yl}ethyl)methanesulfonamide, N-(2-{5-[1-methyl-2-(3-trifluoromethylphenyl)-1H-benzimidazol-5-yl]-2-oxo-6H-1,3,4-thiadiazin-3-yl}ethyl)benzenesulfonamide, 5-[1-methyl-2-(3-trifluoromethylphenyl)-1H-benzimidazol-5-yl]-6-propyl]-3,6-dihydro-2H-1,3,4-thiadiazin-2-one, 3-ethyl-5-[1-methyl-2-(3-trifluoromethylphenyl)-1H-benzimidazol-5-yl]-6-propyl]-3,6-dihydro-2H-1,3,4-thiadiazin-2-one, 5-[1-methyl-2-(3-trifluoromethylphenyl)-1H-benzimidazol-5-yl]-3,6-dipropyl]-3,6-dihydro-2H-1,3,4-thiadiazin-2-one, 3-benzyl-5-[1-methyl-2-(3-trifluoromethylphenyl)-1H-benzimidazol-5-yl]-6-propyl]-3,6-dihydro-2H-1,3,4-thiadiazin-2-one, 3-cyclopropylmethyl-5-[1-methyl-2-(3-trifluoromethylphenyl)-1H-benzimidazol-5-yl]-6-propyl]-3,6-dihydro-2H-1,3,4-thiadiazin-2-one, 3-isopropyl-5-[1-methyl-2-(3-trifluoromethylphenyl)-1H-benzimidazol-5-yl]-6-propyl]-3,6-dihydro-2H-1,3,4-thiadiazin-2-one, 3-isobutyl-5-[1-methyl-2-(3-trifluoromethylphenyl)-1H-benzimidazol-5-yl]-6-propyl]-3,6-dihydro-2H-1,3,4-thiadiazin-2-one, 5-[1-methyl-2-(3-trifluoromethylphenyl)-1H-benzimidazol-5-yl]-3-(2-piperidin-1-ylethyl)-6-propyl]-3,6-dihydro-2H-1,3,4-thiadiazin-2-one, 5-[1-methyl-2-(3-trifluoromethylphenyl)-1H-benzimidazol-5-yl]-6-propyl-3-(2-pyrrolidin-1-ylethyl)]-3,6-dihydro-2H-1,3,4-thiadiazin-2-one, 1-(2-{5-[1-methyl-2-(3-trifluoromethylphenyl)-1H-benzimidazol-5-yl]-2-oxo-6H-1,3,4-thiadiazin-3-yl}ethyl)-3-phenylurea, 1-ethyl-3-(2-{5-[1-methyl-2-(3-trifluoromethylphenyl)-1H-benzimidazol-5-yl]-2-oxo-6H-1,3,4-thiadiazin-3-yl}ethyl)urea, 5-[1-ethyl-2-(3-methoxyphenyl)-1H-benzimidazol-5-yl]-3,6-dihydro-2H-1,3,4-thiadiazin-2-one, 3-cyclopropylmethyl-5-[1-methyl-2-(3-trifluoromethylphenyl)-1H-benzimidazol-5-yl]-3,6-dihydro-2H-1,3,4-thiadiazin-2-one, butane-1-sulfonic acid (2-{5-[1-methyl-2-(3-trifluoromethylphenyl)-1H-benzimidazol-5-yl]-2-oxo-6H-1,3,4-thiadiazin-3-yl}ethyl)amide, N-{2-[5-(2-furan-2-yl-1-methyl-1H-benzimidazol-5-yl)-2-oxo-6H-1,3,4-thiadiazin-3-yl]ethyl}acetamide, N-{2-[5-(2-furan-2-yl-1-methyl-1H-benzimidazol-5-yl)-2-oxo-6H-1,3,4-thiadiazin-3-yl]ethyl}isobutyramide, cyclopentanecarboxylic acid {2-[5-(2-furan-2-yl-1-methyl-1H-benzimidazol-5-yl)-2-oxo-6H-1,3,4-thiadiazin-3-yl]ethyl}amide, N-{2-[5-(2-furan-2-yl-1-methyl-1H-benzimidazol-5-yl)-2-oxo-6H-1,3,4-thiadiazin-3-yl]ethyl}benzamide,
N-{2-[5-(2-furan-2-yl-1-methyl-1H-benzimidazol-5-yl)-2-oxo-6H-1,3,4-thiadiazin-3-yl]ethyl}nicotinamide,
cyclopropanecarboxylic acid {2-[5-(2-furan-2-yl-1-methyl-1H-benzimidazol-5-yl)-2-oxo-6H-1,3,4-thiadiazin-3-yl]ethyl}amide,
3-fluoro-N-{2-[5-(2-furan-2-yl-1-methyl-1H-benzimidazol-5-yl)-2-oxo-6H-1,3,4-thiadiazin-3-yl]ethyl}benzamide,
N-{2-[5-(2-furan-2-yl-1-methyl-1H-benzimidazol-5-yl)-2-oxo-6H-1,3,4-thiadiazin-3-yl]ethyl}-4-methylbenzamide,
3-(2-aminoethyl)-5-(2-furan-2-yl-1-methyl-1H-benzimidazol-5-yl)]-3,6-dihydro-2H-1,3,4-thiadiazin-2-one,
N-{2-[5-(2-furan-2-yl-1-methyl-1H-benzimidazol-5-yl)-2-oxo-6H-1,3,4-thiadiazin-3-yl]ethyl}benzenesulfonamide,
butane-1-sulfonic acid {2-[5-(2-furan-2-yl-1-methyl-1H-benzimidazol-5-yl)-2-oxo-6H-1,3,4-thiadiazin-3-yl]ethyl}amide,
1-{2-[5-(2-furan-2-yl-1-methyl-1H-benzimidazol-5-yl)-2-oxo-6H-1,3,4-thiadiazin-3-yl]ethyl}-3-isopropylurea,
1-{2-[5-(2-furan-2-yl-1-methyl-1H-benzimidazol-5-yl)-2-oxo-6H-1,3,4-thiadiazin-3-yl]ethyl}-3-phenylurea,
1-cyclopentyl-3-{2-[5-(2-furan-2-yl-1-methyl-1H-benzimidazol-5-yl)-2-oxo-6H-1,3,4-thiadiazin-3-yl]ethyl}urea,
1-ethyl-3-{2-[5-(2-furan-2-yl-1-methyl-1H-benzimidazol-5-yl)-2-oxo-6H-1,3,4-thiadiazin-3-yl]ethyl}urea,
1-benzyl-3-{2-[5-(2-furan-2-yl-1-methyl-1H-benzimidazol-5-yl)-2-oxo-6H-1,3,4-thiadiazin-3-yl]ethyl}urea,
1-(4-fluorobenzyl)-3-{2-[5-(2-furan-2-yl-1-methyl-1H-benzimidazol-5-yl)-2-oxo-6H-1,3,4-thiadiazin-3-yl]ethyl}urea,
1-(4-acetylphenyl)-3-{2-[5-(2-furan-2-yl-1-methyl-1H-benzimidazol-5-yl)-2-oxo-6H-1,3,4-thiadiazin-3-yl]ethyl}urea,
1-{2-[5-(2-furan-2-yl-1-methyl-1H-benzimidazol-5-yl)-2-oxo-6H-1,3,4-thiadiazin-3-yl]ethyl}-3-p-tolylurea,
1-butyl-3-{2-[5-(2-furan-2-yl-1-methyl-1H-benzimidazol-5-yl)-2-oxo-6H-1,3,4-thiadiazin-3-yl]ethyl}urea,
N-{3-[5-(2-furan-2-yl-1-methyl-1H-benzimidazol-5-yl)-2-oxo-6H-1,3,4-thiadiazin-3-yl]propyl}benzamide,
cyclopropanecarboxylic acid {3-[5-(2-furan-2-yl-1-methyl-1H-benzimidazol-5-yl)-2-oxo-6H-1,3,4-thiadiazin-3-yl]propyl}amide,
1-(4-chlorophenyl)-3-{2-[5-(2-furan-2-yl-1-methyl-1H-benzimidazol-5-yl)-2-oxo-6H-1,3,4-thiadiazin-3-yl]ethyl}urea,
1-(4-chlorophenyl)-3-{3-[5-(2-furan-2-yl-1-methyl-1H-benzimidazol-5-yl)-2-oxo-6H-1,3,4-thiadiazin-3-yl]propyl}urea,
1-butyl-3-{3-[5-(2-furan-2-yl-1-methyl-1H-benzimidazol-5-yl)-2-oxo-6H-1,3,4-thiadiazin-3-yl]propyl}urea,
1-benzyl-3-{3-[5-(2-furan-2-yl-1-methyl-1H-benzimidazol-5-yl)-2-oxo-6H-1,3,4-thiadiazin-3-yl]propyl}urea,
1-(3-fluorophenyl)-3-{3-[5-(2-furan-2-yl-1-methyl-1H-benzimidazol-5-yl)-2-oxo-6H-1,3,4-thiadiazin-3-yl]propyl}urea
N-{2-[5-(2-furan-2-yl-1-methyl-1H-benzimidazol-5-yl)-2-oxo-6H-1,3,4-thiadiazin-3-yl]ethyl}methanesulfonamide,
5-(2-furan-2-yl-1-methyl-1H-benzimidazol-5-yl)-3-(2-methoxyethyl)]-3,6-dihydro-2H-1,3,4-thiadiazin-2-one,
5-(2-furan-2-yl-1-methyl-1H-benzimidazol-5-yl)-3-(3-hydroxypropyl)]-3,6-dihydro-2H-1,3,4-thiadiazin-2-one,
5-(2-furan-2-yl-1-methyl-1H-benzimidazol-5-yl)-3-(2-hydroxyethyl)]-3,6-dihydro-2H-1,3,4-thiadiazin-2-one,
3-(3-aminopropyl)-5-(2-furan-2-yl-1-methyl-1H-benzimidazol-5-yl)]-3,6-dihydro-2H-1,3,4-thiadiazin-2-one,
3-(2-aminoethyl)-5-[2-(3-fluorophenyl)-1-methyl-1H-benzimidazol-5-yl]-6-methyl]-3,6-dihydro-2H-1,3,4-thiadiazin-2-one,
N-(2-{5-[2-(3-fluorophenyl)-1-methyl-1H-benzimidazol-5-yl]-6-methyl-2-oxo-6H-1,3,4-thiadiazin-3-yl}ethyl)-2-phenylacetamide,
N-(2-{5-[2-(3-fluorophenyl)-1-methyl-1H-benzimidazol-5-yl]-6-methyl-2-oxo-6H-1,3,4-thiadiazin-3-yl}ethyl)-4-methylbenzamide,
cyclopropanecarboxylic acid (2-{5-[2-(3-fluorophenyl)-1-methyl-1H-benzimidazol-5-yl]-6-methyl-2-oxo-6H-1,3,4-thiadiazin-3-yl}ethyl)amide,
cyclopentanecarboxylic acid (2-{5-[2-(3-fluorophenyl)-1-methyl-1H-benzimidazol-5-yl]-6-methyl-2-oxo-6H-1,3,4-thiadiazin-3-yl}ethyl)amide,
N-(2-{5-[2-(3-fluorophenyl)-1-methyl-1H-benzimidazol-5-yl]-6-methyl-2-oxo-6H-1,3,4-thiadiazin-3-yl}ethyl)-2-methoxyacetamide,
N-(2-{5-[2-(3-fluorophenyl)-1-methyl-1H-benzimidazol-5-yl]-6-methyl-2-oxo-6H-1,3,4-thiadiazin-3-yl}ethyl)nicotinamide,
N-(2-{5-[2-(3-fluorophenyl)-1-methyl-1H-benzimidazol-5-yl]-6-methyl-2-oxo-6H-1,3,4-thiadiazin-3-yl}ethyl)benzamide,
N-(2-{5-[2-(3-fluorophenyl)-1-methyl-1H-benzimidazol-5-yl]-6-methyl-2-oxo-6H-1,3,4-thiadiazin-3-yl}ethyl)acetamide,
N-(2-{5-[2-(3-fluorophenyl)-1-methyl-1H-benzimidazol-5-yl]-6-methyl-2-oxo-6H-1,3,4-thiadiazin-3-yl}ethyl)isobutyramide,
(S)-5-{2-[4-((S)-methanesulfinyl)-3-methoxyphenyl]-1H-benzimidazol-5-yl}-6-methyl]-3,6-dihydro-2H-1,3,4-thiadiazin-2-one,
(R)-5-{2-[4-((S)-methanesulfinyl)-3-methoxyphenyl]-1H-benzimidazol-5-yl}-6-methyl]-3,6-dihydro-2H-1,3,4-thiadiazin-2-one,
(S)-5-{2-[4-((R)-methanesulfinyl)-3-methoxyphenyl]-1H-benzimidazol-5-yl}-6-methyl]-3,6-dihydro-2H-1,3,4-thiadiazin-2-one,
(R)-5-{2-[4-((R)-methanesulfinyl)-3-methoxyphenyl]-1H-benzimidazol-5-yl}-6-methyl]-3,6-dihydro-2H-1,3,4-thiadiazin-2-one,
1-(4-acetylphenyl)-3-(2-{5-[2-(3-fluorophenyl)-1-methyl-1H-benzimidazol-5-yl]-6-methyl-2-oxo-6H-1,3,4-thiadiazin-3-yl}ethyl)urea,
1-(3-fluorophenyl)-3-(2-{5-[2-(3-fluorophenyl)-1-methyl-1H-benzimidazol-5-yl]-6-methyl-2-oxo-6H-1,3,4-thiadiazin-3-yl}ethyl)urea,
5-[1-cyclopropylmethyl-2-(1-methyl-1H-pyrrol-2-yl)-1H-benzimidazol-5-yl]-6-methyl]-3,6-dihydro-2H-1,3,4-thiadiazin-2-one,
5-[1-cyclopropylmethyl-2-(1-methyl-1H-imidazol-2-yl)-1H-benzimidazol-5-yl]-6-methyl]-3,6-dihydro-2H-1,3,4-thiadiazin-2-one,
5-(1-cyclopropylmethyl-2-thiophen-3-yl-1H-benzimidazol-5-yl)-6-methyl]-3,6-dihydro-2H-1,3,4-thiadiazin-2-one, 5-[1-cyclopropylmethyl-2-(2-methoxyphenyl)-1H-benz-
imidazol-5-yl]-6-methyl]-3,6-dihydro-2H-1,3,4-thiadi-
azin-2-one, 5-[1-cyclopropylmethyl-2-(4-methoxyphenyl)-1H-benz-
imidazol-5-yl]-6-methyl]-3,6-dihydro-2H-1,3,4-thiadi-
azin-2-one, and 5-[1-cyclopropylmethyl-2-(3-hydroxy-4-methoxyphe-
nyl)-1H-benzimidazol-5-yl]-6-methyl]-3,6-dihydro-
2H-1,3,4-thiadiazin-2-one, and the tautomeric forms thereof, enantiomers thereof,
diastereoisomers thereof, epimers thereof, pharmaceu-
tically acceptable salts thereof, or mixtures thereof.

6. A compound according to claim 1, wherein said com-
pound is selected from:

5-[2-(3-fluorophenyl)-1-methyl-1H-benzimidazol-5-yl]-
3-isopropyl-6-methyl]-3,6-dihydro-2H-1,3,4-thiadi-
azin-2-one, 5-[2-(3-fluorophenyl)-1-methyl-1H-benzimidazol-5-yl]-
6-methyl-3-propyl]-3,6-dihydro-2H-1,3,4-thiadiazin-
2-one, 5-{2-[4-(1H-imidazol-1-yl)phenyl]-1H-benzimidazol-5-
yl}-6-methyl-3,6-dihydro-2H-1,3,4-thiadiazin-2-one
dihydrochloride, 5-[1-cycloheptyl-2-(3-methoxyphenyl)-1H-benzimida-
zol-5-yl]-3-methyl]-3,6-dihydro-2H-1,3,4-thiadiazin-
2-one, 6-methyl-5-{2-[3-(methoxy)phenyl]-1H-benzimidazol-5-
yl}-3,6-dihydro-2H-1,3,4-thiadiazin-2-one, and 5-{2-[3-methoxy-4-(methylsulfinyl)phenyl]-1H-benzimi-
dazol-5-yl}-6-methyl-3,6-dihydro-2H-1,3,4-thiadi-
azin-2-one hydrochloride, and the tautomeric forms thereof, enantiomers thereof,
diastereoisomers thereof, epimers thereof, pharmaceu-
tically acceptable salts thereof, or mixtures thereof.

7. A process for the preparation of a compound according
to claim 1, in which R3 is other than a hydrogen atom, said
process comprising:

substituting the compound of formula (F) below:

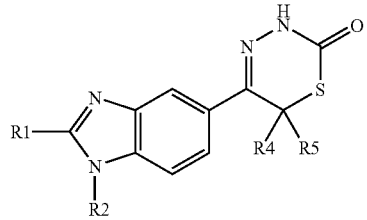

(F)

in which R1, R2, R4 and R5 are as defined in formula (I),
using a suitable reagent, depending on the value of the desired
group R3, optionally followed by one or more suitable functionaliza-
tions.

8. The process according to claim 7, wherein the substitu-
tion corresponds to:

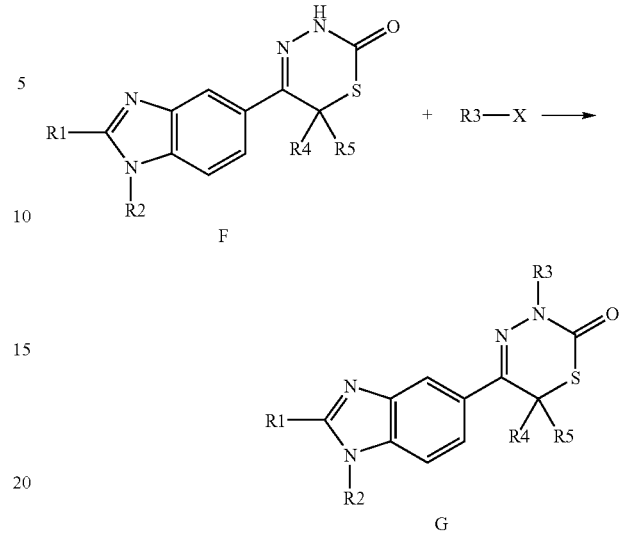

in which R1, R2, R4 and R5 are as defined in claim 7, R3 is
other than H, and X represents a halogen atom.

9. The process according to claim 7, wherein the substitu-
tion corresponds to the following reactions:

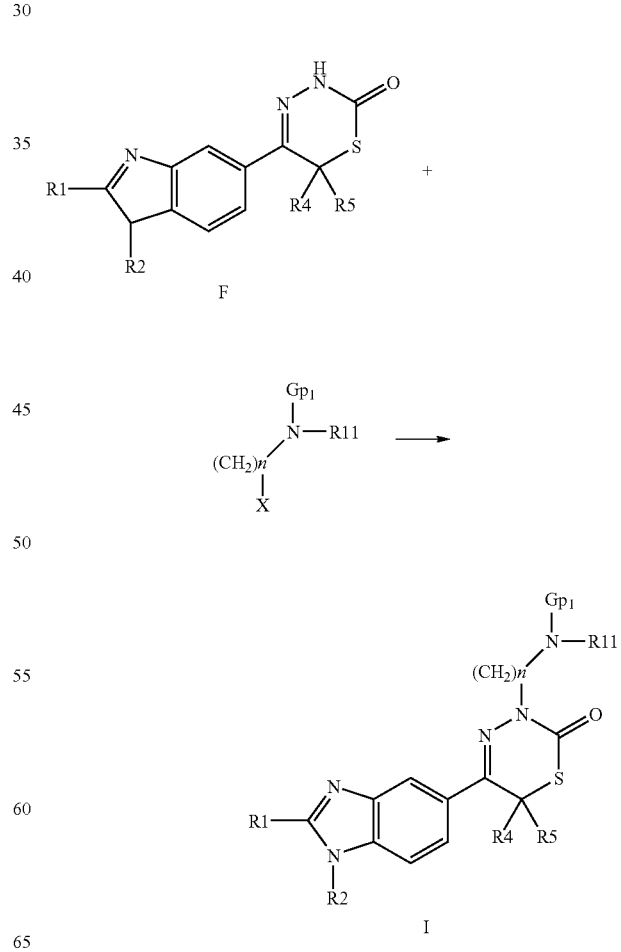

followed by

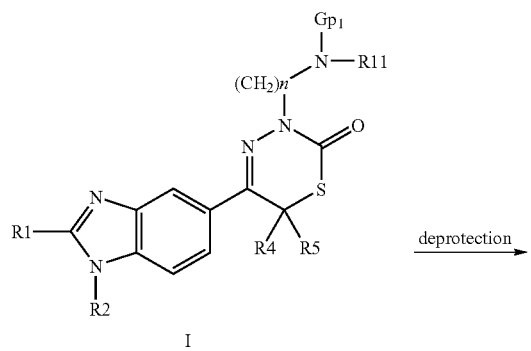

I deprotection

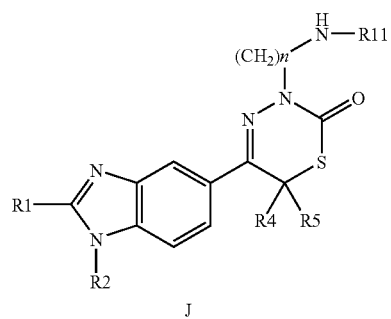

J in which R1, R2, R4, R5 and R11 are as defined according to claim 7, X represents a halogen atom, n represents an integer between 1 and 10, and Gp1 is an amine-protecting group.

10. A process according to claim 7, wherein said functionalizations corresponds to:

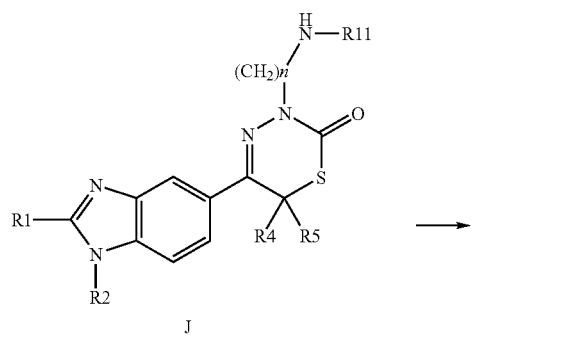

J

→

K via the action of a suitably selected acid halide of the formula Hal-CO—R14
in which R1, R2, R4, R5, R11, R14 and n are as defined according to claim 7 and Hal represents a halogen atom.

11. A process according to claim 7, wherein said functionalizations corresponds to:

J

→

L via the action of a suitably selected sulfonyl halide of the formula Hal-S(O)$_p$—R15
in which R1, R2, R4, R5, R11, R14, R15 and p are as defined according to claim 7 and Hal represents a halogen atom.

12. A process according to claim 7, wherein said functionalizations corresponds to:

J

→

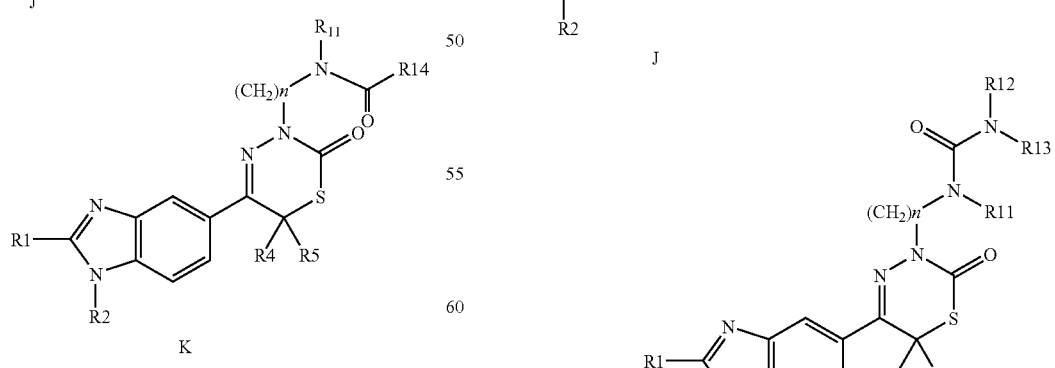
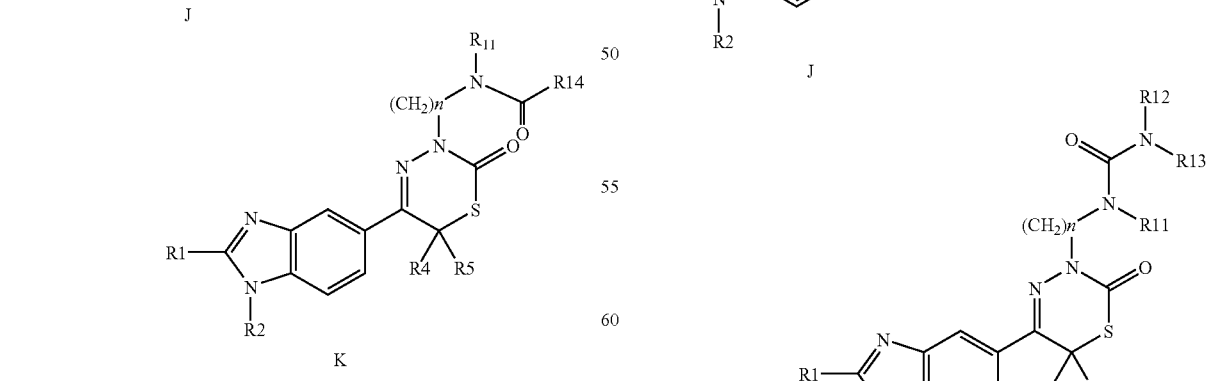
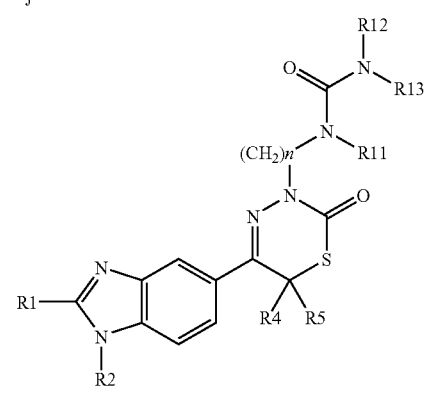

M in which R1, R2, R4, R5, R11, R12, R13 and n are as defined according to claim 7, using an isothiocyanate corresponding to the formula R13-N=C=O, if R12 is a hydrogen and R13 is other than a hydrogen.

13. A process according to claim 7, wherein said functionalizations corresponds to:

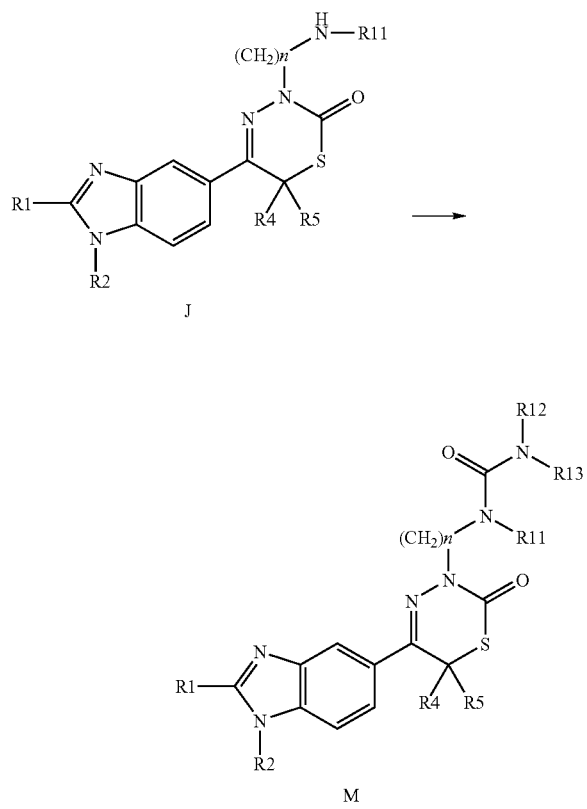

in which R1, R2, R4, R5, R11, R12, R13 and n are as defined according to claim 7, using carbonyldiimidazole followed by a corresponding amine NHR12R13 if R12 and R13 are both other than a hydrogen atom.

14. A process according to claim 7, wherein said functionalizations corresponds to:

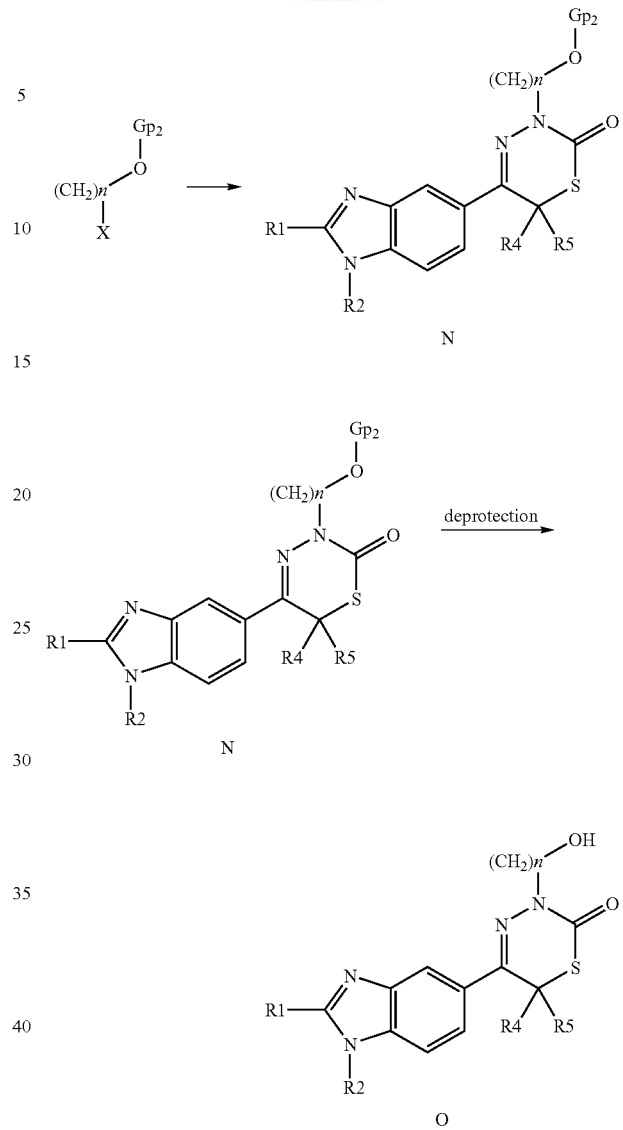

in which R1, R2, R4, R5 and n are as defined according to claim 7, X represents a halogen atom, and Gp2 represents an alcohol-protecting group.

15. The process according to claim 7, wherein the compound of formula (F) is obtained by

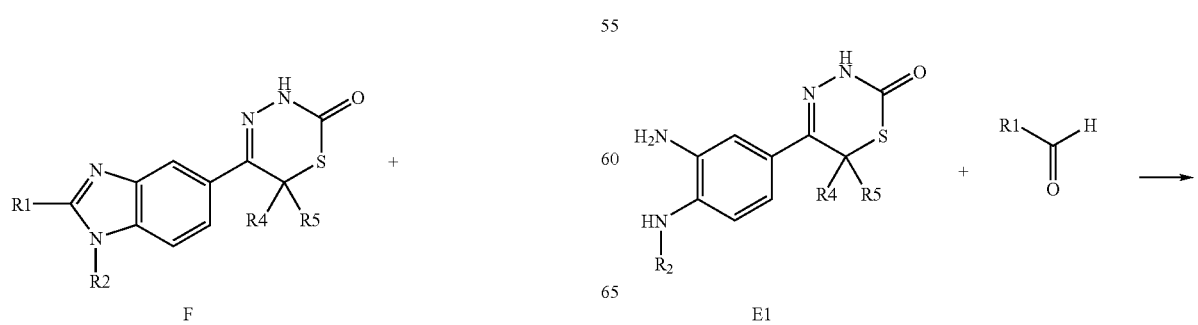

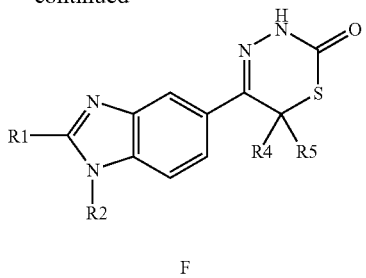

F in which R1, R2, R4 and R5 are as defined according to claim 7.

16. The process according to claim 7, wherein the compound of formula (F) is obtained by

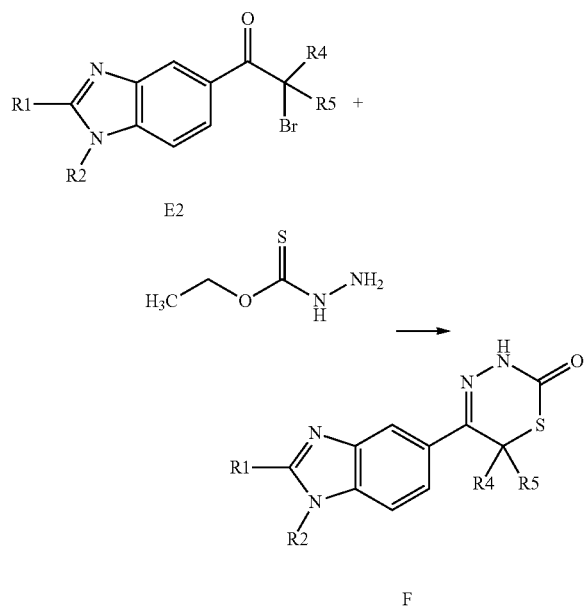

F in which R1, R2, R4 and R5 are as defined according to claim 7.

17. The process according to claim 7, further comprising isolating the product obtained.

18. A pharmaceutical composition comprising at least one compound according to claim 1 and at least one pharmaceutically acceptable excipient and/or vehicle.

19. A method for the treatment of diabetes mellitus comprising administering an effective amount of a compound of according to claim 1.

20. The method according to claim 19, wherein said diabetes is non-insulin-dependent diabetes (type II diabetes or NIDDM).

21. A method for the treatment of dyslipidaemia, obesity, arterial hypertension, atherosclerosis, myocardial ischaemia, hypercholesterolaemia, and hyperlipidaemia, comprising administering an effective amount of a compound of according to claim 1.

22. The method according to claim 21, for the treatment of dyslipidaemia, hyperlipidaemia or hypercholesterolaemia.

23. The method according to claim 21, for the treatment of obesity.

24. The method according to claim 21, for treatment of arterial hypertension or myocardial ischaemia.

25. A method for inhibiting or limiting the hepatic production of glucose comprising administering to a patient an effective amount of a compound according to claim 1.

26. A compound according to claim 1, wherein

R1 is phenyl which is optionally substituted by one to four identical or different groups independently chosen from halogen, —OR, perhaloalkyl-, —S(O)$_p$—R, —NRR', —S—CH$_2$—CN or heteroaryl, or R1 is pyrrolyl, imidazolyl, thiophenyl, furanyl, pyrazolyl, thienyl, pyridyl, or thiazolyl which in each case is optionally substituted by one or more alkyl groups.

* * * * *

UNITED STATES PATENT AND TRADEMARK OFFICE
CERTIFICATE OF CORRECTION

PATENT NO.       : 8,232,272 B2                                Page 1 of 1
APPLICATION NO.  : 12/742375
DATED            : July 31, 2012
INVENTOR(S)      : Gerard Botton et al.

It is certified that error appears in the above-identified patent and that said Letters Patent is hereby corrected as shown below:

Column 88, Line 1 reads: "5-[2-(3-methoxy-4-(methyllhio)phenyl]-1H-benzimida-" should read -- 5-{2-[3-methoxy-4-(methylthio)phenyl]-1H-benzimida- --.

Column 88, Line 2 reads: "zol-5-yl]-6-methyl-3,6-dihydro-2H-1,3,4-thiadiazine-2-" should read -- zol-5-yl}-6-methyl-3,6-dihydro-2H-1,3,4-thiadiazine-2- --.

Column 88, Line 4 reads: "5-[2-(2-methoxy-4-methylthio)phenyl]-1H-benzimida-" should read -- 5-{2-[2-methoxy-4-(methylthio)phenyl]-1-H-benzimida --.

Column 88, Line 5 reads: "zol-5-yl]-6-methyl-3,6-dihydro-2H-1,3,4-thiadiazine-2-" should read -- zol-5-yl}-6-methyl-3,6-dihydro-2H-1,3,4-thiadiazine-2- --.

Column 100, Line 35, delete:

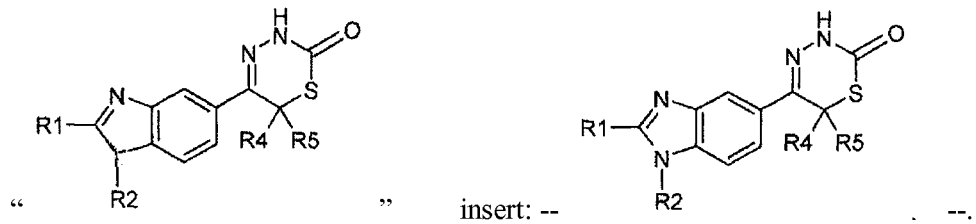

Signed and Sealed this
Twenty-seventh Day of November, 2012

David J. Kappos
*Director of the United States Patent and Trademark Office*